Figure 1A:
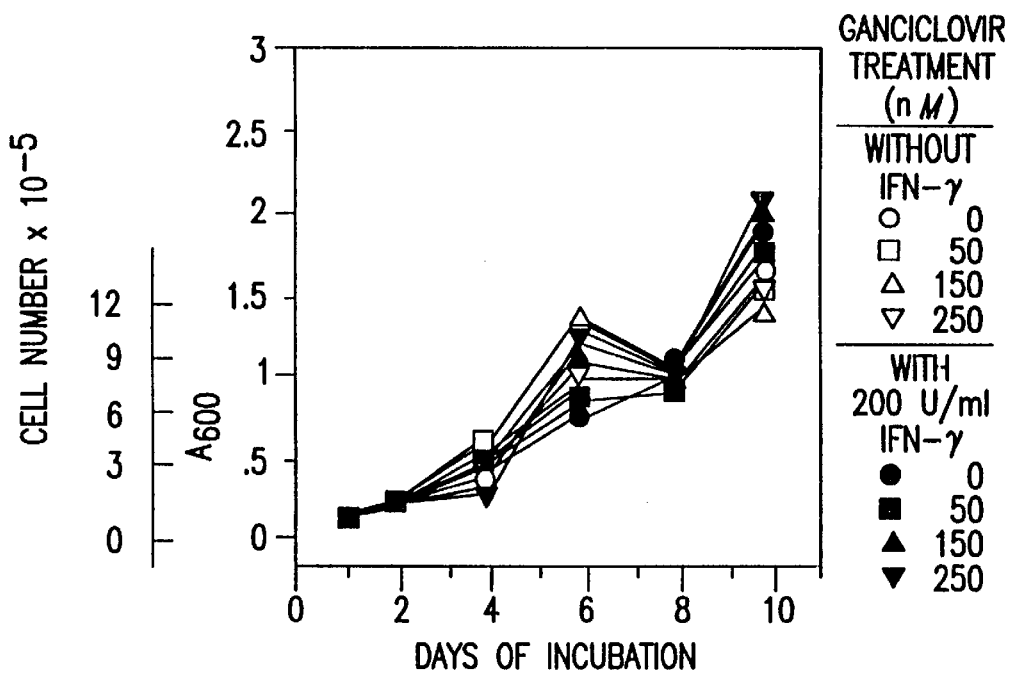
Figure 1B:
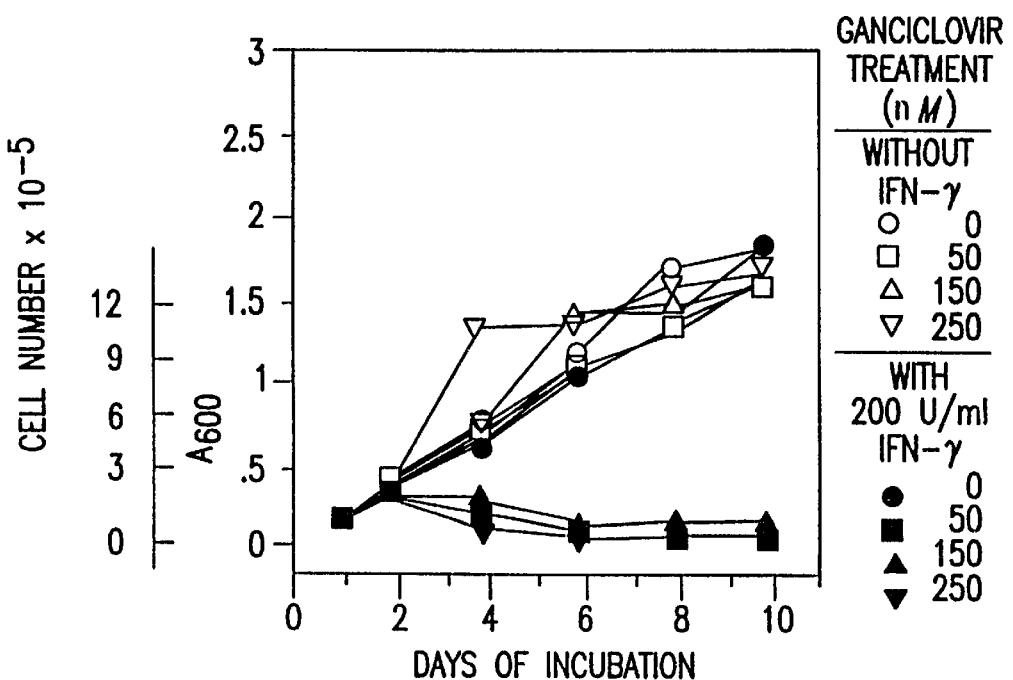

United States Patent [19]

Peyman

[11] Patent Number: 6,022,863
[45] Date of Patent: Feb. 8, 2000

[54] REGULATION OF GENE EXPRESSION

[75] Inventor: John A. Peyman, Cheshire, Conn.

[73] Assignee: Yale University, New Haven, Conn.

[21] Appl. No.: 08/646,789

[22] Filed: May 21, 1996

[51] Int. Cl.[7] .................................................. C12N 15/11
[52] U.S. Cl. ........................ 514/44; 536/24.1; 435/325; 435/1.1; 435/91.1; 800/13; 800/25
[58] Field of Search .................... 536/23.1, 24.1, 536/24.33; 435/325, 1.1, 91.1; 514/44; 800/13, 25

[56] References Cited

U.S. PATENT DOCUMENTS 5,166,057  11/1992  Palese et al. .............................. 435/93

FOREIGN PATENT DOCUMENTS 9115599  10/1991  WIPO .
93/02188  2/1996  WIPO .

OTHER PUBLICATIONS

Adams et al., 1995, TIGR, Accession No. T32811.
Adams et al., 1995, TIGR, Accession No. T30784.
Aguet et al., 1988, Cell 55:273–280.
Altshul et al., 1990, J. Mol. Biol. 215:403–410.
Ausubel et al., 1987, *Current Protocols in Molecular Biology*. (John Wiley & Sons, New York, NY), Suppl. 9, pp. 10.0.1–10.0.3 and Suppl. 2, pp. 10.0.1–10.0.2.
Bao et al., 1994, Transplantation 58:585–591.
Beltinger et al., 1995, J. Clin. Invest. 95:1814–1823.
Benech et al., 1992, J. Exp. Med. 176:1115–1123
Bodnar and Ward, 1987, Nucl. Acids Res. 15:1835–1851.
Chang et al., 1994, J. Exp. Med. 180:1367–1374.
Clover et al., 1995, Eur. J. Immunol. 25:543–548.
Cross et al., 1994, Science 266:1508–1518.
Darnell et al., 1994, Science 264:1415–1421.
Das et al., 1983, Proc. Natl. Acad. Sci. USA 80:3543–3547.
Devereux et al., 1984, Nucl. Acids Res. 12:387–395.
Draper, 1995, Ann. Rev. Biochem. 64:593–620.
Durbin et al., 1996, Cell 84:443–450.
Fang et al., 1994, Transpl. Proc. 26(6):3467.
Felgner et al., 1987, Proc. Natl. Acad. Sci. USA 84:7413–7417.
Fujiwara et al., 1995, GenBank, Accession No. C16114.
Fujiwara et al., 1995, GenBank, Accession No. D57771.
Fujiwara et al., 1995, GenBank, Accession No. D67621.
Fujiwara et al., 1995, GenBank, Accession No. D58883.
Fujiwara et al., 1995, GenBank, Accession No. C16136.
Fujiwara et al., 1995, GenBank, Accession No. C16392.
Geraghty et al., 1987, Proc. Natl. Acad. Sci. USA 84:9145–9149.
Germain, 1994, Cell 76:287–299.
Ghosh, 1990, Nucl. Acids Res. 18:1749–1756.
Glimcher and Kara, 1992, Annu. Rev. Immunol. 10:13–49.
Greenlund et al., 1995, Immunity 2:677–687.
Hammond and Havre, 1992, Transplantation Proc. 24(2):462–467.
Harlow and Lane, 1988, *Antibodies. A Laboratory Manual*. (Cold Spring Harbor Laboratory Press, Cold Spring Harbor, NY), pp. iii–ix.
Hassanain et al., 1993, J. Biol. Chem. 268:5077–5084.
Hemmi et al., 1994, Cell 76:803–810.
Herschbach and Johnson, 1993, Annu. Rev. Cell Biol. 9:479–509.
Hillier et al., 1995, GenBank, Accession No. N93217.
Hillier et al., 1995, GenBank, Accession No. N92350.
Hillier et al., 1995, GenBank, Accession No. W38907.
Hillier et al., 1995, GenBank, Accession No. N98703.
Hillier et al., 1995, GenBank, Accession No. W16798.
Hillier et al., 1995, GenBank, Accession No. W16857.
Hillier et al., 1995, GenBank, Accession No. W37790.
Hillier et al., 1995, GenBank, Accession No. W37277.
Hillier et al., 1995, GenBank, Accession No. N90593.
Hillier et al., 1995, GenBank, Accession No. W56093.
Hillier et al., 1995, GenBank, Accession No. N89791.
Hillier et al., 1995, GenBank, Accession No. N67461.
Hillier et al., 1995, GenBank, Accession No. W38857.
Hillier et al., 1995, GenBank, Accession No. N94954.
Hillier et al., 1995, GenBank, Accession No. W31446.
Hillier et al., 1995, GenBank, Accession No. AA016190.
Hillier et al., 1995, GenBank, Accession No. AA054357.
Hillier et al., 1995, GenBank, Accession No. W56012.
Hillier et al., 1995, GenBank, Accession No. W56123.
Hillier et al., 1995, GenBank, Accession No. AA053611.
Hillier et al., 1995, GenBank, Accession No. AA010866.
Hillier et al., 1995, GenBank, Assession No. AA045252.
Hillier et al., 1995, GenBank, Assession No. AA010989.
Hillier et al., 1995, GenBank, Assession No. W56683.
Hillier et al., 1995, GenBank, Assession No. W57753.
Hillier et al., 1995, GenBank, Assession No. N29397.
Hillier et al., 1995, GenBank, Assession No. N49492.
Hillier et al., 1995, GenBank, Assession No. N23466.

(List continued on next page.)

*Primary Examiner*—James Martinell
*Attorney, Agent, or Firm*—Pennie & Edmonds LLP

[57] ABSTRACT

The present invention relates to utrons, RNA molecules which contain promoter regulatory motif(s) and DNA analogs thereof and DNA molecules that can be transcribed to produce the foregoing. In particular, the invention provides gene promoter suppressing nucleic acids which suppress transcription from a promoter of interest. In a preferred embodiment, the invention provides the TSU gene, nucleotide sequences of the TSU gene and RNA, as well as fragments, homologs and derivatives thereof. Methods of isolating TSU genes are also provided. Therapeutic and diagnostic methods and pharmaceutical compositions are also provided. In particular, the invention relates to methods for cell replacement therapy, gene therapy or organ transplantation wherein TSU nucleic acids suppress MHC class I and II gene expression, thus preventing immuno-rejection of non-autologous cells or organs. The invention also provides methods for treatment of diseases or disorders by suppression of MHC class I, MHC class II, ICAM-1, B7-1, B7-2, and/or FcγR expression by provision of TSU function.

77 Claims, 28 Drawing Sheets

OTHER PUBLICATIONS

Hillier et al., 1995, GenBank, Assession No. W32038.
Hillier et al., 1995, GenBank, Assession No. AA039604.
Hillier et al., 1995, GenBank, Assession No. W39338.
Hillier et al., 1995, GenBank, Assession No. W37893.
Hillier et al., 1995, GenBank, Assession No. AA045143.
Hillier et al., 1995, Image Consortium, Accession No. R38041.
Hillier et al., 1995, Image Consortium, Accession No. R71357.
Hillier et al., 1995, Image Consortium, Accession No. R31782.
Hillier et al., 1995, Image Consortium, Accession No. T61459.
Hillier et al., 1995, Image Consortium, Accession No. R22093.
Hou et al., 1994, Science 265:1701–1706.
Hunt and Orr, 1993, FASEB J. 6:2344–2348.
Ihle and Kerr, 1995, TIG 11(2):69–73.
Ihle, 1996, Cell 84:331–334.
Innis et al., 1990, *PCR Potocols: A Guide to Methods and Applications*. (Academic Press, San Diego, CA), pp. v–x.
Kanno et al., 1993, Mol. Cell. Biol. 13:3951–3963.
Kaye et al., 1991, Brit. J. Ophthalmol. 75:195–200.
Konishi et al., 1994, Biochem. Biophys. Res. Commun. 202(2):976–983.
Konishi et al., 1994, GenBank, Accession No. D29026.
Kriegler, 1990, *Gene Transfer and Expression. A Laboratory Manual*. (Stockton Press, NY), pp. vii–x.
Kuchroo et al., 1995, Cell 80:707–718.
Lanza et al., 1994, Transpl. Proc. 26(6):3346–3347.
Law et al., 1994, Transpl. Proc. 26(6):3381–3383.
Le Provost, 1993, GenBank, Accession No. X73800.
Le Bouteiller, 1994, Crit. Rev. Immunol. 14:1–41.
Lenschow et al., 1994, J. Immunol. 153:1990–1997.
Leung et al., 1996, Science 273:750–751.
Liew, 1996, GenBank, Accession No. N87548.
Loh et al., 1994, Mol. Cell. Biol. 14:2170–2179.
Loh et al., 1992, EMBO J. 11:1131–1140.
Majumder et al., 1993, EMBO J. 12:1131–1140.
Martin and Helenius, 1991, J. Virol. 65:232–244.
Matoba et al., 1994, Gene 146(2):199–207.
Matoba et al, 1994, GenBank, Accession No. D17151.
Matsuyama et al., 1995, Nucl. Acids Res. 23:2127–2136.
Matsuyama et al., 1993, Cell 75:83–97.
McKnight, 1980, Nucl. Acids Res. 8:5949–5964.
Medawar, 1953, Symp. Soc. Exp. Biol. 7:320–338.
Meraz et al., 1996, Cell 84:431–442.
Min et al., 1996, J. Immunol. 156:3174–3183.
Nickoloff and Turka, 1994, Immunol. Today 15:464–469.
Ohmori and Hamilton, 1993, J. Biol. Chem. 268:6677–6688.
Okubo et al., 1993, GenBank, Accession No. D20167.
Ono et al., 1991, J. Exp. Med. 173:629–637.
Peyman and Hammond, 1992, J. Immunol. 149:2675–2689.
Peyman et al., 1992, Transpl. Proc. 24(2):470–471.
Pierschbacher and Ruoslahti, 1984, Proc. Natl. Acad. Sci. USA 81:5985–5988.
Rastinejad and Blau, 1993, Cell 72:903–917.
Rastinejad et al., 1993, Cell 75:1107–1117.
Reis et al., 1994, EMBO J. 13:4798–4806.
Robertson et al., 1994, Crit. Rev. Immunol. 14:239–292.
Roby et al., 1994, Immunol. 83:444–448.
Sakatsume et al., 1995, J. Biol. Chem. 270:17528–17534.
Sambrook et al., 1989, *Molecular Cloning. A Laboratory Manual*. (Cold Spring Harbor Laboratory Press, Cold Spring Harbor, NY), pp. v–xxxviii.
Schmidt and Orr, 1993, Crit. Rev. Immunol. 13:207–224.
Seidel et al., 1995, Proc. Natl. Acad. Sci. USA 92:3041–3045.
Shimoda et al., 1996, Nature 380:630–633.
Shuai et al., 1993, Science 261:1744–1746.
Simonsen and Lodish, 1994, Trends in Pharmacol. Sci. 15:437–441.
Sligh et al., 1993, Proc. Natl. Acad. Sci. USA 90:8529–8533.
Smith et al., 1987, Amer. J. Physiol. 253(2 Pt 1), G99–109.
Soh et al., 1994, Cell 76:793–802.
Southern and Berg, 1982, J. Mol. Appl. Gen. 1:327–341.
Steimle et al., 1993, Cell 75:135–146.
Steimle et al., 1994, Science 265:106–109.
Stevens et al., 1994, GenBank, Accession No. T15746.
Takeda et al., 1996, Nature 380:627–630.
Thanos and Maniatis, 1995, Cell 80:529–532.
Vallejo and Pease, 1995, Immunol. Rev. 143:249–262.
Vasavada et al., 1990, Nucl. Acids Res. 18:3668.
Vitetta, 1994, J. Immunol. 153(4):1407–1420.
Wright et al., 1995, J. Exp. Med. 181:1459–1471.
Xu et al., 1996, Science 273:794–797.
Yamamoto et al., 1994, Mol. Cell. Biol. 14(7):4342–4349.
Yuan et al., 1994, Mol. Cell. Biol. 14(3):1657–1668.
Orkin et al, Report and Recommentdations of the Panel to Assess the NIH Investment in Research on Gene Therapy, Dec. 7, 1995.
Kolmer et al, Proc. Natl. Acad. Sci. USA 90: 8439 (1993).
Konishi et al, Biochem. Biophys. Res. Comm. 202: 976 (1994).
Wilson et al, Nature 368: 32 (1994).
Promega Catalog, 1993/1994, pp. 124–133.
Makai et al, Gene 132: 57 (1993).
Armstrong et al, Nature 308: 751 (1984).
Davidson et al, Curr. Genet. 14: 483 (1988).
Klippel et al, Molecular Cell. Biol. 14: 2675 (1994).
Notes by Dr. John Peyman dated Mar. 26, 1998 regarding elements in certain known genes.
Gray & Goedel, 1994, Genbank Accession No. V00536.
Johnson, 1991, Genbank Accession No. X57151.
Beck, 1997, Genbank Accession No. X66401, S57528.

```
                                                                             60
AAGCGGCGAGGTGCCTTTACTACATGTGTGATCTGAAAACCCTGCTTGGTTCTGAGCTGC

GAS COMPLEMENT                           IL-4-RE/ISRE
GTCTATTGAATTGGTAAAGTAATACCAATGGCTTTTTATCATTTCCTTCTTCCCTTTAAG   120

TTTCACTTGAAATTTTAAAAATCATGGTTATTTTTATCGTTGGGATCTTTCTGTCTTCTG   180

ISRE
GGTTCCATTTTTTAAATGTTTAAAAATATGTTGACATGGTAGTTCAGTTCTTAACCAATG   240

ACTTGGGGATGATGCAAACAATTACTGTCGTTGGGATTTAGAGTGTATTAGTCACGCATG   300

GAS COMPLEMENT               ISRE COMPLEMENT
TATGGGGAAGTAGTCTCGGGTATGCTGTTGTGAAATTGAAACTGTAAAAGTAGATGGTTG   360

GAS COMPLEMENT       GAS
AAAGTACTGGTATGTTGCTCTGTATGGTAAGAACTAATTCTGTTACGTCATGTACATAAT   420

IL-4-RE            GAS       POLY-A/ISRE
TACTAATCACTTTTCTTCCCCTTTACAGCACAAATAAAGTTTGAGTTCTAAACTCATTAA   480
A   481
```

FIG.5B

PSEUDOKNOT STRUCTURES

```
5'-AAGCGGCGAGGUGCCUUUACUACAUGUGUGAUCUGAAAACCCUGCUUGGUUCUGAGCUGC  60
            GAS COMPLEMENT                         IL-4-RE/ISRE
GUCUAUUGAAUUGGUAAAGUAAUACCAAUGGCUUUUUAUCAUUUCCUUCUUCCCUUUAAC   120

UUUCACUUGAAAUUUUAAAAAUCAUGGUUAUUUUUAUCGUUGGGAUCUUUCUGUCUUCUG   180
                                  ISRE
GGUUCCAUUUUUUAAAUGUUUAAAAAUAUGUUGACAUGGUAGUUCAGUUCUUAACCAAUG   240

ACUUGGGGAUGAUGCAAACAAUUACUGUCGUUGGGAUUUAGAGUGUAUUAGUCACGCAUG   300

GAS COMPLEMENT              ISRE COMPLEMENT
UAUGGGGAAGUAGUCUCGGGUAUGCUGUUGUGAAAUUGAAACUGUAAAAGUAGAUGGUUG   360

GAS COMPLEMENT        GAS
AAAGUACUGGUAUGUUGCUCUGUAUGGUAAGAACUAAUUCUGUUACGUCAUGUACAUAAU   420

IL-4-RE              GAS      POLY-A/ISRE
UACUAAUCACUUUCUUCCCCUUUACAGCACAAAUAAAGUUUGAGUUCUAAACUCAUUAA    480
A-3' 481
```

FIG.16

REGULATION OF GENE EXPRESSION

1. FIELD OF THE INVENTION

The invention relates to nucleic acid molecules that suppress or enhance gene expression, cDNAs that encode such molecules, and related therapeutic and diagnostic compositions and methods. In particular, the invention relates to single-stranded nucleic acid molecules containing an array of promoter motifs, which molecules suppress gene expression from promoters containing those promoter motifs, cDNAs that encode such molecules, and related therapeutic and diagnostic compositions and methods. A specific embodiment of the present invention relates to TSU genes, their encoded RNAs, as well as derivatives, analogs, and fragments thereof, that suppress expression of MHC class I and II antigens and ICAM-1, B7-1, B7-2 and FcγR antigens. The invention further relates to methods of therapy and diagnosis and therapeutic compositions using TSU nucleic acids to suppress MHC class I and II antigen and ICAM-1, B7-1, B7-2 and FcγR antigen expression.

2. BACKGROUND OF THE INVENTION

Control of gene expression underlies, at some level, all cellular and/or organismal processes, including direction of the development of the organism and cellular responses to outside signals. Gene control occurs at several points in the cellular response, including the activation or suppression of transcription, the differential processing and stabilization of messenger RNA (mRNA), and the extent of translation of the mRNA. Control of transcription plays a particularly critical role in the regulation of gene expression in eukaryotic cells. (See generally, Darnell et al., 1990, *Molecular Cell Biology*, 2d ed., Chapter 11, W.H. Freeman & Co., NY, pp. 391–448).

Cellular mechanisms mediate the activation of transcription of specific genes, for example, the activation of transcription elicited during development and that elicited by extracellular signals such as hormones or growth factors. In particular, transcription of a specific mRNA coding for a particular gene product is controlled by a set of transcription factor proteins. These proteins bind specific DNA sequences, either promoter or enhancer elements, and form multimeric complexes which activate transcription (Tjian and Maniatis, 1994, *Cell* 77:5–8). The multitude and cell specificity of the transcription factors and corresponding DNA binding sites allow for the precise regulation of transcription. Thus, the regulation of transcription activation would provide a precise and specific method for controlling the production of particular proteins.

Previous work has suggested that the presence of the 3' untranslated region (UTR) of a certain mRNA may affect the transcription of a select gene or group of genes. Rastinejad and Blau (1993, *Cell* 72:903–917) showed that the 3' UTRs of the muscle structural genes, troponin, tropomyosin, and α-cardiac actin-enhanced muscle-specific gene expression. The authors suggest, among a variety of potential mechanisms, that the RNA sequences play a role in the transcriptional activation of these genes.

Other work has suggested that the clustering of promoter sequences within and around genes may assist in the recruitment of required transcription factors to the vicinity of active promoter elements in the interphase nucleus (Bodnar and Ward, 1987, *Nucleic Acids Research* 15:1835–51). Thus, it appears that these sequences may act to specifically concentrate these factors so that the factors are available to activate transcription quickly at the appropriate point in the cell cycle.

While activation of transcription has been studied intensely, gene control through the suppression or inhibition of transcription has not. Thus, although most genes are repressed in most all types, little is known about the mechanisms that comprise selective gene repression during embryogenesis, organogenesis and differentiation (Herschbach and Johnson, 1993, *Ann. Rev. Cell Biol.* 9:479–509).

2.1. REGULATION OF MHC GENE EXPRESSION

One example where gene suppression has been hypothesized to play a critical role is the paradoxical survival of a semi-allogeneic fetus in the presence of the maternal immune system in vertebrates (Medawar, 1953, *Symp. Soc. Exp. Biol.* 7:320–328). Today, the mechanisms causing intraspecies tissue graft rejection in the absence of immunosuppressive drugs are known at the cellular and molecular level, but the protective mechanisms in the placenta are still not clear. The major histocompatibility complex (MHC) is a region of the chromosome containing the HLA or MHC genes which are divided into three categories: class I, class II and class III. In humans, the MHC class I genes include HLA-A, HLA-B and HLA-C and the MHC class II genes include HLA-DP, HLA-DQ and HLA-DR (Golub and Green, 1991, *Immunology: A Synthesis*, Second Edition, Chapter 15.) MHC class I and class II molecules bind peptide fragments of self- or foreign antigens and are inspected on the cell surface by T lymphocytes and, thus, can stimulate cellular or humoral immune attack (Germain, 1994, *Cell* 76:287–299). Although efficient proteolytic processing and presentation of antigens and high levels of MHC class II gene products are the hallmark of the professional antigen-presenting cells of the immune system, cells in other tissues can be stimulated by cytokines such as interferon-γ (IFN-γ) to increase expression of MHC class II genes (Glimcher and Kara, 1992, *Annu. Rev. Immunol.* 10:13–49). MHC class I genes are expressed ubiquitously and can be up-regulated by cytokine stimulation as well.

Trophoblasts are exceptional in their lack of constitutive expression of polymorphic MHC class I antigens and their lack of IFN-γ stimulation of MHC class I or II gene expression. The absence of these immune target molecules on trophoblasts in the normal human placenta is thought to be a critical factor in maternal tolerance of the feto-placental unit. Syncytiotrophoblast covering the chorionic villi forms not only a large transport surface for efficient gas, nutrient and waste product exchange between the maternal and the fetal blood supply, but also a mechanical barrier that excludes maternal blood cells from the fetal circulation (Hunt and Orr, 1992, *FASEB J.* 6:2344–48; Cross et al., 1994, *Science* 266:1508–18; Wood, 1994, *Immunol. Today* 15:15–18).

The mechanism of IFN-γ-induced MHC gene expression has been elucidated by numerous studies of the molecules involved, including the subunits of the IFN-γ receptor (Aguet et al., 1988, *Cell* 55:273–280; Hemmi et al., 1994, *Cell* 76:803–10; Soh et al., 1994, *Cell* 76:793–802), Jak kinases and the STAT transcription factors (Darnell et al., 1994, *Science* 264:1415–20), the interferon stimulated response elements (ISRE) conserved in MHC class I (Vallejo and Pease, 1995, *Immunol. Rev.* 143:249–262; Le Bouteiller, 1994, *Crit. Rev. Immunol.* 14:89–129) and other genes, and the gamma-interferon activation site (GAS) elements conserved in other IFN-γ-responsive genes (Darnell et al., 1994, *Science* 264:1415–20) such as ICAM-1, B7-1, B7-2 and FcγR genes. The following cellular events have been established in the Jak-STAT pathway of IFN-γ signaling. Jak1 binds to the cytoplasmic domain of the IFN-γ receptor α-subunit. Binding of IFN-γ dimer to the extracellular domain of the dimerized α-subunit leads to association with IFN-γ receptor β-subunits and binding of Jak2 to the cytoplasmic domain of the β-subunit. Phosphorylation of tyrosine residues by Jak1 and Jak2 on the kinases and the receptor α-subunits stimulates recruitment of STAT1 to the receptor (Kotenko et al., 1995, *J. Biol. Chem.* 270:20915–921; Sakatsume et al., 1995, *J. Biol. Chem.* 270:17528–534). Phosphorylation of STAT1 on tyrosine causes dimerization and transport to the nucleus (Shuai et al., 1993, *Science* 261:1744–46; Greenlund et al., 1995, *Immunity* 2:677–687) for trans-activation of IFN-γ-responsive genes. Expression of MHC class I genes is induced by STAT1-containing transcription factors that bind ISRE sequences and can be enhanced by tumor necrosis factor-α-mediated activation of NF-κB transcription factors that bind neighboring κB sites (Thanos and Maniatis, 1995, *Cell* 80:529–32). Stimulation of MHC class II gene expression by IFN-γ is initiated by Jak-STAT activation, but also requires the de novo production of the CIITA factor (Steimle et al., 1993, *Cell* 75:135–146; Steimle et al., 1994, *Science* 265:106–109; Chang et al., 1994, *J. Exp. Med.* 180:1367–74) which interacts with constitutively expressed DNA-binding proteins on conserved promoter sequences in MHC class II genes (Glimcher and Kara, 1992, *Annu. Rev. Immunol.* 10:13–49). Jak-STAT activation has also been implicated in activation of gene transcription by other cytokines such as interferon-α, interferon-β, granulocyte colony stimulating factor, epidermal growth factor, growth hormone, ciliary neurotrophic factor, prolactin, leukemia inhibitory factor, interleukin-2, interleukin-3, interleukin-4, interleukin-5, interleukin-6, interleukin-8, interleukin-10, interleukin-13, and interleukin-15. (Ihle and Kerr, 1995, *Trends in Genetics* 11:69–73; Darnell et al., 1994, *Science* 264:1415–20.)

It was previously shown by in situ hybridization on first-trimester placenta and by Northern blot analysis of the trophoblast cell line Jar that IFN-γ-responsive MHC class II gene expression is blocked at the RNA level by an intracellular mechanism (Peyman and Hammond, 1992, *J. Immunol.* 149:2675–80). Mammalian expression cloning has been applied successfully to the cloning of cDNAs and genes encoding a number of cell surface antigens, receptors, transporters, and other intracellular proteins (Simonsen and Lodish, 1994, *Trends in Pharmacol. Sci.* 15:437–441). The cDNA encoding the CIITA transcription factor was cloned by functional complementation of the recessive MHC class II⁻-phenotype in a cell line derived from a patient with bare lymphocyte syndrome (Steimle et al., 1993, *Cell* 75:135–146).

However, until the present invention, the agent responsible for blocking IFN-γ responsive MHC gene expression in trophoblasts has remained unidentified and unisolated.

Presently, donor organs for transplants are scarce and many patients die for lack of compatible donor organs. Even when compatible organs are found, patients suffer side effects from the necessary immunosuppressive therapies, and organ rejection often occurs in spite of immunosuppressive measures. Thus, there is tremendous need for methods to suppress MHC and other antigen expression on donor organs to prevent rejection mediated by the cellular immune response and to obviate the need for immunosuppressive drugs. There is also a need for methods of preparing and using non-human animal organs for transplants to increase the presently sparse supply.

It is a goal of the present invention to provide agents which suppress gene expression of a gene promoter of interest, which has great value in the suppression of expression of gene products which lead to disease and disorder (e.g., gene products of pathogenic organisms, endogenous gene products mediating disease symptoms). It is also a goal of the present invention to solve the shortage of organ transplants by providing an agent which suppresses MHC class I and class II gene expression and expression of other cytokine-induced antigens involved in the immune response, such as ICAM-1, B7-1, B7-2 and FcγR, and methods for preventing cell-mediated rejection of both allogeneic and xenogeneic organ and cell transplants.

Citation of references in Section 2 or any other section of this application shall not be construed as an admission that such references are prior art to the present invention.

3. SUMMARY OF THE INVENTION

The present invention relates to utron nucleic acids, i.e., nucleic acids from or homologous to the 3'-untranslated region (UTR) of an mRNA with activity in vivo, that stimulate or inhibit a cellular process by sequence-specific interaction with an aspect of the cellular machinery. The present invention further relates to nucleic acids that suppress a gene promoter of interest. In particular, such nucleic acids are RNA molecules, or the DNA molecules that encode them, comprised of the appropriate structural and functional components and the desired promoter regulatory motifs, as described hereinbelow. The invention also provides for functionally active fragments and derivatives of these gene promoter suppressing fragments, as well as a nucleic acid comprising a promoter operably linked to a nucleic acid that can be transcribed to produce a gene promoter-suppressing RNA.

In a preferred embodiment, the present invention provides nucleotide sequences of the trophoblast STAT utron, or TSU, gene, as well as fragments and other derivatives of the TSU nucleic acids. TSU is a nucleic acid provided by the present invention, identified by a method of the invention, which is able to suppress constitutive and IFN-γ-induced MHC class I and II antigen expression and expression of other antigens, the gene promoters of which contain related sequence motifs that are stimulated by the same factors which stimulate MHC class I and II antigen expression. Methods of identifying and isolating the TSU gene are provided.

The invention also relates to TSU derivatives and homologs which are functionally active, i.e., they have the ability to suppress MHC class I and/or II expression as well as ICAM-1, B7-1, B7-2 and FcγR expression. In a preferred embodiment, the fragment includes or consists of one or more ISRE, GAS or IL-4-RE conserved promoter motifs or another motif of a promoter desired to be suppressed. TSU nucleic acids, including TSU DNA, RNA, fragments, and other derivatives are also provided. Also provided is a nucleic acid comprising or consisting essentially of a promoter operably linked to a sequence that can be transcribed to produce an TSU RNA or functionally active fragment or derivative thereof.

Methods for assaying gene promoter suppressing, and in particular TSU, function are additionally provided.

The present invention also relates to therapeutic methods and compositions based on gene promoter suppressing, preferably TSU, nucleic acids as taught by the invention. Therapeutic methods involving cell replacement therapy and gene therapy are also described. In particular, the invention relates to methods of use in organ transplantation, treatment of immune disorders, prevention of fetal rejection, and treatment of diseases or disorders caused by viruses, by eukaryotic pathogens or pests, or by prokaryotic pathogens.

The invention also provides for pharmaceutical compositions and methods of administration. Therapeutic compounds include, but are not limited to, gene promoter suppressing nucleic acids and fragments and derivatives thereof, and recombinant replacement cells and tissues.

The invention also provides diagnostic methods using the nucleic acids of the invention, which methods can be used to detect or monitor conditions, disorders, or disease states associated with gene promoter suppressing nucleic acid expression or activity.

4. BRIEF DESCRIPTION OF THE FIGURES

FIGS. 1A–D. Growth curves of cells untransfected and transfected with MHC class II promoter-TK construct. Untransfected HeLa clone 6 cells (A) and untransfected Jar cells (C) survived all conditions. All cells survived ganciclovir treatment alone (A–D, open symbols). Cells expressing TK were killed by ganciclovir treatment. IFN-γ induced the toxic phenotype in the HeLa transfectant clone Al (B, solid symbols) and two others (not shown), but not in the Jar transfectant clone 3D1 (D, solid symbols) and four others (not shown). In all FIGS. 1A–D, both open and solid circles represent treatment with 0 nM ganciclovir, open and solid squares represent treatment with 50 nM ganciclovir, open and solid triangles represent treatment with 150 nM ganciclovir and the open and solid inverted triangles represent treatment with 250 nM ganciclovir. Open symbols: without IFN-γ; solid symbols: with 200 U/ml IFN-γ.

Figure 2:
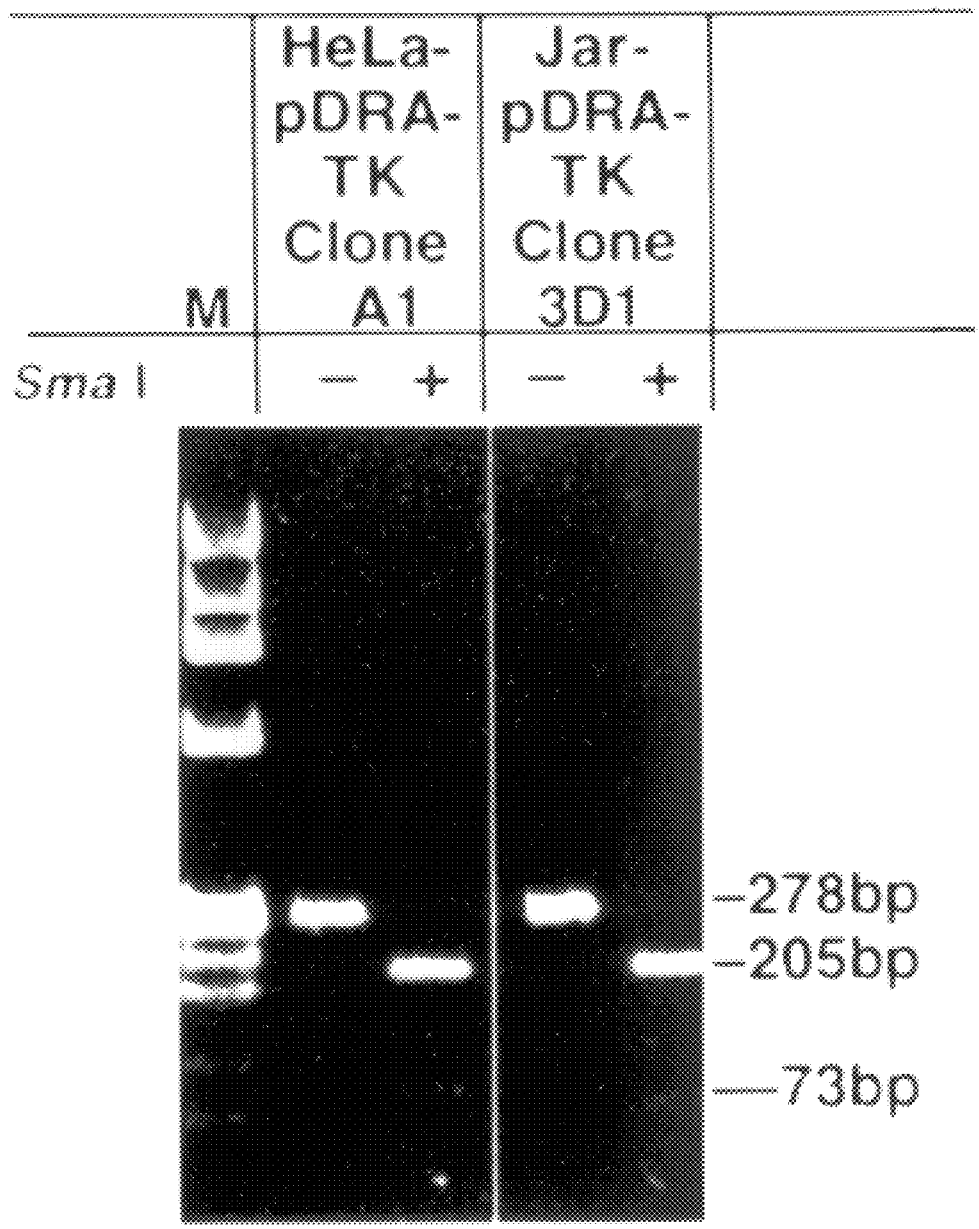

FIG. 2. Detection of integrated TK gene in expressing and non-expressing transfectant clones. Genomic DNA from HeLa-pDRA-TK clone A1, and from Jar-pDRA-TK clone 3D1 was analyzed by PCR using primers flanking a TK gene fragment of 278 bp. Identity of this band was confirmed by Sma I digestion to form 205 bp and 73 bp cleavage products. The two other HeLa and four other Jar transfectant clones studied similarly had the integrated TK gene.

FIGS. 3A–G. Flow cytometric analysis of Raji×HeLa transient heterokaryons. HeLa cells were pre-stained with 5-and 6-carboxyfluorescein diacetate succinimidyl ester (CFSE) (B–G). Raji and Hela cells were cultured (C,E,G) or fused with polyethylene glycol and cultured (D,F,G). Two days later the cell mixtures were double-labeled with L243 mAb (C,D,G) or non-immune mouse $IgG_{2a}$ (E,F) and R-phycoerythrin goat-anti-mouse Ab. Gating was set for L243-stained Raji in A and for CFSE-labeled HeLa cells in B. The right quadrants with co-culture (C) and fusion (D) data were replotted in G to highlight similarity of L243 labeling profiles.

FIGS. 4A–G. Flow cytometric analysis of Raji×Jar transient heterokaryons. Jar cells were pre-stained with CFSE (B–G). Raji and Jar cells were cultured (C,E,G) or fused with polyethylene glycol and cultured (D,F,G). Two days later the cell mixtures were double-labeled with L243 mAb (C,D,G) or non-immune mouse $IgG_{2a}$ (E,F) and R-phycoerythrin goat-anti-mouse Ab. Gating was set for L243-stained Raji in A and for CFSE-labeled Jar cells in B. The right quadrants with co-culture (C) and fusion (D) data were replotted in G to highlight difference in L243 labeling profiles.

Figure 5A:
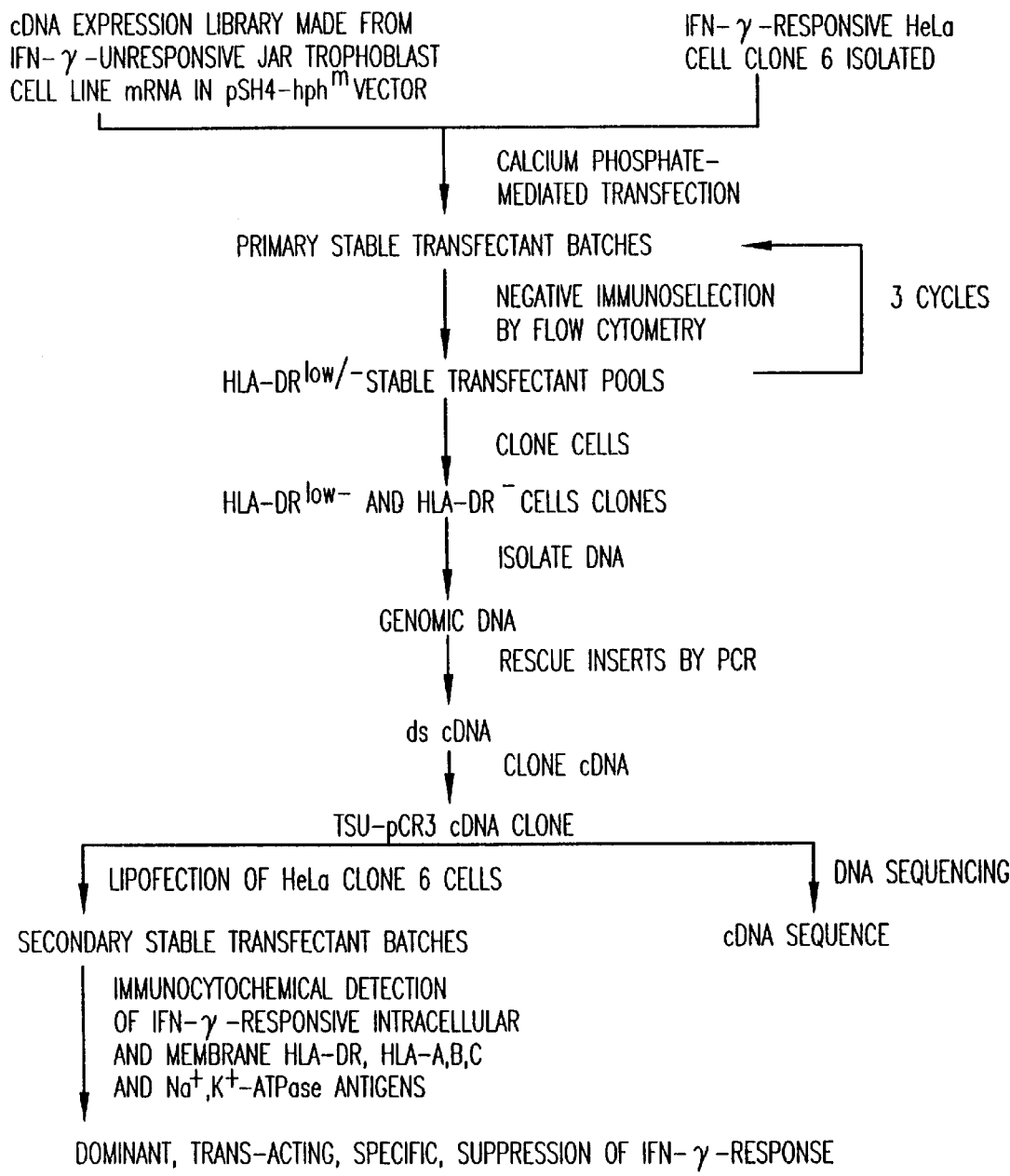

FIGS. 5A and B. Expression cloning of trophoblast MHC silencer TSU. (A) Schematic diagram of cloning method. (B) Sequence of TSU cDNA (SEQ ID NO:1). Gene promoter motifs and the poly-A addition signal are shown in bold letters.

Figure 6:
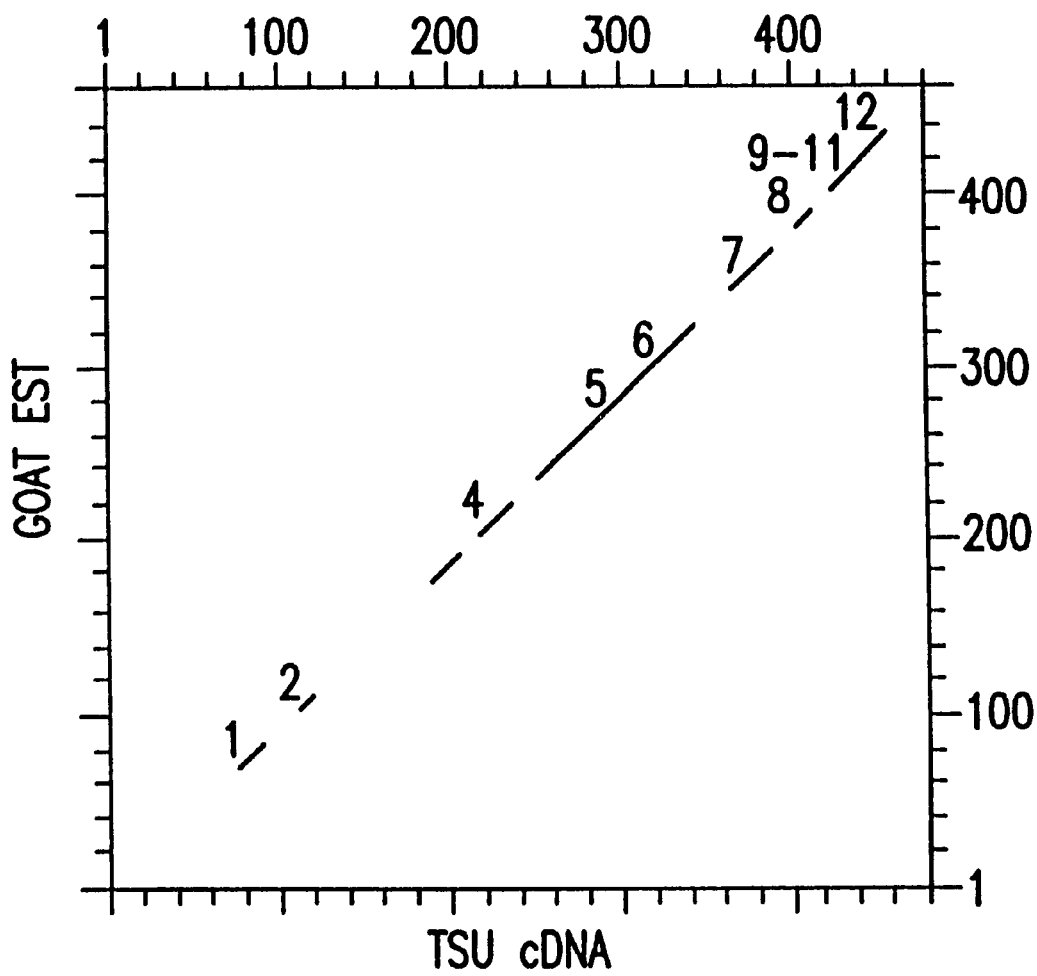

FIG. 6. Comparison of human TSU cDNA and goat TSU-related EST. (A) Dot-plot analysis shows short regions conserved in each CDNA. Numbers 1–12 refer to the location of promoter motifs and poly-A signal, listed in Table 1. (B) Expressed gene promoter motifs in TSU and the goat EST.

Figure 7A:
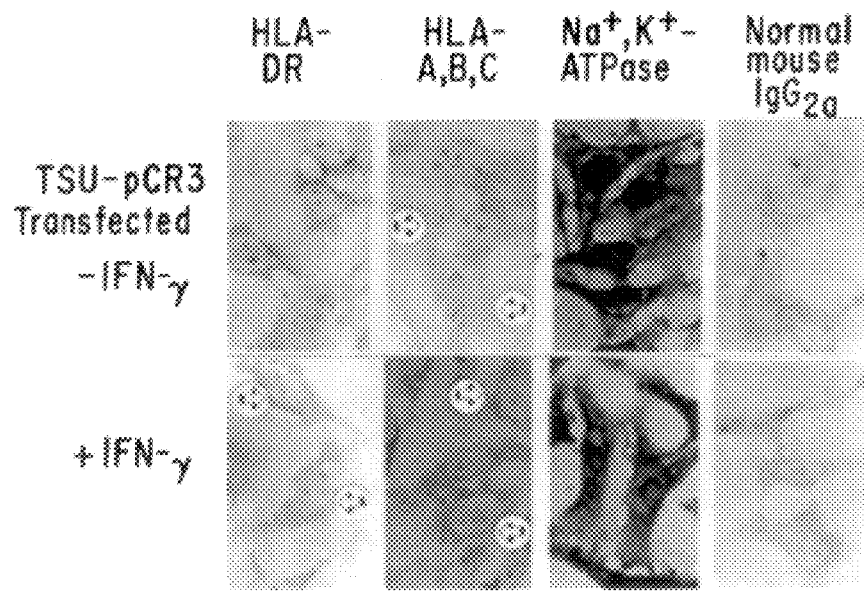
Figure 7B:
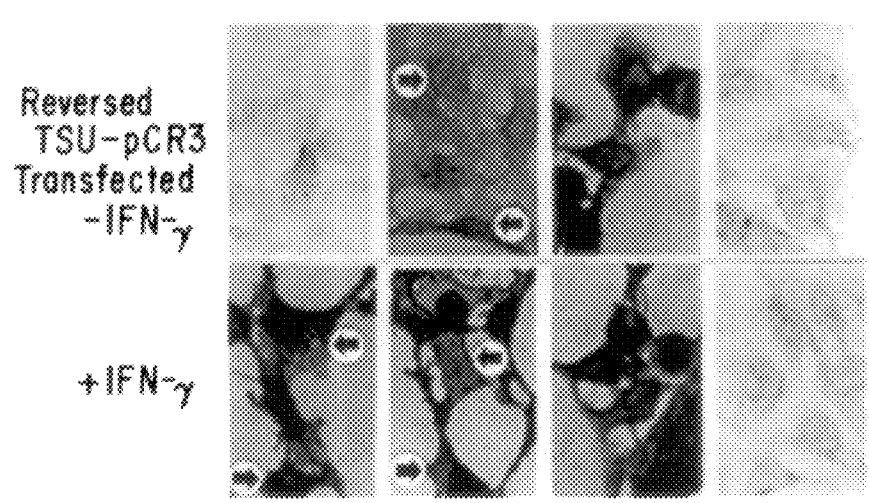
Figure 7C:
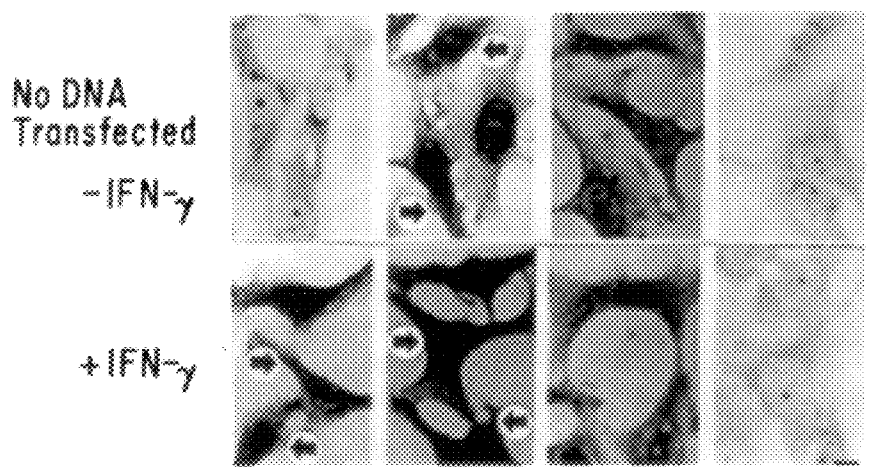

FIGS. 7A–C. Function of TSU RNA in transfected HeLa cells. DNA was introduced into HeLa clone 6 cells by lipofection, and stable transfectant batches were studied after 16 days of G418 selection by treatment for 2 days with 200 U/ml IFN-γ, acetone-fixation, and staining for intracellular and membrane antigens with the monoclonal antibodies described in Experimental Procedures. Antibody binding was detected with a biotinylated horse-anti-mouse secondary antibody, and avidin-biotinylated peroxidase complex. The peroxidase was visualized with hydrogen peroxide-diaminobenzidine-$Ni^{++}$ substrate. (A) Cells transfected with TSU-pCR3 expression construct. (B) Cells transfected with the reversed TSU-pCR3 construct. (C) Untransfected HeLa clone 6 cells. Results represent two separate transfections and analyses. Open arrows, background level of antigen; solid arrows, positive antigen expression. Scale bar, 10 μm.

Figure 8A:
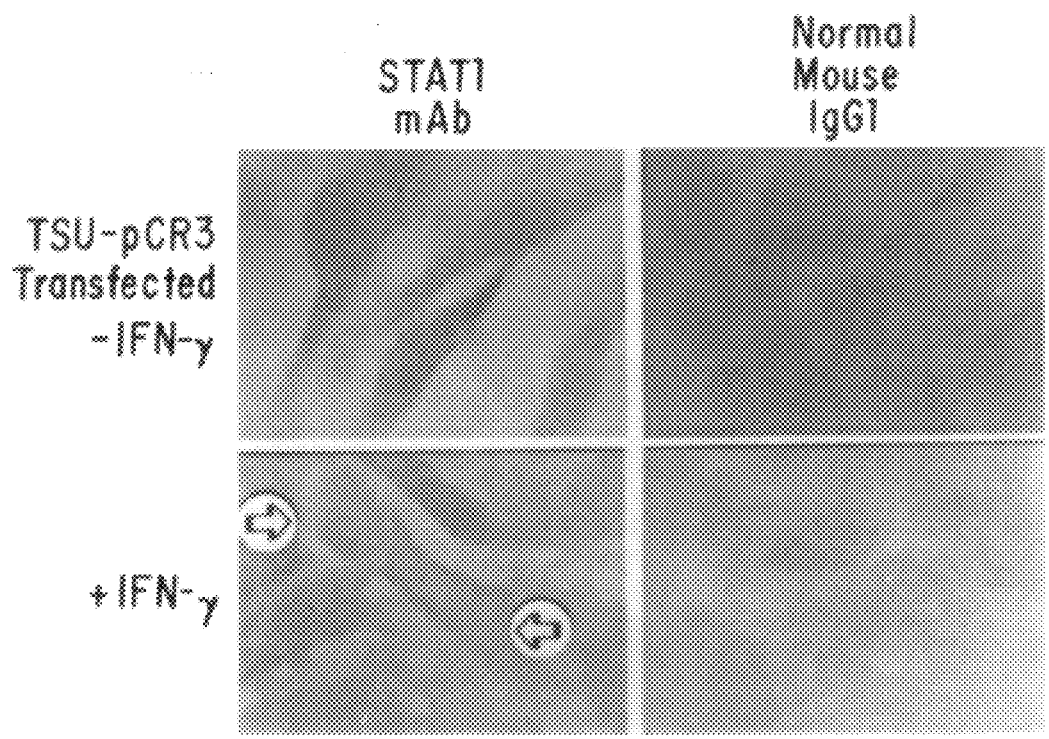
Figure 8B:
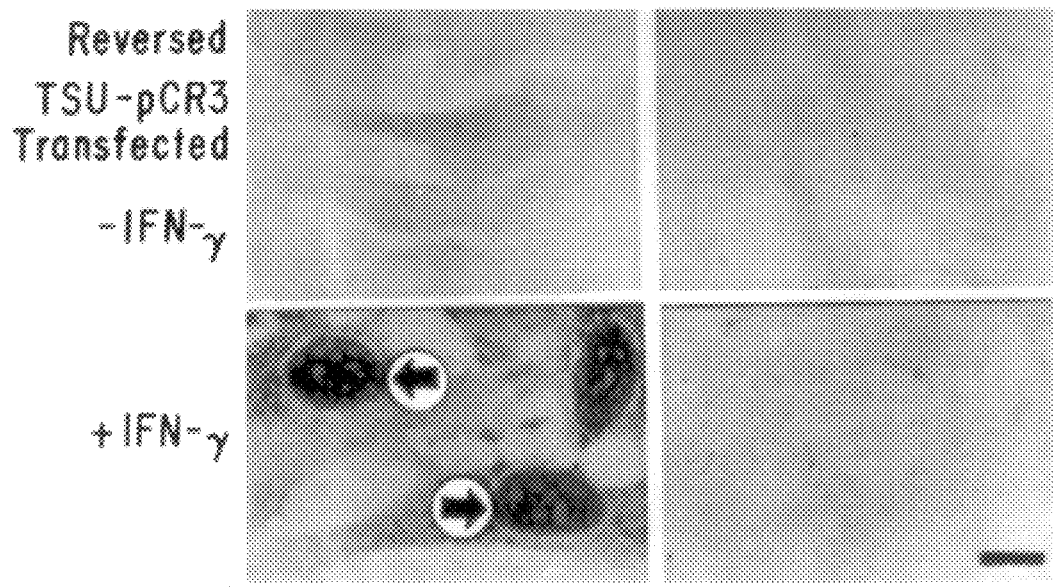

FIGS. 8A and B. STAT1 localization in HeLa cells expressing sense and antisense TSU RNA. Batches of stable transfectants were prepared as in FIGS. 7A–C, treated with IFN-γ for 2 days, fixed with acetone, and stained for cytoplasmic and nuclear STAT1 antigen by avidin-biotin-peroxidase immunocytochemistry. Two separate experiments gave identical results. Open arrows, cytoplasmic STAT1; solid arrows, nuclear STAT1. Scale bar, 10 μm.

Figure 9A:
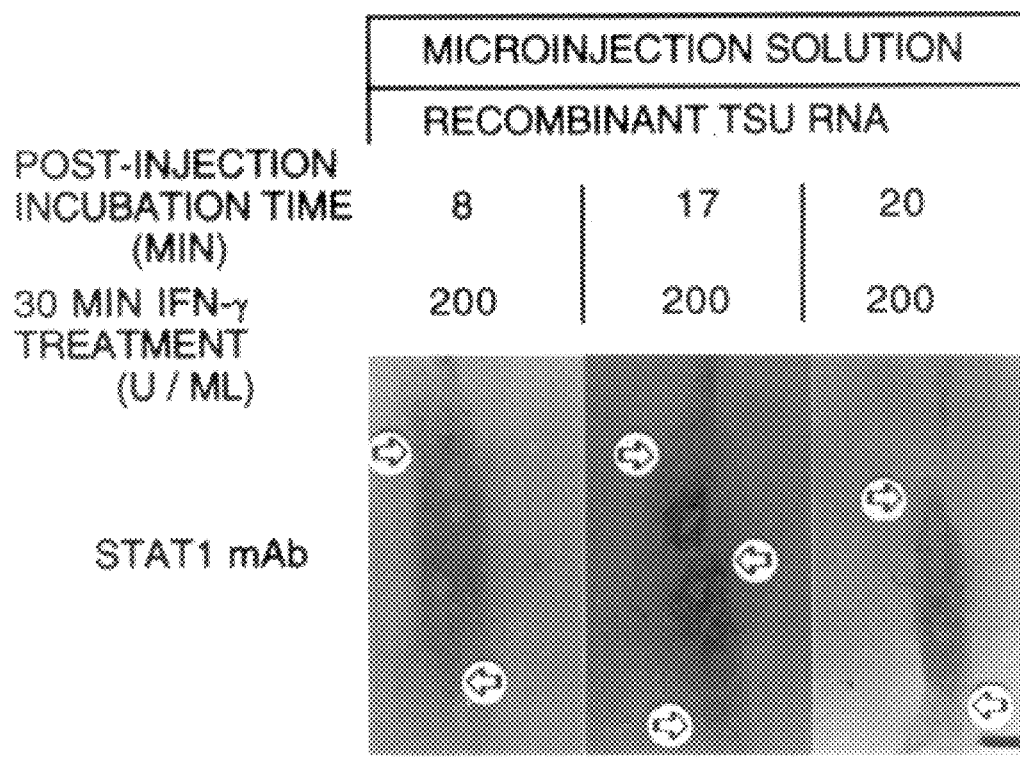
Figure 9B:
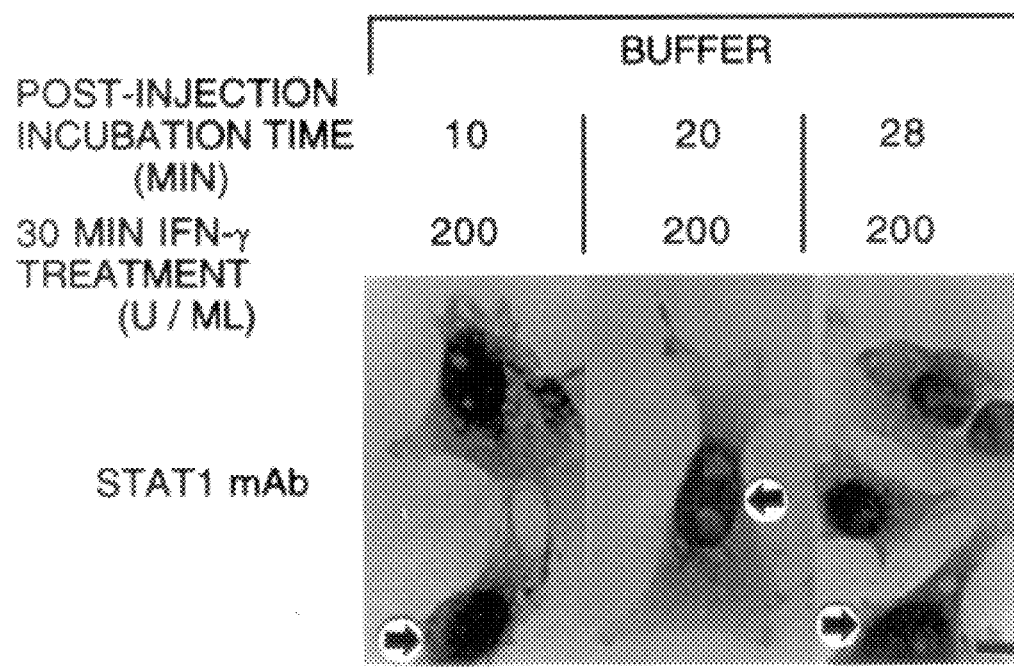

FIGS. 9A and B. Function of TSU RNA in microinjected HeLa cells. Cells grown on coverslips were individually identified by phase-contrast optics, bathed in HEPES-buffered medium, and microinjected at 25° C. for short-term incubations as shown. IFN-γ (200 U/ml) was added to the medium, and the cells were incubated at 37° C. for 30 min before acetone fixation and immunocytochemistry for STAT1 antigen as in FIGS. 8A and B. Several dozen cells were successfully microinjected over 4 independent experiments. (A) Recombinant TSU RNA at 1 mg/ml was microinjected into these 3 groups of cells. (B) Control cells, one marked with an arrow in each panel, were injected with buffer alone. Open arrows, cytoplasmic STAT1; solid arrows, nuclear STAT1. Scale bar, 10 μm.

Figure 10:
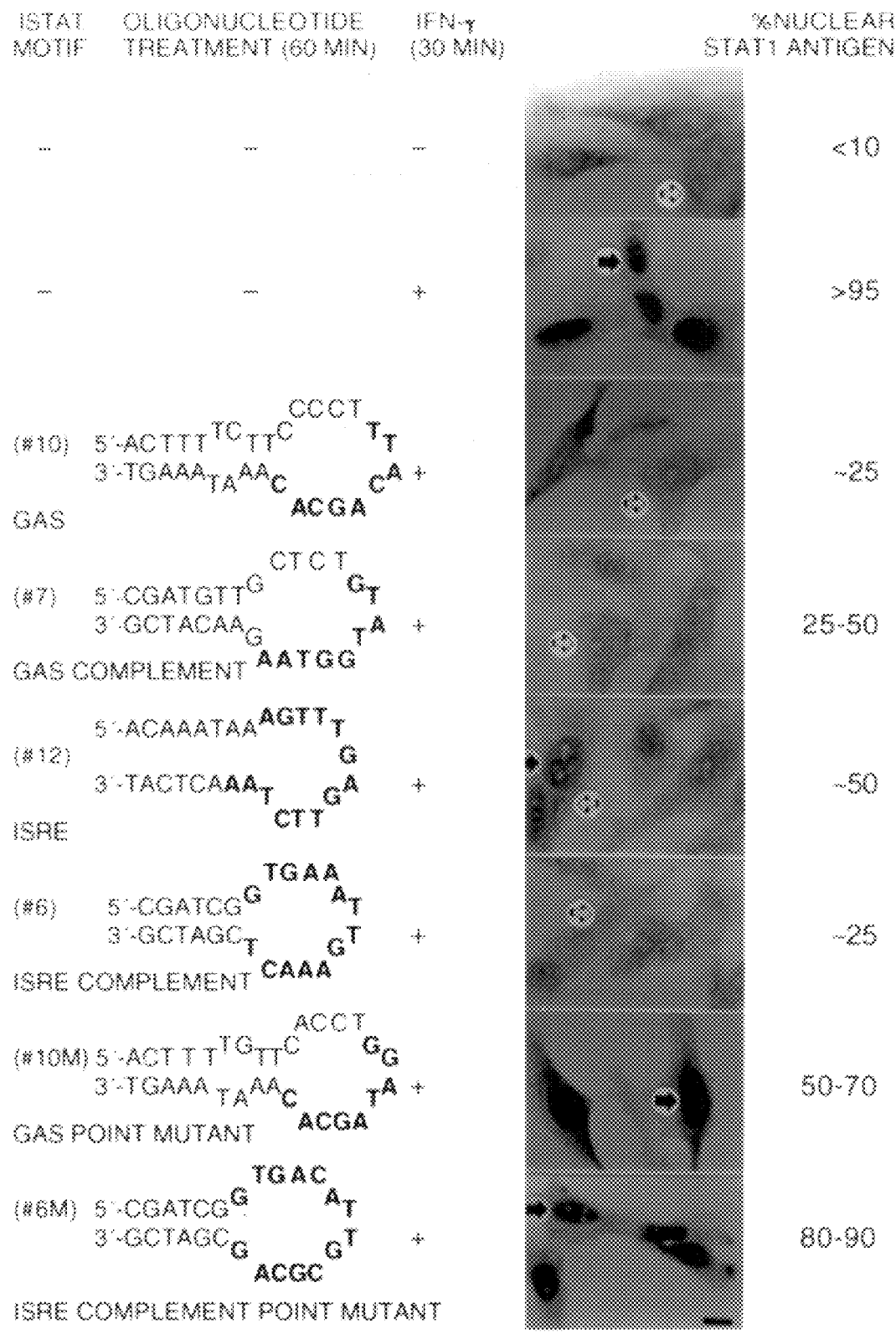

FIG. 10. Function of single-stranded oligodeoxynucleotide models of TSU promoter motifs in HeLa cells. HeLa cells were treated with 10 μM phosphorothioate oligonucleotide in tissue culture medium for 60 min, then 200 U/ml IFN-γ was added for 30 min. Cells were acetone-fixed and stained for STAT1 antigen as in FIGS. 8A and B. Representative results are shown based on the following number of independent preparations and analyses: GAS, n=3; GAS complement, n=2; ISRE, n=3; ISRE complement, n=3; GAS point mutant, n=1; ISRE point mutant, n=1; no oligonucleotide, n=12. Open arrows, cytoplasmic STAT1; solid arrows, nuclear STAT1. Scale bar, 10 μm.

Figure 11:
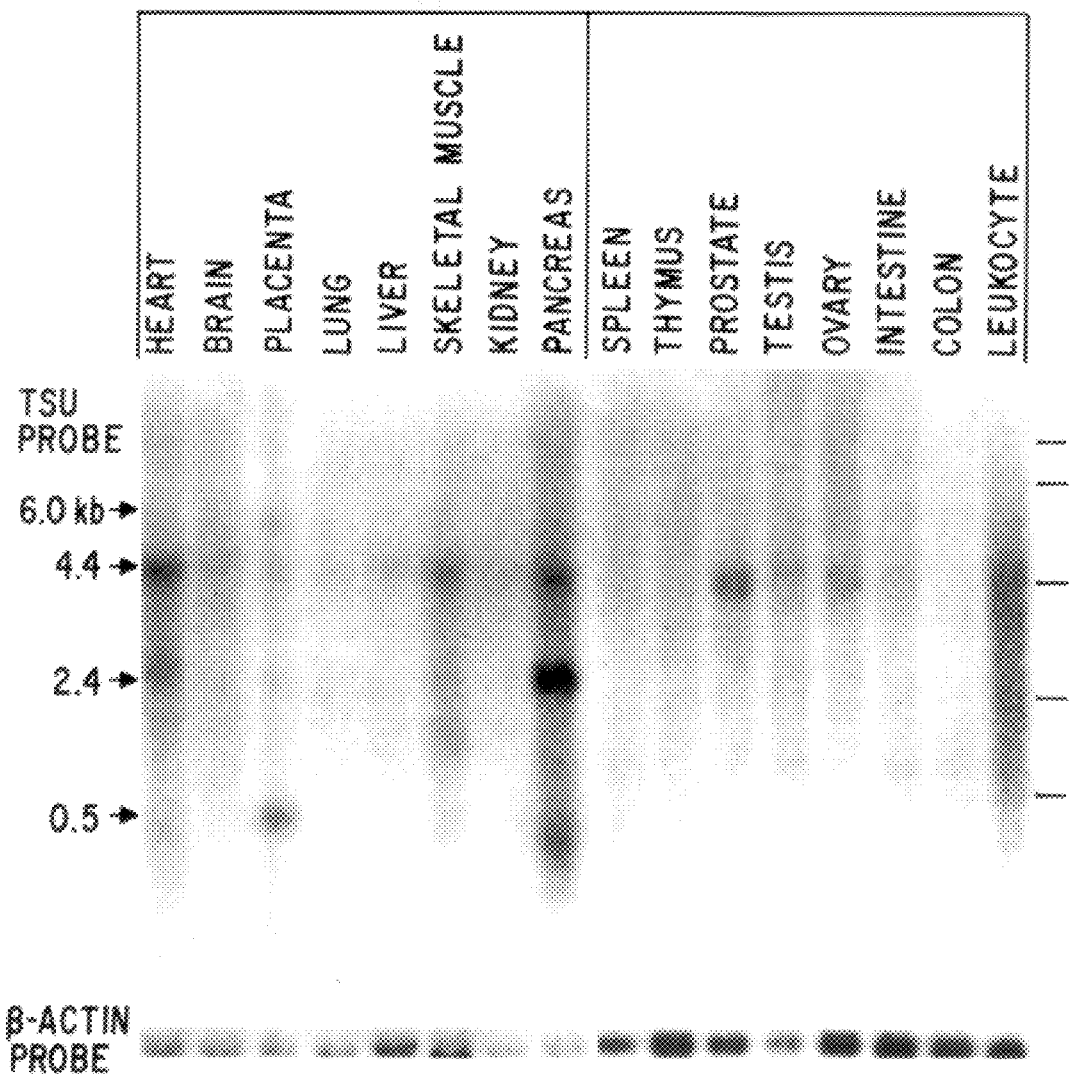

FIG. 11. Northern blot analysis of expression of TSU RNA in placenta, and reactivation of STAT1 function by treatment of trophoblasts with TSU antisense oligonucleotide. Poly-$A^+$ RNA (2 μg) from 16 normal human tissues was analyzed by probing Northern blots with a $^{32}$P-labeled TSU antisense RNA probe, as described infra Section 7.1.6. Autoradiographic exposure shown was produced by exposure with an intensifying screen for 8 days. Results represent two independent experiments.

FIGS. 12A–D. Graphic representation and size specifications of the structural RNA components which can contain the functional promoter regulatory motifs in the nucleic acids of the invention. (A) Graphic representation of and the specifications for the different elements (identified as a, b, c, d, j and functional motif) of the stem-loop structure. (B) Representation and the specifications for the different elements (identified as e, f, g, h, i, j and functional motif) of the hairpin structure. (C) Representation and the specifications for the different elements (identified as k, l, m, n, p, q, r, j and functional motif) of the bulge structure. (D) Representation of one form of pseudoknot structure. In all FIGS. 12A–D, functional promoter regulatory motifs are indicated by cross-hatched boxes and base-paired regions are indicated by dots between parallel lines.

Figure 13A:
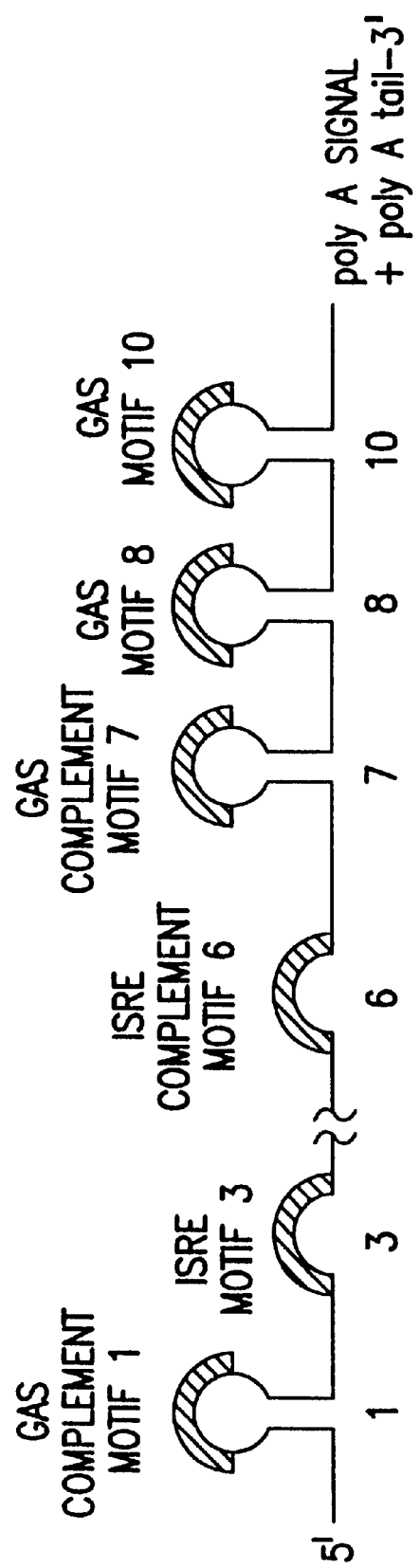

FIGS. 13A and B. Graphic representation of the TSU RNA structure. (A) The three pairs of complementary promoter elements are identified by cross-hatched boxes. (B) A predicted tertiary structure for the TSU RNA, formed by intramolecular base-pair formation between promoter motifs.

Figure 14A:
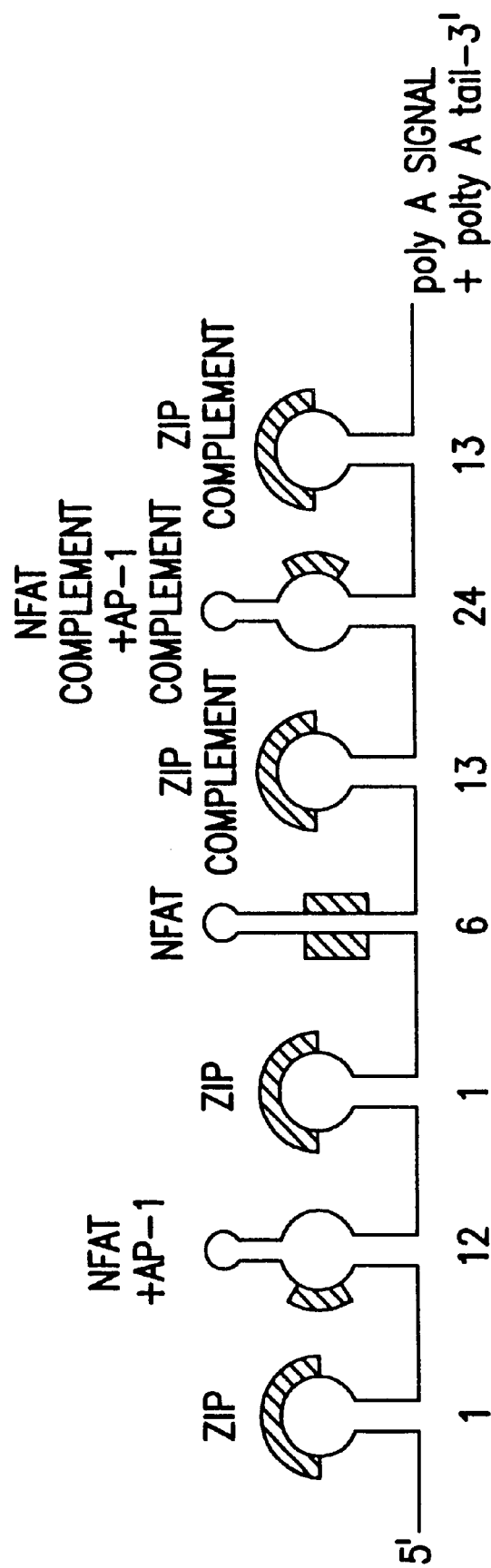

FIGS. 14A and B. Graphic depiction of the synthetic IL-2 repressor utron. (A) Graphic depiction of the predicted folding pattern of the synthetic composite IL-2 repressor utron where component 1 is a stem-loop structure containing the ZIP 8 base motif (5'-CCCCACCC-3'), component 13 is a stem-loop structure containing the ZIP 8 base complement, component 6 is a hairpin structure containing the NF-AT 6 base motif (5'-GGAAAA-3'), component 12 is a bulge structure containing the NF-AT motif and the AP-1 6 base motif (5'-TGTTTCA-3') separated by a 2 base spacer (5'-AC-3'), component 24 is a bulge structure with the NF-AT and AP-1 motifs. (B) Predicted folding pattern of the synthetic IL-2 repressor utron designed to fold into a more compact structure containing two loop-loop structures and one bulge-bulge structure. For both FIGS. 14A and B, the functional RNA motifs are represented by the cross-hatched box.

Figure 15A:
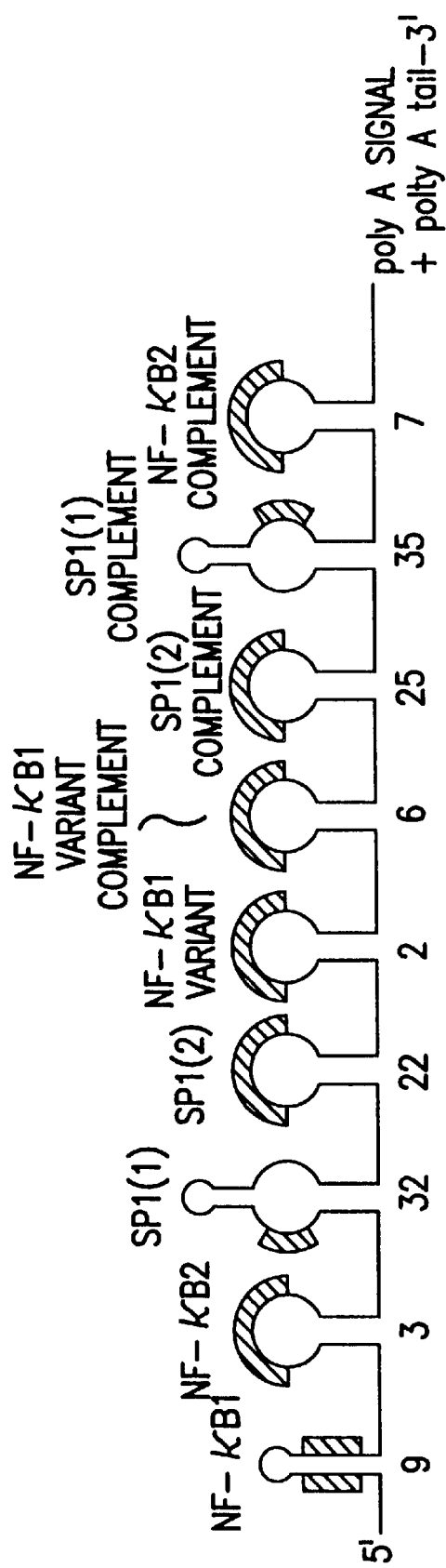
Figure 15B:
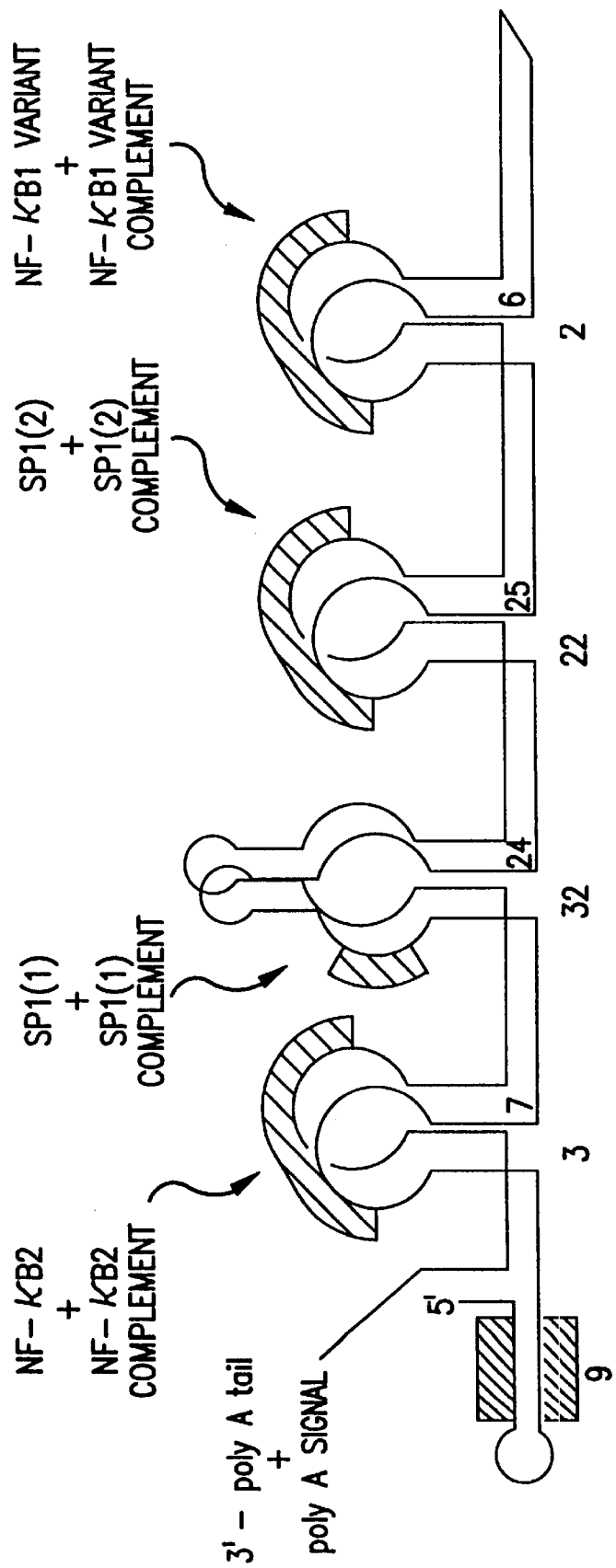

FIGS. 15A–B. Graphic representations of the HIV-1 LTR repressor utron structure. (A) The predicted folding pattern of the synthetic composite HIV-1 LTR repressor utron where component 6 is a stem-loop structure containing the 13 base NF-κB non-palindromic variant sequence complement (5'-CCGTAAAGTCCCTA-3') (SEQ ID NO:14), where component 9 is a hairpin structure containing the 13 base pair NF-κB1 motif (5'-AGGGACTTTCCGG-3') (SEQ ID NO:15), where component 3 is a stem-loop structure containing the NF-κB2 motif (5'-TGGGGACTTTCCA-3') (SEQ ID NO:16), where component 7 is a stem-loop structure containing an NF-κB2 complement motif (5'-TTGAAAGTCCCCATGA-3') (SEQ ID NO:17), where component 22 is a stem-loop containing the SP1(2) motif (5'-TGGGCGGAC-3'), where component 26 is a stem-loop containing the SP1(1) complement (5'-GCCACTCCCCA-3') (SEQ ID NO:18), where component 2 is a stem-loop containing an NF-KB1 variant motif (5'-TAGGGACTTTCCGG-3') (SEQ ID NO:89), where component 25 is a stem-loop containing an SP1(2) complement motif (5'-GTCCCGCCCA-3') (SEQ ID NO:90), and where component 32 is a bulge structure containing the SP1(1) motif (5'-TGGGGAGTGGC-3') (SEQ ID NO:19). (B) Predicted folding pattern of the HIV-1 LTR repressor utron after alteration of the sequence to allow folding into a more compact structure. Three pairs of stem-loops form loop-loop structures and a pair of bulges form a bulge-bulge structure through promoter motif complementary base pairing. In FIGS. 15A–B, the functional motifs are represented by cross-hatched boxes.

FIG. 16. Nucleotide sequence of TSU RNA. The gene promoter motifs are in bold face type with the type of motif indicated above the motif. The IL-4RE and ISRE starting at nucleotide 110 are partially overlapping and these motifs are labeled IL-4RE/ISRE. The polyA signal and ISRE beginning at nucleotide 453 are also partially overlapping and these motifs are labeled Poly-A/ISRE.

Figure 17:
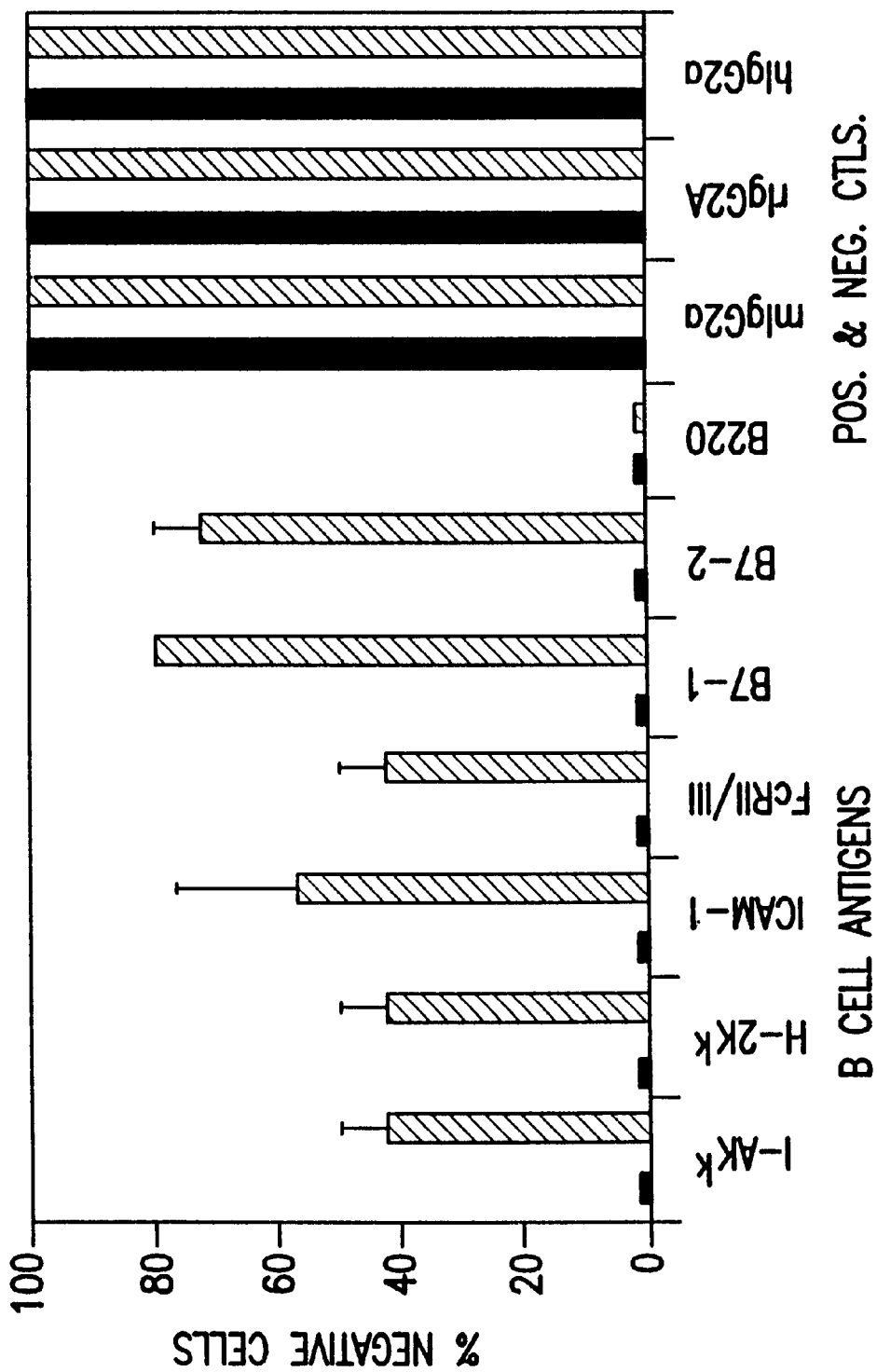

FIG. 17. Bar graph representing results of suppression of B cell antigens in TSU-pREP4 transfected CH27 mouse B lymphocyte cells. Solid bars represent the percentage of untransfected CH27 cells negative for the antigen tested (I-AK$^k$, H-2K$^k$, ICAM-1, FcRII/III, B7-1, B7-2, B220, mIgG2a, rIgG2a, hIgG2a) indicated on the X-axis. The cross-hatched bars represent the percentage of TSU-transfected CH27 cells negative for the antigen indicated on the X-axis.

5. DETAILED DESCRIPTION OF THE INVENTION

The invention provides molecules that regulate gene expression. Such molecules are RNA molecules, e.g., therapeutic RNAs, and their DNA analogs, and the cDNAs that encode them. The nucleic acids of the invention are termed herein utrons. Utrons are nucleic acids that comprise, preferably consist essentially of, a sequence containing one or more gene promoter motifs. Utrons can stimulate or inhibit cellular processes by a nucleic acid sequence-specific interaction with an aspect of the cellular machinery. In an embodiment, the nucleic acids of the invention suppress transcription, i.e., are target gene promoter-suppressing nucleic acids. In particular, the nucleic acids of the invention contain at least one promoter regulatory motif and are able to repress the expression of target genes. In one embodiment, the nucleic acids of the invention contain at least one sequence comprising one or more promoter regulatory motifs, which sequence is contiguous with a nucleotide sequence of at least 20 nucleotides, or 35, or 50, 100, or 500 nucleotides, not contiguous with the at least one sequence in any of the naturally occurring nucleic acids containing such motifs. In another specific embodiment, the utrons do not encode a polypeptide, particularly, a natural polypeptide. DNA analogs, preferably single-stranded DNA, of RNA utrons are also provided, i.e., containing the same sequence in which U's are replaced by T's, ribose is replaced by deoxyribose, and any poly A tail is absent. Functionally active derivatives are also provided. These gene promoter suppressing RNA and DNA molecules, and DNA molecules that encode them operably linked to a gene promoter of interest, all termed herein utrons, can be obtained by producing a molecule containing the appropriate structural and functional components, as taught by the present invention.

The nucleic acids of the invention (utrons) comprise one or more promoter regulatory motifs that allow these nucleic acids to regulate gene expression. Such a promoter regulatory motif is a promoter element or protein-binding motif of a gene promoter or an RNA or DNA motif that binds to a transcription factor, or a functionally active derivative or fragment of any of the foregoing. The genes that are regulated by utrons can be eukaryotic or prokaryotic. In a preferred embodiment of the invention, for regulation of a gene having a prokaryotic promoter, the promoter regulatory motif in a utron can be a nucleic acid motif that binds a sigma factor specific for an organism or a repressor factor regulating transcription of a specific gene or operon. In a preferred aspect, the nucleic acids of the invention comprise a plurality of defined structures containing one or more promoter regulatory motifs, selected from among stem-loop structures, hairpin structures, and bulge structures. Promoter regulatory motifs that can be incorporated into the utrons of the invention can be selected from among the many such regulatory motifs commonly known in the art. (For a review of such regulatory motifs, see Ghosh, 1990, Nucl. Acids Res. 18:1749–56.) Promoter motifs of a specific gene or gene family are selected for use when it is desired to regulate the expression of such gene or gene family. For example, a known promoter motif involved in transcriptional activation of a gene (e.g., an enhancer region, a transcription activating factor binding region, or other promoter element) can be used as the promoter regulatory motif(s) in a utron of the invention, for use in inhibiting transcription of such gene. In an alternative embodiment wherein enhancement of transcription is desired, a known promoter motif involved in transcriptional suppression can be used as the promoter regulatory motif(s) in a utron of the invention.

In a specific embodiment of the invention, the promoter regulatory motif is not a motif of the tropomyosin, troponin I, or α-cardiac actin genes, in particular, of the 3'-untranslated region of these genes.

In one specific embodiment, the invention provides a method of inhibiting an immune response in a subject in need thereof comprising administering to the subject an effective amount of a utron containing a promoter regulatory motif that regulates the IL-2 gene promoter. In another specific embodiment, the invention provides a method of inhibiting HIV replication and/or treating AIDS in a subject in need thereof comprising administering to the subject an effective amount of a utron containing a promoter regulatory motif that regulates an HIV promoter; in a particular aspect, the utron is an appropriate expression construct encoding an RNA containing the promoter regulatory motif.

In a particular embodiment of the present invention, mammalian expression cloning was used to isolate trophoblast cDNAs that act as dominant, trans-acting suppressors of the IFN-γ-induced expression of the MHC class II antigen HLA-DR on HeLa cells. DNA analogs of these RNAs are also provided. The present inventors have discovered and characterized a cDNA that expresses an RNA that silences MHC class I, MHC class II, ICAM-1, B7-1, B7-2 and FcγR gene expression. Analysis of this RNA, termed TSU, has revealed its structural and functional components. RNA molecules and the DNA molecules that encode them, that suppress gene expression, can be obtained by producing a molecule containing the appropriate structural and functional components, including the desired promoter regulatory motif, as taught by the is present invention.

In a specific embodiment, the present invention relates to nucleotide sequences of the TSU gene. The invention further relates to fragments and other derivatives, analogs and homologs of the TSU nucleic acid. The invention also relates to TSU derivatives and analogs which are functionally active, i.e., they are capable of displaying one or more known functional activities associated with the TSU nucleic acid. Such functional activities include, but are not limited to, an ability to inhibit (prevent or reduce) MHC class I (HLA-A, HLA-B, and HLA-C, or any one or two of these) and/or MHC class II (HLA-DP, HLA-DQ, and HLA-DR, or any one or two of these) and/or other STAT-responsive (ICAM-1, B7-1, B7-2 and FcγR, or any one, two or three of these) antigen expression, ability to interfere with STAT1 and/or other STAT transcription factor (STAT2, STAT3, STAT4, STAT5 and STAT6, or any one, two, three or four of these factors) function, ability to inhibit gene expression induced by cytokines such as interferon-α and β, granulocyte colony stimulating factor, oncostatin M, erythropoietin, granulocyte-macrophage colony stimulating factor, epidermal growth factor, growth hormone, ciliary neurotrophic factor, prolactin, leukemia inhibitory factor, interleukin-2, interleukin-3, interleukin-4, interleukin-5, interleukin-6, interleukin-8, interleukin-10, interleukin-13, and interleukin-15, ability to render cells nonimmunogenic, etc.

In a specific embodiment, a utron of the invention comprises one or more promoter regulatory motifs selected from the group consisting of GUAAAGUAA (SEQ ID NO:77), UUCCCUUUAA (SEQ ID NO:78), AGUUUCACU-UGAAA (SEQ ID NO:79), GUAUGGUAA (SEQ ID NO:80), UUACGUCAU (SEQ ID NO:81), UUAC-UAAUCA (SEQ ID NO:82), AGUUUGAGUUCUAA (SEQ ID NO:83), AGTTTCNNTTCNC/T (SEQ ID NO:20), and TTNCNNNAA; wherein N is any nucleotide.

In other specific embodiments, a utron comprises a plurality of copies of GTGAAATTGAAACT (SEQ ID NO:7) or GTATGGTAA (SEQ ID NO:8). In yet another embodiment, a utron comprises the sequence TTACAGCAC (SEQ ID NO:11), 5'-CGATCGGTGAAATTGAAACTCGATCG-3' (SEQ ID NO:33), 5'-CGATGTTGCTCTGTATGGTAAGAACATCG-3' (SEQ ID NO:31), or 5'-ACTTTTCTTCCCCTTTACAGCACAAATAAAGT-3' (SEQ ID NO:29). Another specific embodiment is directed to an isolated single-stranded RNA comprising at least three promoter regulatory motifs selected from the group consisting of GUGAAAUUGAAACU (SEQ ID NO:84), GUAUG-GUAA (SEQ ID NO:80), and UUACAGCAC (SEQ ID NO:85), each motif separated from another promoter regulatory motif by 2–300 contiguous bases; or a DNA analog thereof.

In other specific embodiments, a utron comprises one or more pairs of complementary promoter motifs. In particular embodiments, the motifs within each pair are greater than 50%, 70%, 80%, or 90% complementary to each other when aligned using one or more intramolecular A-U, C-G, G-U, and or A-G base-pairs. RNA utrons comprise sequences containing a plurality of complementary pairs of promoter regulatory motifs distributed along the single-stranded sequence such that, when the molecule is folded into stem-loop and/or bulge structures, the complementary promoter regulatory motifs can form additional tertiary structures by hydrogen-bonding between the loops and bulges yielding loop-loop structures, and/or loop-bulge structures, and/or bulge-bulge structures. The hydrogen-bonding can be traditional Watson-Crick base-pairing (A-U/T or C-G) or non-traditional base-pairing G-U/T and less preferably A-G).

In a particular embodiment, the utron is an RNA comprising at least one pair of promoter regulatory motifs in which the motifs are complementary sequences selected from the group consisting of (a) a GAS motif and GAS complement motif, and (b) an ISRE motif and ISRE complement motif; and in which hydrogen bonding can occur when the motifs of the pair are aligned by folding the RNA in an antiparallel orientation using one or more intramolecular A-U, C-G, G-U, and/or A-G base-pairs, and in which the inter-motif hydrogen bonding between a GAS motif and GAS complement motif occurs at at least positions 1–4 and 8–9 of the GAS motif; and in which the inter-motif hydrogen bonding between an ISRE motif and an ISRE complement motif occurs at at least positions 1–6 and 9–10 of the ISRE motif.

The invention provides methods of regulating gene expression in a subject comprising introducing into the subject an amount of a utron, preferably a purified utron, effective to regulate gene expression. The subject can be, for example, a cell in vitro, or an in vivo non-human animal or human. A specific embodiment relates to methods of inhibiting MHC Class I and/or Class II gene expression in a subject by introducing into the subject an TSU utron that is an expression construct encoding an TSU RNA. By way of example, but not limitation, the subject can be a human or non-human animal having or expected to receive an allogeneic or xenogeneic transplant, or having an autoimmune or inflammatory disease or disorder.

The present invention also relates to therapeutic and diagnostic methods and compositions based on gene promoter suppressing nucleic acids, preferably TSU nucleic acids, that contain at least one promoter element motif and are able to suppress a gene promoter of interest. The invention provides for therapeutic uses the generation of replacement cells in which expression of a gene or genes of interest is suppressed. In a particular embodiment, the invention provides methods for the generation of replacement cells for therapeutic uses, as well as allogeneic and xenogeneic tissue and organs that are less likely to trigger a cell-mediated immune response, thus reducing the risk of replacement cell and organ transplant rejection and reducing or obviating the necessity for immunosuppressive treatments.

The invention also provides methods of treatment of immunological disorders associated with undesirable immune and/or inflammatory reactions by suppressing expression of MHC class I and/or II antigen and/or other membrane proteins involved in the immune response (ICAM-1, B7-1, B7-2 and/or FcγR) by administration of TSU function in vivo. The invention also provides methods of treatment for diseases or disorders caused by viruses, eukaryotic pathogens or prokaryotic pathogens treatable by the suppression or enhancement of gene expression.

The invention also provides methods of producing RNA utrons of the invention, comprising culturing a recombinant cell containing a nucleic acid that can be transcribed to produce an RNA utron such that the RNA utron is produced, and recovering the produced RNA utron.

For clarity of disclosure, and not by way of limitation, the detailed description of the invention is divided into the subsections which follow.

5.1. PREPARATION OF AND COMPONENTS OF UTRONS

The present invention relates to gene promoter suppressing RNA molecules, and the cDNAs that encode them, as well as corresponding fragments, derivatives and homologs. Also provided are single-stranded DNA analogs of RNA molecules and fragments thereof (i.e., containing the same base sequence as the RNA, except with T substituted for U, and deoxyribose instead of ribose, and any poly A tail being absent). Nucleic acids capable of being transcribed to produce the active utron RNAs are also provided.

The utron RNA may include, in whole or in part, naturally occurring untranslated regions of mRNA or mRNAs, naturally occurring untranslated RNAs not transcribed contiguously with a protein coding region, or artificial (not known to be naturally occurring) RNAs. The utron RNAs of the present invention can stimulate or inhibit a cellular process, such as, but not limited to, transcription, DNA replication, RNA transport, RNA splicing, RNA turnover, RNA translation and nucleotide metabolism, by sequence-specific interaction with an aspect of the cellular machinery mediated by the gene whose expression is regulated by the utron.

In a preferred embodiment, the utron RNA of the present invention is a gene promoter activity-suppressing RNA that comprises promoter regulatory motifs, e.g., promoter elements or functional homologs thereof, more preferably, motifs which, at least in part, regulate the transcriptional activation of the target gene or genes and which RNA suppresses transcription of the target gene or genes.

In a specific embodiment, a gene promoter suppressing RNA is provided that consists of or comprises a plurality of one promoter regulatory motif or a combination of promoter regulatory motifs. Preferably, the promoter regulatory motifs are associated with the regulation of the target gene or genes. In a specific embodiment, the gene promoter suppressing utron consists of or comprises promoter regulatory motifs and flanking sequences not contiguous with these motifs in naturally occurring nucleic acids. In one embodiment, the gene promoter suppressing molecule is a single-stranded RNA; in another embodiment, the molecule is a single-stranded DNA analog (e.g., unmodified DNA or a phosphorothioate or peptidonucleic acid analog thereof) of such RNA; in yet another embodiment, the derivative is a double-stranded DNA molecule in which a sequence that is transcribed to produce a gene promoter suppressing RNA is operably linked to a transcriptional promoter. In a preferred aspect, the double-stranded DNA is transcribed to produce an RNA that comprises at least one sequence comprising one or more promoter motifs, contiguous with a nucleotide sequence of at least 20, or 30, or 50, or 100, or 500 nucleotides that is not contiguous with the at least one sequence in naturally occurring nucleic acids containing such one or more motifs. In another preferred aspect, the promoter regulatory motif contained within the double-stranded DNA molecule is not a regulatory motif of the transcriptional promoter also contained within the double-stranded DNA molecule.

In another particular embodiment, the utron is a naturally occurring RNA identified by the utron RNA's activity in an assay for suppression or enhancement of a cellular process. In a preferred embodiment, the RNA is identified by its activity in suppressing transcription from a promoter, particularly the promoter endogenously linked to the target gene or genes. The utron RNAs can, therefore, be isolated by any expression cloning method known in the art such as, but not limited to, those methods described infra Section 5.2, using any functional assay known in the art, including, but not limited to, the assays described infra Section 5.5 and the assay used to isolate the TSU gene described infra Section 7.2.

In specific embodiments, the utron RNA consists of or comprises a plurality (e.g., at least 2, preferably in the range of 2–50, 2–5, 5–10, or most preferably 5–25 of the RNA component structures described below, each of which component structure comprises one or more (preferably at least 2, more preferably in the range of 2–10 or 2–5) promoter regulatory motifs. The utron optionally also contains a 31 polyA signal followed by a spacer of 10–20 bases followed by a polyA $[(A)_n]$ tail (a DNA that is transcribed to produce such a utron would preferably lack the poly-A tail, but would preferably encode the poly-A signal) and optionally a cap structure at the 5' terminus. In other specific embodiments, the utron RNA is not more than 3,000 bases (or base pairs, if double-stranded), not more than 1,000 bases, not more than 510 bases, or not more than 255 bases.

DNA analogs of all the utron RNAs of the invention are also provided.

In a specific embodiment, the gene suppressing nucleic acid (utron) is a double-stranded DNA comprising a promoter (e.g., SV40 or other viral, or mammalian, gene promoter) operably linked to a sequence that can be transcribed to produce a plurality of RNA component structures of the invention containing promoter regulatory motifs.

The invention also pertains to utron nucleic acids with functional homologs of known or naturally occurring functional RNA motifs, preferably promoter element motifs.

In vitro assays for utron activity are performed by any method known in the art, including, but not limited to, the methods described in Section 5.5. These nucleic acids containing functional homologs can be made by altering the bases of the functional RNA motif by substitutions, additions or deletions. These modifications can be made using any method known in the art, including, but not limited to, in vitro or in vivo mutagenesis techniques such as chemical mutagenesis, in vitro site-directed mutagenesis (Hutchinson et al., 1978, *J. Biol. Chem.* 253:6551), use of TAB® Linkers (Pharmacia), etc.

Synthetic utrons can be prepared by standard methods, exemplified by, but not limited to, annealing of sets of partially overlapping, synthetic, complementary oligodeoxynucleotides, filling in the sets of incomplete double-stranded intermediate structures by the polymerase chain reaction, formation of the final construct by ligation of partial structures or amplification of partial structures, ligation to suitable vectors for growth in bacteria or other hosts, and finally subcloning into other appropriate expression vectors for expression as RNA in eukaryotic cells (Sambrook et al., 1989, Molecular Cloning, A Laboratory Manual, Cold Spring Harbor Laboratory, 2d. Ed., Cold Spring Harbor, N.Y.; Kriegler, 1990, Gene Transfer and Expression, A Laboratory Manual, Stockton Press, NY).

Utrons can be used to repress target genes in the cytoplasm or nucleus of eukaryotic cells or in bacteria. The target genes may include constitutively expressed or inducible genes, and may include genes expressed in a tissue-specific manner or genes expressed ubiquitously in an organism. Utrons may be applied to the suppression of endogenous genes in single-celled and multicellular plants and animals and humans. Applications of utrons may include repression of genes in pathogenic eukaryotic microorganisms, or bacteria. The pathogens may include commercial plant crop pathogens, agricultural pests, and veterinary and human microbial pathogens, parasites, and viruses.

Naturally occurring or artificial (synthetic) utrons are targeted to the cytoplasm by including a polyadenylation signal at the 3'-end of a construct encoding the utron, or a 5' cap and a 3' polyadenylation signal followed by a spacer and poly A tail on an RNA utron itself; nuclear utrons have no poly-adenylation signal. Cytoplasmic utrons may block transcription factor(s) that are normally found in the cytoplasm. After the transcription factor(s) are activated by extracellular signals, the cytoplasmic utron binds gene promoter recognition site(s) on the protein(s). Utron binding to activated transcription factors blocks the function of these proteins that normally bind target sequences in the nucleus to take part in inducible gene expression. In the case of nuclear utrons, these RNAs may block transcription factors found in the nucleus that normally function constitutively or join with other activated transcription factors to cause inducible gene expression. Utrons can include components of naturally occurring and synthetic sequences.

Other functions of natural and synthetic utrons include the stimulation or inhibition of other cellular metabolic and transport functions based on utron interaction in a sequence-specific manner with other components of cellular machinery, such as DNA replication, RNA transport, RNA splicing, RNA turnover, RNA translation, and nucleotide metabolism.

In a preferred aspect, the gene promoter suppressing nucleic acid (utron) contains a set of promoter regulatory motifs which bind transcription factors and regulate or can regulate transcription from the gene promoter in which these elements naturally occur. Particular embodiments of this invention are synthetic human IL-2 repressing utron and a synthetic HIV-1 LTR suppressing utron depicted in FIGS. 14A and B and FIGS. 15A–C, respectively, and described infra in Sections 8 and 9, as well as fragments and derivatives thereof. Two examples of utrons are presented in Sections 8 and 9 hereinbelow: a synthetic IL-2 gene repressor utron and a synthetic HIV-1 LTR repressor utron. The synthetic utrons illustrate the general application of utrons for repression of eukaryotic genes based on knowledge of sequences and functional properties in cells of the gene promoter motifs. Synthetic utrons such as the IL-2 gene repressor utron and the synthetic HIV-1 LTR repressor utron can be prepared by standard methods of oligonucleotide synthesis and standard methods of DNA cloning. The expression of natural or synthetic utrons in cells can be accomplished by the use of standard methods using eukaryotic expression vectors. These methods are described below.

The gene promoter suppressing RNA, or the DNA which encodes it, may be prepared according to the method described infra in Section 8 or by any method known in the art, for example, but not limited to, oligonucleotide synthesis, standard DNA cloning methods and expression with standard expression vectors and any of the methods described infra in Section 5.2.

Utrons such as the IL-2 and HIV-1 LTR synthetic utrons described by way of example in Sections 8 and 9 below, can form the starting point for optimization experiments to yield structures with greater gene repression activity. Optimization of the design of the structural or functional components can be accomplished by varying the number of components, the orientation of each functional gene promoter motif within each component, and the promoter sequence or variant incorporated into each component. It is well established that small variations of the sequences of DNA gene promoter motifs give selective binding of certain closely related DNA-binding transcription factors. Therefore, it is predicted that small variations of the sequences of the utron RNA motifs will result in selective binding and selective inhibition of certain closely related transcription factors.

Based on the sequence of the natural utron TSU, it seems likely that several closely related gene promoter motifs will be required within one utron in order to efficiently repress the group of related promoter-binding transcription factors present in any one cell type. The preference for utrons with a particular predicted folding pattern is determined empirically by observing the differences in repression activity with various structures.

5.1.1. VARIOUS FORMS OF THE COMPONENTS OF UTRONS

The following is a list of RNA components which represent the preferred structural and functional building blocks of utrons.

1. Stem-loop RNA structures.
2. Hairpin RNA structures.
3. Bulge RNA structures.
4. Pseudoknot RNA structures.

5. Functional RNA motifs (promoter regulatory motifs that are expressed gene promoter motifs that interact with transcription factors, or RNA sequences that function by interacting with other cellular components that regulate transcription). The functional motifs are embedded in the various structures listed above to form a natural or synthetic utron.

Components 1 through 4, stem-loop, hairpin, bulge and pseudoknot structures, are graphically depicted and size specifications for the particular structural or functional aspects are given in FIGS. 12A–D.

In a particular embodiment, the gene promoter suppressing RNA of the present invention is obtained by constructing a synthetic RNA or DNA analog thereof, or DNA which encodes that RNA, which consists of or comprises a plurality of promoter regulatory motifs, each of these motifs contained within an RNA component structure, such as, but not limited to, stem-loop structures, hairpin structures, bulge structures or pseudoknot structures, as depicted by way of example in FIGS. 12A–D.

Each RNA component structure may contain a plurality of promoter regulatory elements separated by a spacer, j. Optionally, only one functional motif (promoter regulatory element) is present in each RNA component structure, in which case the spacer j will be zero. Preferably, the utron of the invention contains a plurality of RNA component structures. Each RNA component structure can alternatively be present as a DNA analog.

Figure 12A:
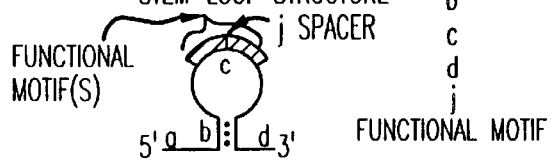

Each stem-loop, depicted by way of example in FIG. 12A, contains one or more functional motifs, i.e., promoter regulatory motifs, in a loop, c, of 10–50 bases, preferably 10–20 bases, with an optional spacer, j, of 0–50 bases, preferably 0–10 bases separating the promoter regulatory motifs in the event that two or more are present. Additionally, the structure has 4–20, preferably 5–10, bases, b, complementary in inverse order on either side of the loop (theoretically capable of hybridizing to form a stem structure), surrounded by 0–100, preferably 0–10, bases on both the 5' and 3' sides, a and d, respectively, that can act as spacers between the RNA component structures if more than one is present in the utron.

Figure 12B:
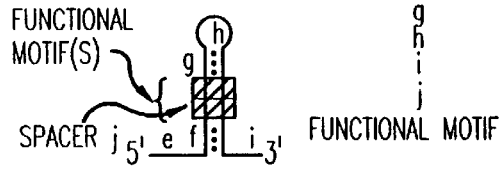
Figure 12C:
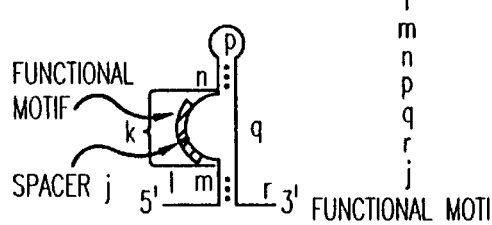
Figure 12D:
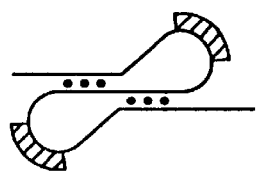

The hairpin structure, depicted by way of example in FIG. 12B, contains a loop, h, of 1–8, preferably 4–6 bases, surrounded on the 5' side and the 3' side by a sequence of bases that are complementary in inverse order, one of which complementary sequences contains (i) the functional motif; (ii) an optional spacer, j, of 0–50, preferably 0–10 bases between functional motifs in the event that a plurality of functional motifs are present; and (iii) two spacer regions g, and f, respectively, on either side of the functional motif, each of which is 0–20 bases, preferably 5–10 bases; all of which sequence of complementary bases is surrounded both 5' and 3' by 0–100, preferably 0–10, bases, e, and i, respectively, acting as spacers between the RNA component structures should more than one be present.

The bulge structures, depicted by way of example, contain a loop, p, of 1–8 bases, preferably 4–6 bases, surrounded on each side by 4–20, preferably 5–10 complementary base pairs, n, capable of hybridizing to each other; these bases are flanked in turn, by 4–50, preferably 6–20, bases which contain the functional motif on one side, k, and 0–50, preferably 6–20, bases, q, not complementary to the bases containing the functional motif on the other side; these regions are surrounded by 4–20, preferably 5–10, base pairs, m, complementary in inverse order and capable of hybridizing to each other. Finally, the entire preceding bulge structure is surrounded by 0–100, preferably 0–10, bases on each side, l, and r, respectively, acting as spacers between the RNA component structures in the event that more than one is present.

Component stem-loops and/or bulge structures that form additional hydrogen bonds between complementary loops and/or complementary bulges can create a wide array of possible pseudoknot or tertiary structures, and the design of synthetic utrons containing these structures provides for double-stranded RNA assuming various bent A-form or modified A-form helices.

Accordingly, the invention provides single stranded DNA or RNA molecules comprising one or more component structures selected from the group consisting of:

a stem-loop component structure consisting of:

(a) a first sequence in the range of 10–50 bases, consisting of (i) one or more promoter regulatory motifs, each motif separated from each other motif by 0–50 bases, (ii) flanking sequences 5' to the motif, and (iii) flanking sequences 3' to the motif;

(b) a second sequence of 4–20 bases flanking said first sequence on the 5' side;

(c) a third sequence flanking said first sequence on the 3' side, said second and third sequences being of equal length and complementary to each other in inverse order;

(d) a fourth sequence flanking said second sequence on the 5' side, in the range of 0–100 bases; and (e) a fifth sequence flanking said third sequence on the 3' side, in the range of 0–100 bases;

a hairpin component structure consisting of:

(a) a first sequence in the range of 1–8 bases;

(b) a second sequence consisting of (i) one or more promoter regulatory motifs, each motif separated from each other motif by 0–50 bases; (ii) a flanking sequence of 0–20 bases 3' to said motif; and (iii) a flanking sequence of 0–20 bases 5' to said motif; in which either the flanking sequence 3' to the motif or the flanking sequence 5' to the motif is contiguous with said first sequence;

(c) a third sequence of equal length as said second sequence and complementary in inverse order to said second sequence;

(d) a fourth sequence in the range of 0–100 bases, flanking said second sequence; and (e) a fifth sequence in the range of 0–100 bases, flanking said third sequence; and a bulge component structure consisting of:

(a) a first sequence in the range of 1–8 bases;

(b) a second sequence of 4–20 bases 5' to said first sequence;

(c) a third sequence 3' to said first sequence and of equal length as said second sequence and complementary in inverse order to said second sequence;

(d) a fourth sequence of 4–50 bases 5' to said second sequence and consisting of one or more promoter regulatory motifs, each motif separated from each other motif by 0–50 bases;

(e) a fifth sequence of 0–50 bases 3' to said third sequence;

(f) a sixth sequence of 4–20 bases 5' to said fourth sequence;

(g) a seventh sequence 3' to said fifth sequence and of equal length as said sixth sequence and complementary in inverse order to said sixth sequence;

(h) an eighth sequence in the range of 0–100 bases, 5' to said sixth sequence; and (i) a ninth sequence in the range of 0–100 bases, 3' to said seventh sequence.

In a specific embodiment, a utron comprises at least two component structures selected from among stem-loop, hairpin, and bulge component structures. In a particular embodiment, at least two component structures are contiguous, that are not naturally contiguous.

5.2. ISOLATION OF THE TROSPHOBLAST STAT UTRON GENE

A preferred embodiment of the present invention relates to TSU RNA and corresponding fragments, derivatives and homologs. Also provided are single-stranded DNA analogs of TSU RNA and fragments thereof (i.e., containing the same base sequence as the RNA, except with T substituted for U, and deoxyribose instead of ribose). Nucleic acids capable of being transcribed to produce the active TSU RNAs or DNAs are also provided. The TSU cDNA can be isolated from a cDNA library prepared from mRNA isolated from trophoblast cells, and is able to suppress IFN-γ-induced MHC class I, MHC class II, ICAM-1, B7-1, B7-2 and/or FcγR antigen expression, and/or IFN-γ-induced STAT1 migration to the nucleus and/or other cytokine-induced STAT2, STAT3, STAT4, STAT5 and STAT6 migration to the nucleus (Darnell et al., 1994, *Science* 264:1415–1420). In specific embodiments, TSU nucleic acids comprise the DNA sequence of FIG. 5B (SEQ ID NO: 1) and the RNA sequence encoded by it and shown in FIG. 16 (SEQ ID NO:86). Specific embodiments also include the DNA sequences of and the RNA sequences encoded by oligonucleotide numbers 6, 7 and 10 of FIG. 10 (SEQ ID NOS:33, 31, and 29, respectively). Nucleic acids can be single or double stranded. The invention also relates to nucleic acids hybridizable to or complementary to the foregoing sequences.

In a preferred embodiment, the TSU gene is obtained by the method described infra in Section 7.1.

The TSU gene can also be isolated by any method known in the art. Any mammalian cell (e.g., of goat, primate (e.g., monkey), horse, cow, mouse, rat, dog, cat, etc.) can potentially serve as the nucleic acid source for the molecular cloning of the TSU gene from various species. In a preferred aspect, the TSU gene is isolated from a human cell. The DNA may be obtained by standard procedures known in the art from cloned DNA (e.g., a DNA "library"), by chemical synthesis, by cDNA cloning, or by the cloning of genomic DNA, or fragments thereof, purified from the desired cell type (see, for example Sambrook et al., 1989, Molecular Cloning, A Laboratory Manual, Cold Spring Harbor Laboratory, 2d. Ed., Cold Spring Harbor, N.Y.; Glover, D. M. (ed.), 1985, DNA Cloning: A Practical Approach, MRL Press, Ltd., Oxford, U.K., Vol. I, II). Whatever the source, the gene should be molecularly cloned into a suitable vector for propagation of the gene.

In particular, the TSU gene can be isolated by screening a cDNA library prepared from cells of tissue which do not express MHC class I and II antigens in response to IFN-γ stimulation, such as, but not limited to, trophoblast cells or cell lines. Libraries can be prepared by any method well known in the art and screened by nucleic acid hybridization using a portion of an TSU (of any species) gene or its specific RNA, or a fragment thereof, e.g., the promoter motifs, as a labeled probe using methods well known in the art. Those cDNA clones with substantial homology to the probe will hybridize. Selection can also be carried out on the basis of the properties of the RNA transcribed from the gene, for example, the ability to suppress MHC class I and II antigen expression. Alternatively, the presence of the gene may be detected by assays based on the physical or chemical properties of its RNA product.

The TSU gene can also be identified by mRNA selection by nucleic acid hybridization. In this procedure, fragments are used to isolate complementary mRNAs by hybridization. The hybridization probes may represent available, purified TSU DNA of another cell type or from another species and the mRNA may represent mRNAs from another cell type or another species. Functional assays (e.g., suppression of MHC class I and II antigen and ICAM-1, FcγR, B7-1 and B7-2 antigen expression or inactivation of STAT1 function, see examples infra) of the isolated mRNAs identify the mRNA and, therefore, the complementary DNA fragments that contain the desired sequences.

Polymerase chain reaction (PCR) can also be used to amplify the desired sequence from cDNA, genomic DNA, a library or any other source. For example, the oligonucleotide primers pSH4-1 and pSH4-2 derived from flanking vector sequences (SEQ ID NOS:23 and 24, respectively) described in Section 7.1, primers containing sequences of the promoter motifs, primers derived from the 5' TSU sequence, such as TSU-1, 5'-GTGTGATCTGAAAACCCTGCTTGG-3' (SEQ ID NO:87) and 3'TSU sequence, such as TSU-2, 5'-CCATACAGAGCAACATACCAGTAC-3' (SEQ ID NO:88), or any other appropriate primer encoded by a homolog of the TSU gene can be used as primers in PCR.

The TSU gene, or portions thereof, can also be obtained by chemically synthesizing the gene sequence itself.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as pBR322 or pUC plasmid derivatives. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and TSU gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate the isolated TSU gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

5.3. TSU FRAGMENTS, DERIVATIVES AND HOMOLOGS

A particular embodiment of the invention further relates to derivatives (e.g., fragments) and homologs of the TSU nucleic acids containing promoter elements able to suppress a MHC class I and/or II antigen expression, preferably as well as ICAM-7, B7-1, B7-2 and/or FcγR antigen expression. In a more particular embodiment, the invention relates to TSU fragments and derivatives or homologs of such fragments that comprise, or alternatively consist of, one or more of the promoter motifs of the TSU gene, including, but not limited to, the ISRE, GAS or IL-4-RE conserved promoter elements, functional (e.g., MHC, ICAM-7, B7-1, B7-2 and/or FcγR antigen expression suppressors) fragments of any of the foregoing, or any combination of the foregoing. In particular, the fragments of the invention and derivatives or homologs of such fragments comprise or consist of one or more of the promoter motifs of Table 1 (see Section 7.2), preferably No. 6 (SEQ ID NO:7), No. 7 (SEQ ID NO:8) and/or No. 10 (SEQ ID NO:11), one or more of the sequences of Table 1 flanked by 5-bases on each side that are complementary in the opposite orientation so as to be able to hybridize to each other, or the sequences shown in FIG. 10, preferably No. 6, No. 7 and/or No. 10 (SEQ ID NOS:33, 31, and 29, respectively). In example Section 7.2 and in FIG. 5B, TSU fragments containing these elements are identified.

In specific embodiments, a TSU derivative is provided that contains a plurality of copies of a single promoter regulatory motif of the TSU gene, alone or in combination with other promoter regulatory motifs. Preferably, the promoter regulatory motif is one contained within the TSU gene and, more preferably, has a sequence selected from among the 12 motifs shown in Table 1, or a consensus GAS or ISRE sequence, which is any nucleotide sequence which contains the nucleotides conserved among many of the known ISRE or GAS elements. In particular, the consensus ISRE sequence is AGTTTCNNTTCNC/T (SEQ ID NO:20) and the consensus GAS sequence is TTNCNNNAA where N represents any one of the four nucleotides (Darnell et al., 1994, Science 264:1415–1420 at 1416). In one embodiment, the TSU derivative is a single-stranded RNA; in another embodiment, the derivative is a single-stranded DNA analog of such RNA; in yet another embodiment, the derivative is a double-stranded DNA molecule in which a sequence that is transcribed to produce an TSU RNA or derivative thereof is operatively linked to a transcriptional promoter. In a preferred aspect, the double-stranded DNA is transcribed to produce an RNA that comprises promoter motifs contiguous with nucleic acid sequence of at least 20, or 50, or 100, or 500 nucleotides not contiguous with the promoter motif in naturally occurring sequences.

In a specific embodiment, the TSU derivative contains, or alternatively encodes, one or more structural RNA components, such as, but not limited to, stem loops, hairpins, bulge and pseudoknot structures, containing promoter motifs, preferably those from Table 1, each structure having one of the configurations shown in FIGS. 12A–D and described supra in Section 5.1.

Preferably, the TSU derivative contains or encodes pairs of complementary promoter regulatory motifs within stem-loop and/or bulge structures that, when folded further, form tertiary loop-loop, loop-bulge, and bulge-bulge structures containing double-stranded RNA gene promoter regulatory motif analogs, in particular, bent helical or modified helical configurations.

In a specific embodiment, the TSU derivative is a double-stranded DNA comprising a promoter (e.g., SV40 or other viral promoter) operatively linked to a plurality (e.g., at least 2, preferably in the range of 2–50, 2–10, 2–5 or 5–25) of functional RNA component structures. In one embodiment, the promoter motifs of the functional RNA structures are selected from among those shown in Table 1, preferably No. 6 (SEQ ID NO:7), No. 7 (SEQ ID NO:8), and/or No. 10 (SEQ ID NO:11) of Table 1. In another embodiment, the functional RNA structures are selected from among those shown in FIG. 10, preferably No. 10, No. 7, and No. 6 of FIG. 10 (SEQ ID NOS:33, 31, and 29, respectively).

In a specific embodiment, an TSU derivative is provided that comprises or, alternatively, consists essentially of the 12 sequence motifs shown in Table 1. In another specific embodiment, an TSU derivative is provided that comprises or, alternatively, consists essentially of one or more of the 12 sequence motifs shown in Table 1. In another embodiment, an TSU derivative is provided that comprises or, alternatively, consists of functional RNA component structures containing the 11 promoter sequence motifs (not including poly-A) shown in Table 1; a poly-A signal is optionally present at the 3'-terminus and a cap structure at the 5'-terminus. In another embodiment, an TSU derivative is provided that comprises or, alternatively, consists essentially of one or more of the 11 promoter motifs of Table 1, each present in a stem loop; optionally with a poly-A signal at the 3' terminus and cap structure at the 5' terminus.

In another specific embodiment, the TSU derivative lacks one or more of the 11 promoter motifs present in the TSU cDNA (i.e., those listed in Table 1, nos. 1–10 and 12). In a particular embodiment, the derivative lacks the IL-4RE motifs. The derivative may include or lack a poly-A signal at the 3' terminus and include or lack a cap structure at the 5' terminus.

In other specific embodiments, the TSU derivative is not more than 3,000 bases (or base pairs, if double-stranded), not more than 1,000 bases, not more than 510 bases, or not more than 255 bases.

In a specific embodiment, an TSU derivative is provided that suppresses expression of one or more particular MHC genes, selected from among any of the HLA genes or their analogs and ICAM-1, B7-1, B7-2 and FcγR genes in non-human species. In another embodiment, such a derivative does not suppress expression of one or more other antigen genes.

The production and use of TSU fragments and derivatives thereof are within the scope of the present invention. In a specific embodiment, the fragment or derivative or homolog of such fragments are functionally active, i.e., have the ability to suppress MHC class I and II antigen and ICAM-1, B7-1, B7-2 and FcγR antigen expression or inhibit IFN-γ-induced STAT1 nuclear migration. In vitro assays for activity are performed by any method known in the art, including, but not limited to, the methods described in Section 5.5.

The invention also relates to TSU homologs or fragments thereof. In particular, the TSU gene homologs or fragments thereof are made by altering the TSU sequences by substitutions, additions or deletions that provide for functionally equivalent molecules. For example, but not by way of limitation, nucleotide bases in the regions not containing a conserved promoter element could be altered without affecting the activity of the TSU molecule. Furthermore, alterations can be made in the bases able to form functional RNA structures in TSU RNA or single-stranded DNA oligonucleotides as long as complementary changes are also made to the base with which the altered base pairs, for example, if one base is changed from cytosine to adenine, the other base should also be changed from guanine to thymidine. In another embodiment, TSU homologs from other species, in particular, but not limited to, mice, rats and pigs, are isolated according to methods described supra at Section 5.2. Other alterations which result in a functional TSU nucleic acid are also encompassed by the invention.

In a specific embodiment of the invention, nucleic acids consisting of or comprising a fragment of an TSU nucleic acid consisting of at least nine (continuous) nucleotide bases of the TSU nucleic acid is provided. Derivatives or analogs of TSU include, but are not limited to, those functionally active molecules comprising regions that are substantially homologous to TSU or fragments thereof or are capable of hybridizing to TSU sequence under high stringency, moderate stringency, or low stringency conditions. By way of example, and not intended as limitation, procedures using such conditions of low stringency are as follows (see also Shilo and Weinberg, 1981, Proc. Natl. Acad. Sci. USA 78:6789–6792): Filters containing DNA are pretreated for 6 h at 40° C. in a solution containing 35% formamide, 5× SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2× SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and reexposed to film. Other conditions of low stringency which may be used are well known in the art (e.g., as employed for cross-species hybridizations). Procedures using such conditions of high stringency are as follows: Prehybridization of filters containing DNA is carried out for 8 h to overnight at 65° C. in buffer composed of 6× SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10$^6$ cpm of $^{32}$P-labeled probe. Washing of filters is done at 37° C. for 1 h in a solution containing 2× SSC, 0.01% PVP, 0.01% Ficoll, and 0.01% BSA. This is followed by a wash in 0.1× SSC at 50° C. for 45 min before autoradiography. Other conditions of high stringency which may be used are well known in the art. Procedures using such conditions of moderate stringency are as follows: Filters containing DNA are pretreated for 6 h at 55° C. in a solution containing 6× SSC, 5× Denhart's solution, 0.5% SDS and 100 µg/ml denatured salmon sperm DNA. Hybridizations ar carried out in the same solution and 5–20× 10$^6$ cpm $^{32}$P-labeled probe is used. Filters are incubated in hybridization mixture for 18–20 h at 55° C., and then washed twice for 30 minutes at 60° C. in a solution containing 1× SSC and 0.1% SDS. Filters are blotted dry and exposed for autoradiography. Other conditions of moderate stringency which may be used are well-known in the art. Washing of filters is done at 37° C. for 1 h in a solution containing 2× SSC, 0.1% SDS.

The TSU derivatives and analogs of the invention can be produced by various methods known in the art. For example, the cloned TSU gene sequence can be modified by any of numerous strategies known in the art (Maniatis, T., 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro.

Additionally, the TSU-encoding nucleic acid sequence can be mutated in vitro or in vivo, to create and/or destroy, or to create variations in functional regions and/or form new restriction endonuclease sites or destroy preexisting ones, to facilitate further in vitro modification. Any technique for mutagenesis known in the art can be used, including, but not limited to, chemical mutagenesis, in vitro site-directed mutagenesis (Hutchinson et al., 1978, J. Biol. Chem 253:6551), use of TAB® linkers (Pharmacia), etc.

5.4. UTRON NUCLEIC ACIDS

Utron, and particularly gene promoter suppressing, DNA, RNA, fragments and other derivatives, and nucleic acids that encode the same can be DNA or RNA or chimeric mixtures or derivatives or modified versions thereof, single-stranded or double-stranded.

In a preferred aspect of the invention, a gene promoter suppressing oligonucleotide, preferably an TSU oligonucleotide, is provided, preferably of single-stranded DNA. In a most preferred aspect, such an oligonucleotide comprises a sequence encoding or containing one or more of the promoter motifs of the TSU gene. The oligonucleotide may be modified at any position on its structure with substituents generally known in the art.

The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. USA 86:6553–6556; Lemaitre et al., 1987, Proc. Natl. Acad. Sci. 84:648–652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6:958–976) or intercalating agents (see, e.g., Zon, 1988, Pharm. Res. 5:539–549).

The utron oligonucleotide can also be a peptido-nucleic acid ("PNA") based on a linked N-(2-aminoethyl)glycine backbone to which normal DNA bases have been attached (Egholm et al., 1993, Nature 365:566–67). This PNA obeys specific Watson-Crick base pairing, but with greater free energy of binding and correspondingly higher melting temperatures. Suitable oligomers may be constructed entirely from PNAs or from mixed PNA and DNA and/or RNA oligomers.

In a preferred embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

The oligonucleotide of the invention may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine.

In another embodiment, the oligonucleotide comprises at least one modified sugar moiety selected from the group including, but not limited to, arabinose, 2-fluoroarabinose, xylulose, and hexose.

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g., by use of an automated DNA synthesizer (such as are commercially available from Biosearch, Applied Biosystems, etc.). As examples, phosphorothioate oligos may be synthesized by the method of Stein et al. (1988, Nucl. Acids Res. 16:3209), methylphosphonate oligos can be prepared by use of controlled pore glass polymer supports (Sarin et al., 1988, Proc. Natl. Acad. Sci. USA 85:7448–7451), etc.

In a specific embodiment, the oligonucleotide comprises catalytic RNA, or a ribozyme (see, e.g., PCT International Publication WO 90/11364, published Oct. 4, 1990; Sarver et al., 1990, Science 247:1222–1225). In another embodiment, the oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330).

In an alternative embodiment, the gene promoter suppressing nucleic acid, preferably the TSU nucleic acid, of the invention is operatively linked to a promoter such that the RNA is produced intracellularly by transcription from a sequence. For example, a vector can be introduced in vivo such that it is taken up by a cell, within which cell the vector or a portion thereof is transcribed, producing a nucleic acid (RNA) of the invention. Such a vector would contain a sequence encoding the gene promoter-suppressing nucleic acid. In a preferred embodiment, the nucleic acid is DNA if the source of RNA polymerase is DNA-directed RNA polymerase, but the nucleic acid may also be RNA if the source of polymerase is RNA-directed RNA polymerase or if reverse transcriptase is present in the cell or provided to produce DNA from the RNA. Such a vector can remain episomal or become chromosomally integrated, as long as it can be transcribed to produce the desired RNA. Such vectors can be constructed by recombinant DNA technology methods standard in the art. Vectors can be plasmid, viral, or others known in the art, used for replication and expression in mammalian cells. Expression of the sequence encoding the gene promoter suppressing RNA can be by any promoter known in the art to act in mammalian, preferably human, cells. Such promoters can be inducible or constitutive. Such promoters include, but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the HSV-1 (herpes simplex virus-i) thymidine kinase promoter (Wagner et al., 1981, Proc. Natl. Acad. Sci. USA 78:1441–1445), the regulatory sequences of the metallothionein gene (Brinster et al., 1982, Nature 296:39–42), etc., as well as the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in erythroid cells (Mogram et al., 1985, Nature 315:338–340; Kollias et al., 1986, Cell 46, 89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropin releasing hormone gene control region which is active in the hypothalamus (Mason et al., 1986, Science 234:1372–1378). The promoter element which is operatively linked to the gene promoter suppressing nucleic acid can also be a bacteriophage promoter with the source of the bacteriophage RNA polymerase expressed from a gene for the RNA polymerase on a separate plasmid, e.g., under the control of an inducible promoter, for example, the gene promoter suppressing nucleic acid operatively linked to the T7 RNA polymerase promoter with a separate plasmid encoding the T7 RNA polymerase.

5.5. ASSAYS FOR UTRON FUNCTION

The functional activity of utrons, particularly gene promoter suppressing, nucleic acids, fragments and derivatives can be assayed by various methods.

The utron nucleic acids of the present invention can be assayed by any method known in the art. Utron nucleic acids which enhance a cellular function can be assayed by any method known for detecting an increase in that function and utron nucleic acids which suppress a cellular function can be assayed by any method known for detecting the decrease or absence of the cellular function.

Utron molecules, fragments and derivatives which enhance or suppress transcription of a target gene can be assayed by any method known in the art for measuring the transcription from a specific gene promoter. For example, but not by way of limitation, the utron nucleic acid of interest can be introduced into a cell, either transiently or stably, by any method known in the art, e.g., transfection, electroporation, microinjection, etc. The enhancement or suppression of transcription of the target gene of interest can be measured by any method for detecting the mRNA transcribed from the target gene, for example, Northern blot analysis, as described infra Section 7.1.6. Alternatively, the promoter for the gene of interest can be cloned upstream of a reporter gene, such as thymidine kinase (for assaying suppression of a gene promoter inducible by an extracellular signal, see infra Section 6.1), β-galactosidase, luciferase or any other reporter gene known in the art, and, after introduction of the utron nucleic acid, transcription from the promoter can be assayed by any method known for detecting that reporter gene RNA or gene product.

In particular, the TSU homolog, fragment or derivative can be assayed as described infra Section 7.1.1. Briefly, the nucleic acid is introduced by transfection (e.g., lipofection), electroporation, microinjection, or any method known in the art into a cultured cell, the cell is stimulated with IFN-γ, and MHC antigen expression assayed by immunostaining or any other method well known in the art. Nucleic acids which prevent IFN-γ stimulated MHC antigen expression in comparison with controls are active.

TSU fragments and derivatives can also be assayed by their ability to inactivate STAT1 function as described infra Sections 7.1.3–7.1.5. Briefly, nucleic acid containing the fragment or derivatives is introduced into a cell by the methods described or any other method known in the art, and the cell is treated with IFN-γ and is stained with anti-STAT1 antibody. TSU fragments and derivatives that prevent STAT1 movement into the nucleus, as determined by immunostaining, are active and included within the scope of the invention.

Additionally, TSU fragments and derivatives can also be assayed for their ability to suppress expression of ICAM-1, B7-1, B7-2 and Fc Receptor antigens as described infra Section 10. Briefly, nucleic acid containing the fragment or derivative is transfected by any method known in the art into a cultured cell. The transformed cells are assayed for ICAM-1, Fc Receptor, B7-1 and/or B7-2 antigen expression by immunostaining or any other method well-known in the art. Nucleic acids which suppress ICAM-1, Fc Receptor, B7-1, and/or B7-2 antigen expression in comparison with controls are active.

Other methods will be known to the skilled artisan and are within the scope of the invention.

5.6. THERAPEUTIC USES

The invention provides for therapeutic methods using utron nucleic acids for enhancement or suppression of all processes which depend upon sequence specific interactions of nucleic acids with the cell machinery, in particular, the invention provides gene promoter suppressing nucleic acids with gene promoter motif elements for the enhancement or suppression of transcription of a target gene. More particularly, the invention provides therapeutic methods using TSU nucleic acids to prevent MHC class I and class II antigen expression. The invention provides for treatment of various diseases and disorders by administration of a therapeutic compound. Such "Therapeutics" include, but are not limited to: utron nucleic acids, including both RNA and DNA, and analogs and derivatives (including fragments) thereof (e.g., as described in Section 5.2), and cells or tissues or organs recombinant for the utron nucleic acid. In a preferred embodiment, the therapeutic includes TSU nucleic acids, analogs and derivatives, cells or organs recombinant for the TSU gene. In particular, disorders treatable by enhancement or suppression of transcription of a specific gene or genes, cell replacement therapy and organ transplantation and immune disorders involving MHC class I and II antigen expression are treated or prevented by methods of the present invention. The invention also relates to methods for preparation of donor xenogeneic organ transplants. The above is described in detail in the subsections below.

5.6.1. CELL REPLACEMENT THERAPY

A specific embodiment of the invention is directed toward the use of functionally active utron nucleic acids, preferably gene suppressing nucleic acids, and more preferably TSU nucleic acids, homologs and fragments thereof for cell replacement therapy, i.e., to provide cells which provide a function lacking or desired in a subject. In particular, gene therapy methods described below in Section 5.7 are used to introduce the utron nucleic acids of the invention into cells which provide a function lacking or desired in a subject, which cells are then transplanted into the subject. In a preferred embodiment, functionally active TSU nucleic acids are used so as to prevent the expression of MHC class I and class II antigens and/or ICAM-1, B7-1, B7-2, and FcγR antigens in non-autologous replacement cells, which replacement cells can then be administered as a therapeutic without co-administration of immunosuppressives.

Specifically, the present invention can be used to prepare replacement cells for the treatment of any disorder in which a cell function is lacking or defective in a subject.

A specific embodiment provides a method for the treatment of diabetes mellitus. Functionally active TSU nucleic acids are introduced into isolated normal pancreatic islet cells to prepare replacement islet cells. These replacement islet cells are then administered by the methods described in Section 5.7 or any method well-known in the art.

In another embodiment, TSU nucleic acids are used to suppress expression of MHC class I and II antigens and/or ICAM-1, B7-1, B7-2 and FcγR antigens in myoblasts. These myoblast replacement cells are then used in myoblast transfer therapy as a therapy for Duchene Muscular Dystrophy (see Bao et al., 1994, *Transplantation* 58:585–591; Law et al., 1994, *Transplantation Proceedings* 26:3381–3383). The myoblast replacement cells can also be used for treatment of any other muscular dystrophy or any other degenerative muscle disease.

In another specific embodiment, the TSU nucleic acid is introduced into fetal brain cells or neuroblastoma cells to prepare replacement cells for use in treatment of Parkinson's or any other neurodegenerative disorder.

In another embodiment, the TSU nucleic acid is introduced into keratinocytes to prepare replacement cells for the treatment of burns, wounds or other skin disorders.

In another embodiment, cells for use in cell replacement therapy, for example, keratinocytes, are made doubly recombinant by methods known in the art or described herein for the TSU nucleic acid and a gene encoding any protein lacking or desired in the subject. In particular, the cells made recombinant for the TSU nucleic acid can also contain a recombinant nucleic acid encoding and capable of expressing a product of value in the treatment of a disease or disorder, preferably a human disease or disorder. The doubly recombinant replacement cells are then administered as therapy for any disorder resulting from a defect in or lack of the protein produced by the doubly recombinant replacement cells. By way of example, but not limitation, an TSU-encoding nucleic acid can be introduced into a cell recombinantly expressing a desired hormone (e.g., growth hormone, insulin) or cytokine, which cell can then be administered in vivo in a patient.

5.6.1.1. ISOLATION OF CELLS FOR CELL REPLACEMENT THERAPY

Cells into which a nucleic acid can be introduced for purposes of cell replacement therapy encompass any desired, available cell type, and include, but are not limited to, epithelial cells, endothelial cells, keratinocytes, fibroblasts, muscle cells, myoblasts, hepatocytes, neuroblastoma cells; blood cells such as T lymphocytes, B lymphocytes, monocytes, macrophages, neutrophils, eosinophils, megakaryocytes, granulocytes; various stem or progenitor cells, in particular hematopoietic stem or progenitor cells, adult neural, embryonic neural, embryonic heart or embryonic liver cells, etc.

The isolation of replacement cells for use in the present invention can be carried out by any of numerous methods commonly known to those skilled in the art. For example, one common method for isolating replacement cells is to collect a population of cells from a subject and using differential antibody binding, wherein cells of one or more certain differentiation stages are bound by antibodies to differentiation antigens, fluorescence activated cell sorting is used to separate the desired precursor cells expressing selected differentiation antigens from the population of isolated cells.

In one embodiment of the invention, epithelial stem cells or keratinocytes are obtained from tissues such as the skin and the lining of the gut by known procedures (Rheinwald, 1980, *Meth. Cell Bio.* 21A:229). In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a subject can be grown in tissue culture (Rheinwald, 1980, *Meth. Cell Bio.* 21A:229; Pittelkow and Scott, 1986, *Mayo Clinic Proc.* 61:771).

In another embodiment of the invention, mesenchymal progenitor cells are used in cell replacement therapy. Mesenchymal progenitor cells give rise to a very large number of distinct tissues, for example chondrocytes, osteoblasts, cartilage and bone (Caplan, 1991, *J. Orth. Res.* 641–650). Conditions have been defined under which chick mesenchymal cells differentiated into chondrocytes and bone. (Caplan, 1970, *Exp. Cell. Res.* 62:341–355; Caplan, 1981, 39th Annual Symposium of the Society for Developmental Biology, pp. 37–68; Caplan et al., 1980, Dilatation of the Uterine Cervix 79–98; DeLuca et al., 1977, *J. Biol. Chem.* 252:6600–6608; Osdoby et al., 1979, *Dev. Biol.* 73:84–102; Syftestad et al., 1985, *Dev. Biol.* 110:275–283). Mesenchymal cells capable of differentiating into bone and cartilage have also been isolated from marrow (Caplan, 1991, *J. Orth. Res.* 641–650). Caplan et al., 1993, U.S. Pat. No. 5,226,914 describes an exemplary method for isolating mesenchymal stem cells from bone marrow. Furthermore, the isolation of human marrow and the demonstration that cells deriving from it can sustain osteogenesis has been described, e.g., by Bab et al., 1988, *Bone Mineral* 4:373–386.

Several bone marrow isolation protocols have been reported and can be used to obtain progenitor or precursor cells. Single cell suspensions from rat bone marrow can be prepared according to Goshima et al., 1991, *Clin. Orth. and Rel. Res.* 262:298–311. Human stem cell cultures from marrow can be prepared as described by Bab et al., 1988, *Bone Mineral* 4:373–386 as follows: Whole marrow cells are obtained from five patients. The marrow samples are separated from either the iliac crest or femoral midshaft. Marrow samples, 3 ml in volume, are transferred to 6 ml of serum-free Minimal Essential Medium (MEM) containing 50 U/ml penicillin and 0.05 mg/ml streptomycin-sulfate. A suspension of predominantly single cells is prepared as described previously (Bab et al., 1984, *Calcif. Tissue Int.* 36:77–82; Ashton et al., 1984, *Calcif. Tissue Int.* 36:83–86) by drawing the preparation into a syringe and expelling it several times sequentially through 19, 21, 23 and 25 gauge needles. The cells are counted using a fixed volume hemocytometer and the concentration adjusted to $1-5 \times 10^8$ total marrow cells per ml suspension. Positive and negative control cell suspensions can be set as described before (Shteyer et al., 1986, *Calcif. Tissue Int.* 39:49–54), using rabbit whole marrow and spleen cells, respectively.

The invention also relates to the use of neural replacement cells such as neuroblastoma cells, fetal neural cells and adult neural stem cells. For the preparation of fetal neural cells, fetal cells can be placed into primary culture using, for example, protocols developed by Sabate et al., 1995, *Nature Gen.* 9:256–260. By way of example, but not limitation, the procedure is as follows: Primary cultures of human fetal brain cells can be isolated from human fetuses, obtained from legal abortions after 5 to 12 weeks of gestation. Expulsion can be done by syringe-driven gentle aspiration under echographic control. Fetuses collected in sterile hibernation medium are dissected in a sterile hood under a stereomicroscope. Brains are first removed in toto in hibernation medium containing penicillin G 500 U/ml, streptomycin 100 µg/ml, and fungizone 5 µg/ml. For fetuses of six to eight weeks of age the brain is separated into an anterior (telencephalic vesicles and diencephalon) and a posterior fraction (mesencephalon, pons and cerebellar anlage) and a posterior in toto after careful removal of meninges. For older fetuses, striatal hippocampal, cortical and cerebellar zones expected to contain proliferative precursor cells are visualized under the stereomicroscope and dissected separately. Cells are transferred to either Opti-MEM (Gibco BRL) containing 15% heat-inactivated fetal bovine serum (FBS) (Seromed), or to a defined serum-free medium (DS-FM) with human recombinant bFGF (10 µg/ml, Boehringer), which is a minor modification of the Bottstein-Sato medium 39 with glucose, 6 g/l, glutamine 2 mM (Gibco BRL), insulin 25 ug/ml (Sigma) transferrin 100 µg/ml (Sigma), sodium selenite 30 nM (Gibco BRL), progesterone 20 nM (Sigma), putrescine 60 nM (Sigma), penicillin G (500 U/ml), streptomycin 100 µg/ml, and fungizone 5 µg/ml. Cells, approximately 40,000 per $cm^2$, are grown at 37° C. in an atmosphere containing 10% $CO_2$ in tissue culture dishes (Falcon or Nunc) coated with gelatin (0.25% wt/vol) followed by Matrigel (Gibco BRL, a basement membrane extract enriched in laminin and containing trace amounts of growth factors diluted one in 20).

The neuronal precursors from the adult brain can also be used as a source of cells for neuronal transplantation (see Alvarez-Buylla, 1993, *Proc. Natl. Acad. Sci. USA* 90:2074–2077). Neural crest cells have also been long recognized to be pluripotent neuronal cells which can migrate and differentiate into different cell neuronal cell types according to the instructions they receive from the microenvironment they find themselves in (LeDouarin and Ziller, 1993, *Curr. Opin. Cell Biol.* 5:1036–1043).

Any technique which provides for the isolation, propagation, and maintenance in vitro of hematopoietic stem cells (HSC) can also be used in therapeutic methods of the invention. Techniques by which this can be accomplished include (a) the isolation and establishment of HSC cultures from bone marrow cells isolated from a donor, or (b) the use of previously established long-term HSC cultures. In a particular embodiment of the present invention, human bone marrow cells can be obtained from the posterior iliac crest by needle aspiration (see, e.g., Kodo et al., 1984, *J. Clin. Invest.* 73:1377–1384). In a preferred embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., 1977, *J. Cell Physiol.* 91:335) or Witlock-Witte culture techniques (Witlock and Witte, 1982, *Proc. Natl. Acad. Sci. USA* 79:3608–3612).

Another technique for the isolation of HSC is described by Milner et al., 1994, *Blood* 83:2057–2062. Bone marrow samples are obtained and are separated by Ficoll-Hypaque density gradient centrifugation, are washed, and stained using two-color indirect immunofluorescent antibody binding and then separated by fluorescence-activated cell sorting (FACS). The cells are labelled simultaneously with IgG antibodies such that $CD34^+$ hematopoietic stem cells, including the immature subset that lacks expression of individual lineage associated antigens, $CD34^+lin^-$, are isolated from the cells collected from marrow.

Where hematopoietic progenitor cells are desired, the presence of hematopoietic progenitor cells and/or their progeny can be detected by commonly known in vitro colony forming assays (e.g., those that detect CFU-GM, BFU-E). As another example, assays for hematopoietic stem cells are also known in the art (e.g., spleen focus forming assays, assays that detect the ability to form progenitors after replating).

Liver stem cells can be isolated by methods described in PCT Publication WO 94/08598, dated Apr. 28, 1994.

5.6.2. USE IN TRANSPLANTATION

In a particular embodiment relating to the use of TSU nucleic acids and their derivatives and analogs, the present invention also relates to methods for inhibiting (preventing or reducing the likelihood of) transplant rejection in human or veterinary disorders treatable by non-autologous organ, tissue, or cell transplantation. In a preferred embodiment, the functional TSU nucleic acids, fragments, homologs or derivatives are used to prevent immuno-rejection of organ transplants, either allogeneic or xenogeneic transplants, including but not limited to heart, liver, kidney, lung, and skin transplants. To prevent immuno-rejection, a DNA expression construct encoding the TSU nucleic acid or any functional fragment, derivative or homolog is administered to the organ tissue, by any method described herein (see Section 5.7) or well-known in the art, before transplantation to prevent or reduce expression in the organ tissue of MHC class I and II antigens and/or ICAM-1, B7-1, B7-2, and FcγR antigens. In another embodiment, in addition or alternatively to the foregoing, the TSU nucleic acid therapeutic is administered to the patient or animal subject (transplant recipient) during and/or after transplantation to prevent MHC class I and II antigen and other antigen expression and concomitant organ rejection.

In another embodiment, functional TSU nucleic acids are used to prepare donor organs in non-human animals for use in xenogeneic transplants. In a preferred embodiment, the non-human animal, preferably a pig, expressing an TSU transgene is also transgenic for and capable of expressing non-polymorphic human MHC Class I antigen HLA-G, human $\beta_2$-microglobulin, and/or one or more of the genes selected from among those encoding human CD46, human CD55, and/or human CD59. Preferably, the transgenic animal expresses human TSU, HLA-G, $\beta_2$-microglobulin, and one or more of human CD46, CD55, and CD59. Breeding of TSU transgenic animals with other transgenic animals expressing non-polymorphic human MHC class I antigen HLA-G and human $\beta_2$-microglobulin, from suitable gene constructs, would provide protection against attack by human NK cells on MHC class I⁻ cells in these transgenic animals. Breeding of animals transgenic for TSU with other transgenic animals, respectively, expressing one or more of the human complement-inactivating proteins human CD46, human CD55, and/or human CD59, is expected to block the effects of natural antibodies in human recipients that might otherwise kill the xenografted cells and tissues via complement-mediated mechanisms. The non-human animals resulting from these breeding steps can provide donor organs for use in xenogeneic transplants.

In a preferred embodiment, pigs can be made transgenic for TSU as well as other genes necessary for production of donor organs in non-human animals using methods well-known in the art, such as, but not limited to, that described by Wheeler, PCT Application WO 94/26884 and Kumar et al., PCT Application WO 95/04744. For example, and not by way of limitation, transgenic non-human animals can be produced by microinjection of ova as described in Kumar et al., PCT Publication WO 95/04744. In particular, pigs transgenic for the gene promoter suppressing nucleic acids of the invention can be produced by this method, as follows:

Specifically, estrus is synchronized in sexually mature gilts by administering progestogen, e.g., allyl trenbolone (AT), at 15 mg/gilt/day for 12 to 14 days.

On the last day of receiving AT, gilts are administered two intramuscular injections of prostaglandin $F_{2\alpha}$ (Lutalyse at 10 mg/injection). Twenty-four hours later, donor gilts are given an intramuscular injection of pregnant mare serum gonadotrophin (PMSG) (1500 IU), and then eighty hours after the PMSG injection, an injection of human chorionic gonadotrophin (HCG) (750 IU). Donor gilts which exhibit estrus within 36 hours of HCG administration are then bred at 12 and 24 hours after the onset of estrus by either artificial or natural insemination.

Between 59 and 66 hours after the HCG injection, one- and two-cell ova are surgically removed from the donors. Specifically, the donors are anesthetized by administration of 0.5 mg acepromazine and 1.3 mg ketamine per kg body weight. Once the donor is anesthetized, the reproductive tract is exteriorized by a mid-ventral laparotomy, and then a drawn glass cannula (O.D. 5 mm, length 8 cm) is inserted into the ostium of the oviduct and anchored by a suture. The ova is flushed into the cannula by infusing sterile Dulbecco's phosphate buffered saline supplemented with 0.4% bovine serum albumin through a 20 g needle inserted into the lumen of the oviduct. The medium is collected and checked for the presence of ova by examination under a stereomicroscope at 50× power. The collected one- and two-cell ova is washed in Brinster's Modified Culture-3 medium (BMOC-3) supplemented with 1.5% BSA and stored in 50 μl drops of BMOC-3 medium under oil at 38° C. under a 90% $N_2$, 50% $O_2$, 5% $CO_2$ atmosphere until microinjection.

For microinjection, the collected ova are centrifuged in 1 ml HEPES medium supplemented with 1.5% BSA in an Eppendorf tube (15 ova per tube) for 6 minutes at 14000 g to visualize the pronuclei. Then, the ova are transferred to a 5–10 μl drop of HEPES medium under oil on a depression slide. Nucleic acid comprising an expression construct encoding the gene promoter suppressing nucleic acid (utron) (1 ng/μl in Tris-EDTA buffer) is then microinjected into the pronuclei of one-cell ova or both nuclei of two-cell ova using micromanipulators and a microscope with Nomarski optics. The ova are maintained under the above-described storage conditions for up to 10 hours.

Recipients, i.e., unbred, gilts which exhibit estrus within 24 hours of the donors are used for the embryo transfer.

The recipients are anesthetized and the oviduct exteriorized as described above. Ova in the BMOC-3 medium are aspirated into a 21 g×¾ butterfly infusion set connected to a 1 cc syringe. The tubing is fed into the oviduct through the ostium and the ova expelled through the tubing. The oviduct is then bathed in sterile 10% glycerol-0.9% saline solution and returned to the body and then the incision closed by standard methods.

The recipients are checked for pregnancy 35 days after estrus by ultrasound, and farrowing is induced with 2 injections of prostaglandin $F_{2\alpha}$ (10 mg/injection) after 112 days of gestation. The resulting piglets are checked for incorporation of the injected nucleic acid by analyzing genomic DNA extracted from tail tissue by any method known in the art for analysis of genomic DNA, such as southern blotting.

Also by way of example, and not by way of limitation, transgenic non-human animals can be produced using Embryonic Stem (ES) cells as described in Wheeler, PCT Publication WO 94/26884. In particular, chimeric ungulates, specifically pigs, containing a population of cells transgenic for a DNA expression construct encoding a gene promoter suppressing nucleic acid of the invention can be produced by this method as follows:

Specifically, embryos for the preparation of ES cells are collected from bred pigs at 5.5–8.0 days, from cows at 5.5 to 10 days, from sheep or goats at 5–9 days, after the onset of estrus using any method known in the art such as the method described above.

After collection, the embryos are washed three times with fresh culture medium. If the embryos have not hatched, they are transferred to microdrops of W-2 media under oil and culture to hatching. Hatched blastocysts are transferred to individual wells in a 24-well plate containing 1 ml of Stem Cell Media (SCM) if fibroblasts, e.g., mitomycin C-inactivated mouse embryonic fibroblasts, are used as a feeder layer or Conditioned Stem Cell Media (CSCM) if no feeder layer is used.

Once the isolated embryos have attached, the embryos are cultured until the inner cell mass (ICM) enlarges. After enlargement, the ICM is dislodged and washed twice with calcium/magnesium-free PBS and then incubated for 1–5 minutes in trypsin solution at 38° C. Cells are disaggregated by pipetting through a fine pasteur pipet and then transferred to a fresh drop of CSCM with 20% fetal calf serum (FCS) in a culture vessel, with or without a feeder layer.

The cultures are examined for colony formation, detectable as nestlike structures of round stem cells, which usually form after 7–8 days of culture. These colonies are isolated, dissociated and plated onto fresh feeder cells. The cells are subcultured in this fashion until an undifferentiated ES-cell line is established. Preliminarily, ES-cells should be small and rounded and contain large dark nuclei with one or more prominent nucleoli; and their undifferentiated character may be confirmed by indirect immunofluorescent staining for lack of the cytoskeletal structural proteins, cytokeratin 18 and vimentin.

Nucleic acids comprising the gene promoter suppressing nucleic acid (utron) are introduced into the ES cells by any method known in the art for introducing nucleic acids into cells, for example, those methods described in Section 5.7.

Chimeras are made by injecting approximately 5–20 ES-cells into the cell mass of a morula or blastocoele cavity of a blastocyst with a glass injection needle, 25–30μ in diameter. Chimeras can also be produced by nuclear transfer either by fusion of ES-cells or injection of ES-cell nuclei with enucleated, pre-implantation embryonic cells. These chimeric embryos are then introduced into recipients and allowed to develop to term as described above.

The resulting chimeric ungulates can then be bred to generate homozygous lines of ungulates transgenic for the gene promoter suppressing nucleic acid.

In another specific embodiment, mice transgenic for TSU are prepared. By way of example but not limitation:

Transgenic mice are prepared using standard methods of microinjection of the male pronuclei of fertilized oocytes. Animals are raised in isolation cages due to their predicted immunosuppression. Transgenic founder animals are inbred to homozygosity. Homozygosity is confirmed by Southern blot analysis and PCR analysis of genomic DNA.

The expression constructs used for the preparation of the TSU transgenic mice will have gene promoters appropriate for the desired tissue-related expression.

Powerful viral promoters like CMV are expected to give ubiquitous high level expression. A β-Actin or γ-actin promoter should give moderate level ubiquitous expression. An inducible promoter such as an HLA-DR promoter is expected to yield specific induction of expression under immune stimulation. A Factor VIII promoter is expected to yield expression particularly in the endothelial cells of the animal.

Murine MHC class I and MHC class II mRNA and antigen levels in tissues of the various lines of transgenic mice obtained with different gene constructs, both basal and interferon-γ stimulated, can be determined by Northern blot and immunocytochemical analysis.

The non-human animals that can be used include but are not limited to pigs, baboons, gorillas, chimps, horses, cows, sheep, goats, primates, mice, rats, etc. In a preferred embodiment, the TSU transgene is only expressed in specific tissues by virtue of a tissue-specific promoter as described in Section 5.6 or any such promoter known in the art. The organs of transgenic animal donors are then transplanted into the patient or animal recipient by methods well known in the art.

5.6.3. TREATMENT OF IMMUNE DISORDERS

In a particular embodiment relating to the use of TSU nucleic acids and their derivatives and analogs, the invention also relates to methods of treatment for immune disorders which can be prevented or treated by suppression of expression of MHC class I and II antigen and/or other cytokine-induced antigens (ICAM-1, B7-1, B7-2 and FcγR) in the tissue or cells in which the undesirable immune or inflammatory response occurs.

Such methods of treatment are carried out by gene therapy using TSU nucleic acids or their functionally active derivatives or fragments (see Section 5.7). In a preferred aspect, an expression vector that can be transcribed in vivo to produce an TSU RNA is directly administered to a patient in need of such treatment, preferably at the site of an inflammatory or autoimmune reaction. Patients include, but are not limited to, humans, and animals such as livestock and pets, e.g., cows, pigs, horses, dogs, cats, fowl, etc.

Specific embodiments are directed to autoimmune and inflammatory disorders associated with cytokine-induced antigens, such as MHC class I and II antigens, and STAT-responsive antigens, such as ICAM-1, B7-1, B7-2 and FcγR antigens, such as, but not limited to, Ankylosing spondylitis, Reiter's syndrome, acute anterior uveitis, reactive arthritis, rheumatoid arthritis, juvenile rheumatoid arthritis, systemic lupus erythematosus, Behcet's disease, Sjorgren's syndrome, Graves' disease, insulin-dependent diabetes mellitus, Celiac disease, psoriasis vulgaris, pemphigus vulgaris, dermatitis herpetiformis, idiopathic hemochromatosis, Goodpasture's syndrome, multiple sclerosis, myasthenia gravis, etc.

In a specific embodiment, an IL-2 gene repressor utron such as described in Section 8 hereinbelow is used to suppress activation of T lymphocytes caused by IL-2 and to result in generalized immunosuppression if administered so as to be expressed in T lymphocytes. It, thus, can be used for treatment of patients in which such immunosuppression is desired, e.g., patients having those disorders listed above, and patients undergoing or who have undergone bone marrow or umbilical cord blood transplants for hematopoietic reconstitution (e.g., after cancer chemotherapy or irradiation), and patients with other disorders wherein the drugs cyclosporin A and FK506 are presently used. 5.6.4. TREATMENT OF CANCER In an embodiment, the gene promoter suppressing nucleic acids of the invention are used to treat neoplastic disease. The gene promoter suppressing nucleic acids can be introduced into the subject by any of the means described infra. The subject can be a plant or an animal, or, preferably, a human. In a preferred embodiment, the gene promoter suppressing nucleic acid can be an oncogene promoter suppressor, by virtue of its containing a promoter motif of a promoter of an oncogene in the subject. In another preferred embodiment, the gene promoter suppressing nucleic acid can be a cell cycle control gene suppressor (e.g., a suppressor of the proliferating-cell nuclear antigen (PNCA) gene or of the cdc2 kinase gene (Morishita et al., 1993, Proc. Natl. Acad. Sci. USA 90:8474–8478), or a gene promoter suppressor that suppresses transcription from a viral promoter of a cancer-causing virus (e.g., the LTR of HIV, HTLV-1, HTLV-2). In yet another preferred embodiment, the targeting of the nucleic acids to the cancer cells can be aided by packaging in a retroviral vector such that the gene is expressed in growing cells, and in another preferred embodiment, the nucleic acid is operably linked to a tissue-specific promoter that itself is not suppressed by the gene promoter suppressing nucleic acid and is expressed in the cell type affected by the neoplastic disease. In another embodiment, the gene promoter suppressing nucleic acid is expressed under the control of a gene promoter for ubiquitous expression in the subject.

5.6.5. TREATMENT OF DISEASES CAUSED BY VIRUSES AND EUKARYOTIC PATHOGENS

In another embodiment, the gene promoter suppressing nucleic acids of the invention are used to treat diseases and disorders caused by a pathogen. The gene promoter suppressing nucleic acids can be introduced into the pathogen or cell or organism containing a cell infected with the pathogen to prevent expression of a gene which promotes the pathogenesis. The gene may be in the genome of either the pathogen or the host. The host may be an animal, either a human or non-human animal, afflicted with a virus, parasite, fungus, or other pathogen. The host may also be a plant, particularly an agricultural crop plant afflicted with a pathogen or pest, e.g., virus, fungus or insect. Thus, in a specific embodiment, a utron is used that contains a promoter regulatory motif of a gene of a pathogen.

In this embodiment, the utron of the invention contains a promoter regulatory motif that allows it to suppress the expression of a molecule needed by the pathogen in its life cycle. For example, to suppress HIV expression and thus replication, a protein-binding HIV promoter motif and/or nucleic acid motif that binds an HIV transcription factor is used as the promoter regulatory motif.

In a specific embodiment, an HIV-1 LTR repressor utron such as described in Section 9 hereinbelow is used to treat HIV infection and its sequelae such as AIDS-related complex and AIDS.

5.6.6. USE IN REGULATING BACTERIAL GENES

In a specific embodiment, nucleic acids consisting of or comprising a gene promoter suppressing sequence, are introduced by methods known in the art into bacterial cells for suppression of the function of a sigma factor or factors involved in gene expression in the bacteria, or for suppression of a specific bacterial gene repressor or repressors that act on certain bacterial operons, such as the lactose operon of E. coli, the tryptophan operon of E. coli, or other genes of E. coli and other bacteria, such as pathogenic bacteria. Such suppression of bacterial gene expression can have therapeutic use where the bacteria is a pathogen, e.g., Staphylococcus aureau, M. tuberculosis, Streptococcus pneumoniae, Haemophilus influenzae, e.g., of human or animals.

5.7. GENE THERAPY

In a specific embodiment, nucleic acids consisting of or comprising a gene promoter suppressing sequence, preferably an TSU sequence, or functional derivative thereof, are administered to provide gene promoter suppressing function, by way of gene therapy. Gene therapy refers to therapy performed by the administration of a nucleic acid to a subject. In this embodiment of the invention, the nucleic acid produces an RNA that mediates a therapeutic effect by providing gene promoter suppressing, preferably TSU, function. In a preferred embodiment in which an TSU nucleic acid is provided, TSU function is provided to suppress MHC Class I and/or Class II expression and/or ICAM-1, B7-1, B7-2 and/or FcγR expression, thereby inhibiting transplant rejection. For example, any of the methods for gene therapy available in the art can be used according to the present invention. Exemplary methods are described below.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5) :155–215. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, the gene promoter suppressing nucleic acid is part of an expression vector that transcribes the gene promoter suppressing RNA or fragment thereof in a suitable host. In particular, such a nucleic acid has a promoter operably linked to the functional gene promoter suppressing region, said promoter being inducible or constitutive, and, optionally, tissue-specific. In another particular embodiment, a nucleic acid molecule is used in which the gene promoter suppressing sequences and any other desired sequences are flanked by regions that promote homologous recombination at a desired site in the genome, thus providing for intrachromosomal expression of the utron nucleic acid (Koller and Smithies, 1989, *Proc. Natl. Acad. Sci. USA* 86:8932–8935; Zijlstra et al., 1989, *Nature* 342:435–438).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient for cell replacement therapy. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the cell or nucleus, e.g., by administering it in linkage to a ligand subject to receptor-mediated endocytosis (see e.g., Wu and Wu, 1987, *J. Biol. Chem.* 262:4429–4432) (which can be used to target cell types specifically expressing the receptors), etc. In a specific embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). In another embodiment, a nucleic acid-ligand complex can be formed in which the ligand comprises a fusogenic viral peptide to disrupt endosomes, allowing the nucleic acid to avoid lysosomal degradation. Alternatively, the nucleic acid can be introduced intracellularly and incorporated within host cell DNA for expression, by homologous recombination (Koller and Smithies, 1989, *Proc. Natl. Acad. Sci. USA* 86:8932–8935; Zijlstra et al., 1989, *Nature* 342:435–438).

In a specific embodiment, a viral vector that contains the gene promoter suppressing nucleic acid is used. For example, a retroviral vector can be used (see Miller et al., 1993, *Meth. Enzymol.* 217:581–599). These retroviral vectors have been modified to delete retroviral sequences that are not necessary for packaging of the viral genome. Retroviral vectors are maintained in infected cells by integration into genomic sites upon cell division. The nucleic acid to be used in gene therapy is cloned into the vector, which facilitates delivery of the gene into a patient. More detail about retroviral vectors can be found in Boesen et al., 1994, *Biotherapy* 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, *J. Clin. Invest.* 93:644–651; Kiem et al., 1994, *Blood* 83:1467–1473; Salmons and Gunzberg, 1993, *Human Gene Therapy* 4:129–141; and Grossman and Wilson, 1993, *Curr. Opin. in Genetics and Devel.* 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, *Current Opinion in Genetics and Development* 3:499–503 present a review of adenovirus-based gene therapy. Bout et al., 1994, *Human Gene Therapy* 5:3–10 demonstrated the use of adenovirus vectors to transfer genes to the respiratory epithelia of rhesus monkeys. Other instances of the use of adenoviruses in gene therapy can be found in Rosenfeld et al., 1991, *Science* 252:431–434; Rosenfeld et al., 1992, *Cell* 68:143–155; and Mastrangeli et al., 1993, *J. Clin. Invest.* 91:225–234.

Adeno-associated virus (AAV) has also been proposed for use in gene therapy (Walsh et al., 1993, *Proc. Soc. Exp. Biol. Med.* 204:289–300. Herpes viruses are other viruses that can also be used.

Another approach to gene therapy, for use in the cell replacement therapy of the invention, involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including, but not limited to, transfection, electroporation, microinjection, infection with a viral vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, *Meth. Enzymol.* 217:599–618; Cohen et al., 1993, *Meth. Enzymol.* 217:618–644; Cline, 1985, *Pharmac. Ther.* 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells (e.g., keratinocytes) may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled in the art.

In an embodiment in which recombinant cells are used in gene therapy, a gene promoter suppressing nucleic acid is introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention.

5.8. PHARMACEUTICAL COMPOSITIONS AND ADMINISTRATION

The invention provides methods of treatment by administration to a subject of a pharmaceutical (therapeutic) composition comprising a utron, preferably a gene promoter suppressing, more preferably an TSU, nucleic acid or fragment thereof. In particular the pharmaceutical compositions are comprised of replacement cells recombinant for utrons, e.g., utron RNA or DNA, utron oligonucleotides, or utron nucleic acid wherein a nucleotide sequence that can be transcribed to produce a utron RNA is operably linked to a promoter.

In one embodiment, the invention provides methods of treatment by administration to a subject of a pharmaceutical (therapeutic) composition comprising a therapeutically effective amount of a cell recombinant for a utron nucleic acid. The recombinant replacement cell envisioned for therapeutic use is referred to hereinafter as a "Therapeutic" or "Therapeutic of the invention." In a preferred aspect, the Therapeutic is substantially purified. The subject is preferably an animal, including, but not limited to, animals such as cows, pigs, horses, chickens, cats, dogs, etc., and is preferably a mammal, and most preferably human.

The replacement cells of the present invention can be transplanted into a patient for the treatment of disease or injury or for gene therapy by any method known in the art which is appropriate for the type of stem cells being transplanted and the transplant site. Hematopoietic stem cells can be transplanted intravenously, as can liver stem cells which will locate to the liver. Neural stem cells can be transplanted directly into the brain at the site of injury or disease.

The following describes exemplary methods which can be modified for the transplantation of replacement cells: Protocols for the isolation and transplantation of fetal tissues in humans have been reported and clinical trials involving these studies having been carried out. For example, Lindvall et al., 1990, *Science* 247:574–577, have described results regarding grafts and survival of fetal dopamine neurons after transplantation into brain. Rinsing and partial dissociation of precursor cells, if necessary, can be carried out by a modification of that described in Lindvall et al., 1989, *Arch. Neurol.* 46:615.

By way of example, implantation of cells into the brain can be performed as follows. Implantation is done at three sites in the left putamen with a stereotactic technique (Lindvall et al., 1989, *Arch. Neurol.* 46:615). For each site, 20 μl of the dissociated cells is drawn into the instrument (outer diameter, 1.0 mm). The cells are injected along a 10, 12 and 14 mm linear tract, respectively, in either 2.5 μl portions for 15 to 20 seconds each. Between each injection there is a 2 minute delay, and the cannula is then retracted 1.5 to 1.7 mm. After the final injection, the cannula is left in situ for 8 minutes before being slowly withdrawn from the brain. After surgery the cell viability is assessed following the procedure of Brundin et al., 1985, *Brain. Res.* 331:251.

Another example is outlined by Caplan et al., 1993, U.S. Pat. No. 5,226,914. Briefly, after marrow cells are harvested from bone marrow plugs and the marrow mesenchymal, stem cells are separated by centrifugation. The stem cells are isolated further by selective adherence to the plastic or glass surface of a tissue culture dish. The stem cells are allowed to proliferate, but not differentiate. Porous ceramic cubes composed of 60% hydroxyapatite and 40% β-tricalcium phosphate are added to the cells under a slight vacuum. The cubes with adhered cells are implanted into incisional pockets along the backs of nude mice. The mesenchymal stem cells differentiate into bone.

The titer of stem cells transplanted or the amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances.

In another embodiment, the pharmaceutical composition is comprised of utron nucleic acids, preferably gene promoter suppressing nucleic acids, more preferably TSU nucleic acids.

The pharmaceutical compositions of the present invention comprise a therapeutically effective amount of a Therapeutic, and a pharmaceutically acceptable carrier or excipient. Such a carrier includes, but is not limited to, saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, or emulsion.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

Methods of introduction include, but are not limited to, oral, intradermal, intramuscular, intraperitoneal, intravenous, subcutaneous, intranasal, and epidural routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the Therapeutics of the invention locally to the area in need of treatment or to an organ to be used for transplantation; this may be achieved by, for example, and not by way of limitation, local infusion before and during surgery, topical application, e.g., in conjunction with a wound dressing after surgery, by injection, by means of a catheter, or by means of an implant, said implant being of a porous, non-porous, or gelatinous material, including membranes, such as sialastic membranes, or fibers.

In a specific embodiment, pharmaceutical compositions comprising utron, preferably gene promoter suppressing nucleic acid, and more preferably TSU nucleic acids, are administered via liposomes, microparticles, or microcapsules. In various embodiments of the invention, it may be useful to use such compositions to achieve sustained release of the utron nucleic acids.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use of sale of pharmaceuticals or biological products, which notice reflects approval by the agency of manufacture, use or sale for human administration.

5.9. DIAGNOSTIC AND MONITORING USES

Utron, preferably gene promoter suppressing, and more preferably TSU, nucleic acids (and sequences complementary thereto) have uses in diagnostics. Such molecules can be used in assays, such as nucleic acid hybridization assays in which utron sequences and subsequences, including complementary sequences thereof, comprising about at least 8 nucleotides, preferably at least 15 nucleotides, can be used as hybridization probes. Hybridization assays can be used to detect, prognose, diagnose, or monitor conditions, disorders, or disease states associated with utron expression and/or activity as described supra, e.g., those diseases and disorders subject to therapy by administration of utrons of the invention or by administration of cells or tissue recombinantly expressing the same. In particular, such a hybridization assay is carried out by a method comprising contacting a sample containing nucleic acid with a nucleic acid probe capable of hybridizing to the DNA or RNA of the invention, under conditions such that hybridization can occur, and detecting or measuring any resulting hybridization.

In particular, such assays can be used to monitor the effect of therapeutic treatment with utrons. For example, when an expression vector that can be transcribed to produce an TSU nucleic acid is administered to a patient, a sample of RNA from the patient can be subjected to a hybridization assay to measure TSU production. Alternatively to measuring TSU production, the levels of a protein modulated directly or indirectly by TSU (e.g., MHC antigen, ICAM-1, B7-1, B7-2, FcγR, or the cytokines described in Section 5 hereof) or the RNA that encodes the protein can be detected or measured.

For example, a decrease in such levels or an increase in the level of TSU, relative to those levels present prior to administration of TSU DNA, RNA, or a functionally active derivative or analog thereof, or expression construct encoding the same, may indicate the efficacy of the administration.

In another specific embodiment, assays detecting or measuring TSU expression can be used to determine if a fetus is at risk for immunorejection by the mother, with increased expression of TSU relative to standard levels in which immunorejection generally does not occur being indicative of a risk of immunorejection.

6. TROPHOBLASTS EXPRESS DOMINANT, TRANSACTING FACTOR(S) THAT SILENCE THE CONSTITUTIVE AND INTERFERON-γ-INDUCIBLE EXPRESSION OF MAJOR HISTOCOMPATIBILITY COMPLEX CLASS I AND II ANTIGENS

Trophoblasts form a major histocompatibility complex (MHC) antigen-negative barrier that protects the semiallogeneic fetus from maternal cell-mediated immune attack. The constitutive expression of the polymorphic MHC class I genes, which is common to most tissues, is absent from trophoblasts. Interferon-γ stimulation of expression of MHC class I or class II genes, which occurs in many other cell types, does not occur in trophoblasts. As described herein, we have transfected into the trophoblast cell line Jar an MHC class II gene promoter driving the expression of a toxic reporter gene, and have demonstrated the presence of trans-acting suppressive factors by cell survival. Transient heterokaryons were generated with Jar trophoblast cells and MHC class II-positive Raji B lymphoblast cells, and dominant, trans-acting suppression by trophoblast factor(s) was observed. Thus, this evidence suggests that trophoblasts express dominant, trans-acting MHC silencers. Section 7, infra, describes the cloning of a cDNA encoding such an MHC silencer.

6.1. MATERIALS AND METHODS

Preparation of stable pDRA-TK-transfectant clones of HeLa carcinoma and Jar trophoblast cells and testing for promoter activity by ganciclovir killing.

The 2.4 kb 5'-promoter/enhancer region of the HLA-DRA gene (McKnight, 1980, *Nuc. Acids Res.* 8:5949–64) upstream of the 1.7 kb herpes simplex virus thymidine kinase gene (Loh et al., 1992, *EMBO J.* 11:1354–63), cloned into the pGEM-3Zf(-) vector to form plasmid pDRA, was kindly provided by R. A. Flavell (Yale Univ.) (Kriegler, 1990, *Gene Transfer and Expression: A Laboratory Manual* (Stockton Press, NY)). Stably transfected clones were prepared as described (Kriegler, 1990, *Gene Transfer and Expression: A Laboratory Manual* (Stockton Press, NY); Southern and Berg, 1982, *J. Mol. Appln. Gen.* 1:327–340) using Jar (Peyman and Hammond, 1992, *J. Immunol.* 149:2675–80) and HeLa clone 6 cells co-transfected with the positive selectable marker pSV2-Neo (Harlow and Lane, 1988, *Antibodies: A Laboratory Manual* (Cold Spring Harbor Press, Cold Spring Harbor, N.Y.)) (provided by D. DiMaio, Yale Univ.). HeLa clone 6 is an IFN-γ-responsive untreated subclone of the original HeLa cell line cultured as described (Peyman and Hammond, 1992, *J. Immunol.* 149:2675–80) Transfectant clones were isolated by limiting dilution and expanded in bulk culture (Sambrook et al., 1989, *Molecular Cloning: A Laboratory Manual* (Cold Spring Harbor Laboratory Press, Cold Spring Harbor, N.Y.)) in medium containing 600 μg/ml of the neomycin analog G418 (GIBCO BRL). Three stable HeLa-pDRA-TK clones (A1, A4, and B11), and five stable Jar-pDRA-TK clones (3D1, 3D3, 8C4, 8D1, and 8D2) were analyzed for transfected gene content and IFN-γ-stimulated ganciclovir sensitivity (Loh et al., 1992, *EMBO J.* 11:1351–1363). Integration of the TK gene was confirmed by PCR amplification using genomic DNA isolated from each cell line (Sambrook et al., 1989, *Molecular Cloning: A Laboratory Manual* (Cold Spring Harbor Laboratory Press, Cold Spring Harbor, N.Y.) as template with primers TK1, 5'-TTATTGCCGTCATAGCGCGG-3' (SEQ ID NO:21), and TK2, 5'-GGCGACCTGTATAACGTGTT-3' (SEQ ID NO:22) (Kaye et al., 1991, *Brit. J. Opthamol.* 75:195–200). Growth curves were determined for the parental cell lines and the transfectants. Aliquots of $1 \times 10^4$ cells were treated in 24-well plates with 200 U/ml recombinant human IFN-γ (Boehringer-Mannheim) with 0, 50, 150, or 250 nM ganciclovir in complete medium (Loh et al., 1992, *EMBO J.* 11:1351–1363) for two days, and then treated with ganciclovir-containing medium for an additional 2 days. Ganciclovir was provided by Syntex Corp. The selective medium was replaced with non-selective medium at 4 days.

Cells were harvested for counting at 1, 2, 4, 6, 8, and 10 days. Cell number was determined by a semi-quantitative calorimetric assay (Pierschbacher and Ruoslahti, 1984, *Proc. Natl. Acad. Sci.* 81:5985–88) in which the $A_{600}$ of solubilized samples of fixed, toluidine blue-stained cells were determined in a microtiter plate reader. Identical growth curves for these clones were obtained in duplicate experiments.

Fusion of trophoblast and lymphoblast cell lines and determination of HLA-DR expression by flow cytometry.

Non-expressing fusion partners, Jar cells and HeLa cells not treated with IFN-γ, were chemically labeled with 5 μM 5- and 6-carboxyfluorescein diacetate succinimidyl ester (CFSE) (Molecular Probes) before fusion with Raji cells. The dye did not affect viability, and the labeling intensity was sufficient for detection after a 40 h culture period. Heterokaryons were formed with polyethylene glycol (Ono et al., *J. Exp. Med.* 173:629–637). Co-cultured Jar and Raji cells as well as co-cultured HeLa and Raji cells were also analyzed without fusion. After two days the resultant steady-state levels of HLA-DR antigen were determined by staining the lightly-trypsinized live cell mixtures at 4° C. with L243 mAb ($IgG_{2a}$ isotype) (Peyman and Hammond, 1992, *J. Immunol.* 149:2675–80) and R-phycoerythrin-labeled goat anti-mouse IgG (Molecular Probes) with detection by flow cytometry using a FACS IV (Becton-Dickinson). Singly labeled red and green fluorescent cells were used to calibrate the instrument, and normal mouse $IgG_{2a}$ was used as a negative control for the red channel. Unlabeled Jar and unlabeled HeLa cells provided the negative controls for the green channel. Fused HLA-DR-positive cells appeared in the upper right quadrant.

6.2. RESULTS

Figure 1C:
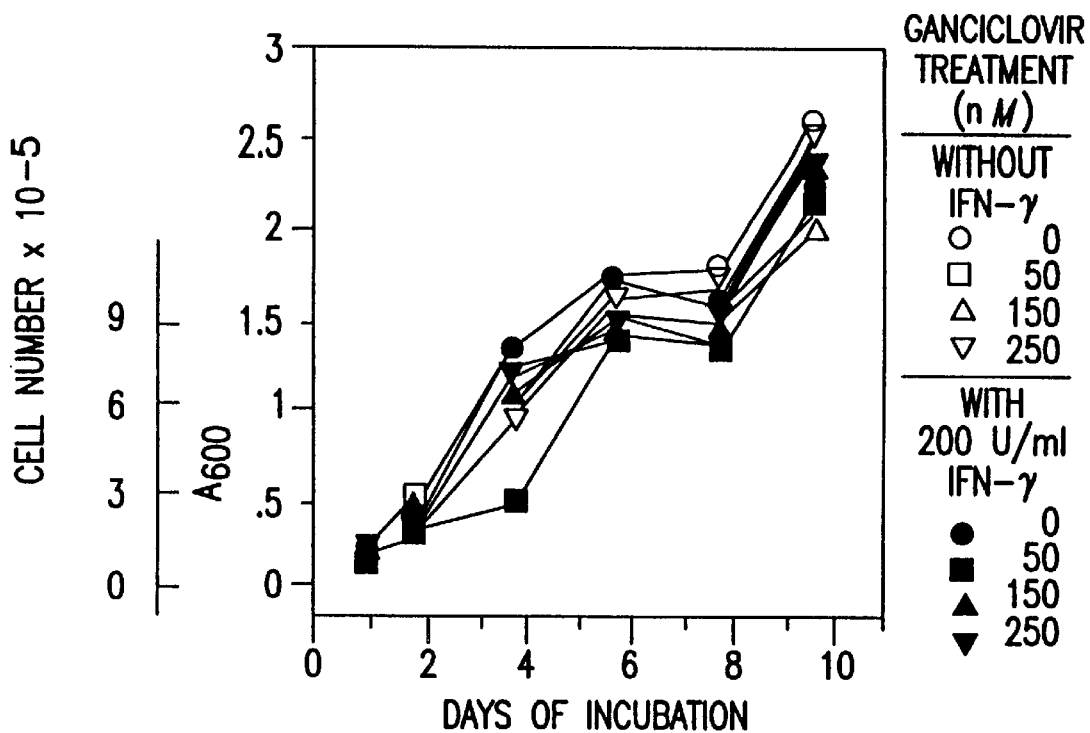
Figure 1D:
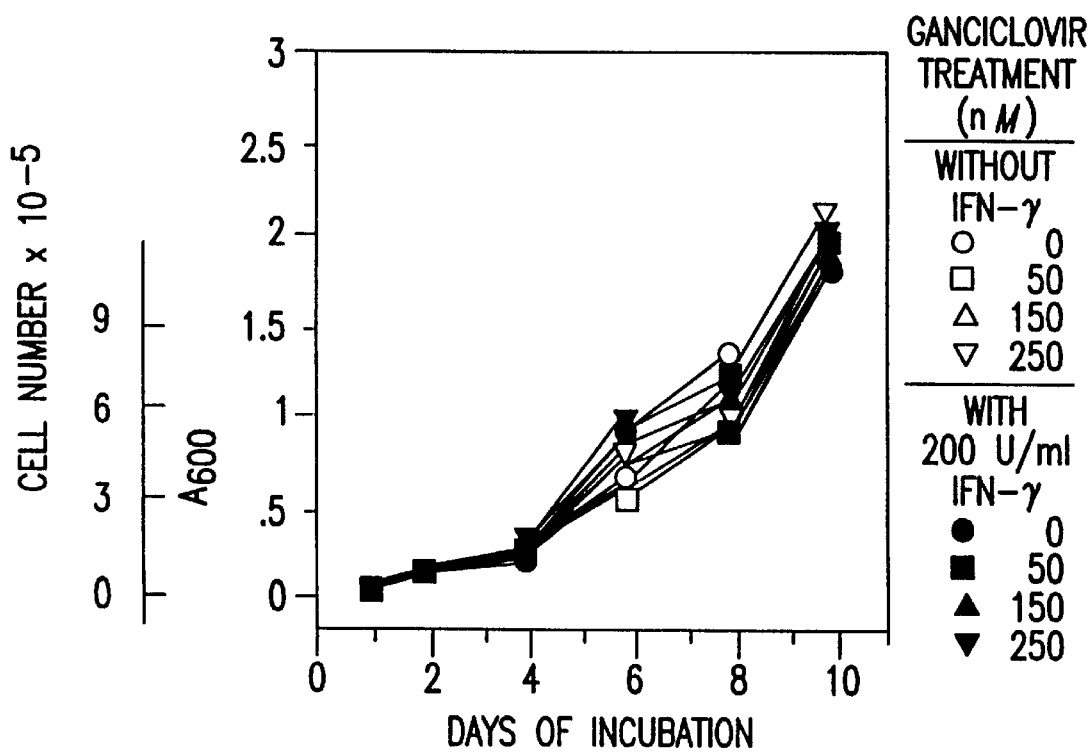

The continued growth of Jar trophoblast cells and HeLa carcinoma cells and of the Jar-pDRA-TK stable transfectants after treatment with IFN-γ and ganciclovir is contrasted by the negative selection of the HeLa-pDRA-TK stable transfectants under the same conditions (FIGS. 1A–D). Uritransfected HeLa clone 6 cells (FIG. 1A) survived all combinations of IFN-γ and ganciclovir, while the three HeLa-pDRA-TK clones (represented by clone A1 in FIG. 1B) responded to IFN-γ by activating the transfected HLA-DRA promoter and producing levels of TK mRNA and protein that caused doses of ganciclovir above 0 to be cytotoxic to approximately 100% of the cells by day 10 (solid squares, triangles, and inverted triangles). The HeLa-pDRA-TK clones were resistant to ganciclovir in the absence of IFN-γ (FIG. 1B, open squares, triangles, and inverted triangles). FIG. 1C indicates that untransfected Jar cells survived all doses of ganciclovir used with or without IFN-γ. The five Jar-pDRA-TK clones tested (represented by clone 3D1 in FIG. 1D) likewise did not exhibit any activation of the transfected gene promoter, and these clones thrived with IFN-γ and ganciclovir treatment up to the highest dose tested (FIG. 1D, solid symbols). Ganciclovir treatment alone did not affect survival of the Jar-pDRA-TK clones (FIG. 1D, open symbols). The results shown in FIG. 2 confirmed that genomic DNA from the transfected HeLa and Jar clones studied contained the viral TK gene, indicated by the PCR product of 278 bp. The identity of this gel band was confirmed in each case by SmaI cleavage of the PCR product to give the predicted 205 bp and 73 bp fragments. It was found in experiments not shown in FIG. 2 that the two other HeLa and the four other Jar transfectant clones studied also contained the integrated TK gene. A positive control using the pDRA-TK plasmid DNA gave the predicted band of 278 bp (not shown), and negative controls with untransfected HeLa clone 6 genomic DNA or with no primers in the reaction gave no products (not shown). Therefore, the artificially introduced HLA-DRA gene promoter/enhancer acts as a target for endogenous transacting suppressive factors in the Jar cell line.

Figure 3A:
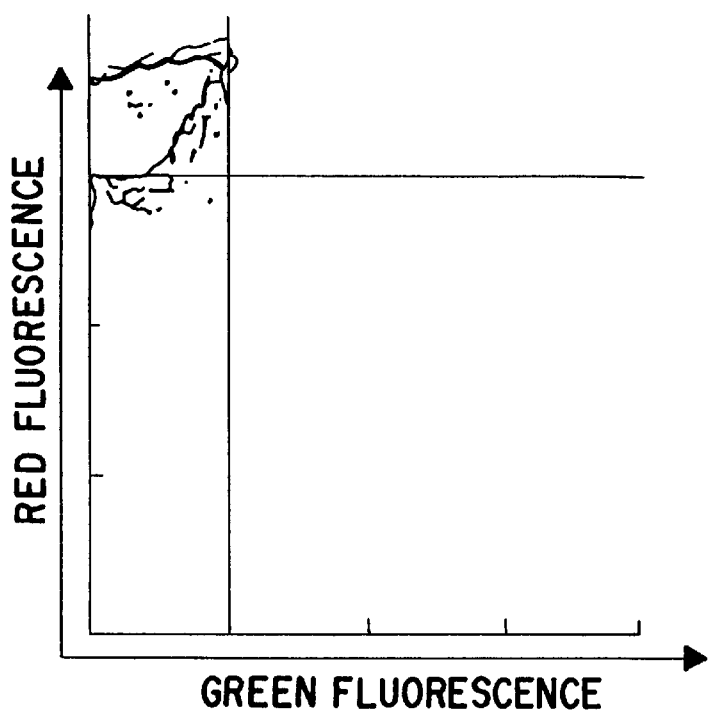
Figure 3B:
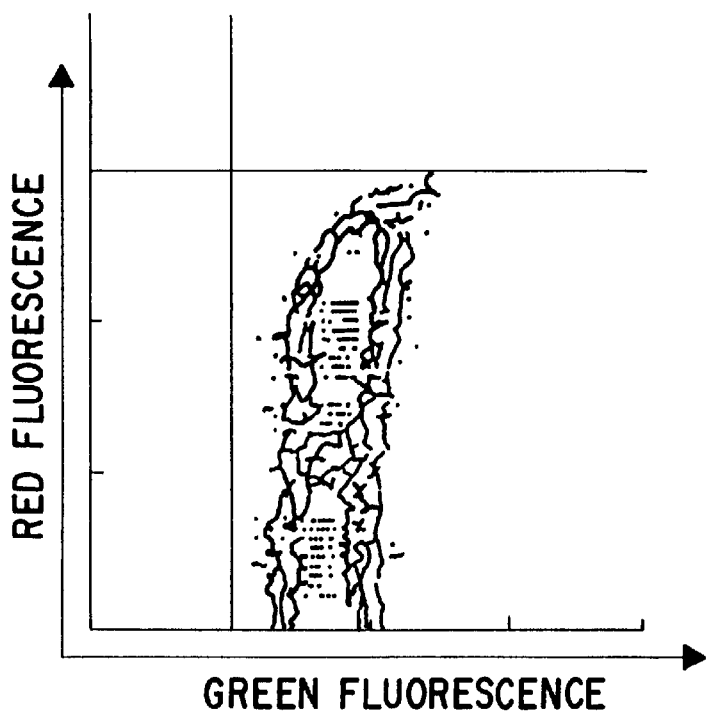
Figure 3C:
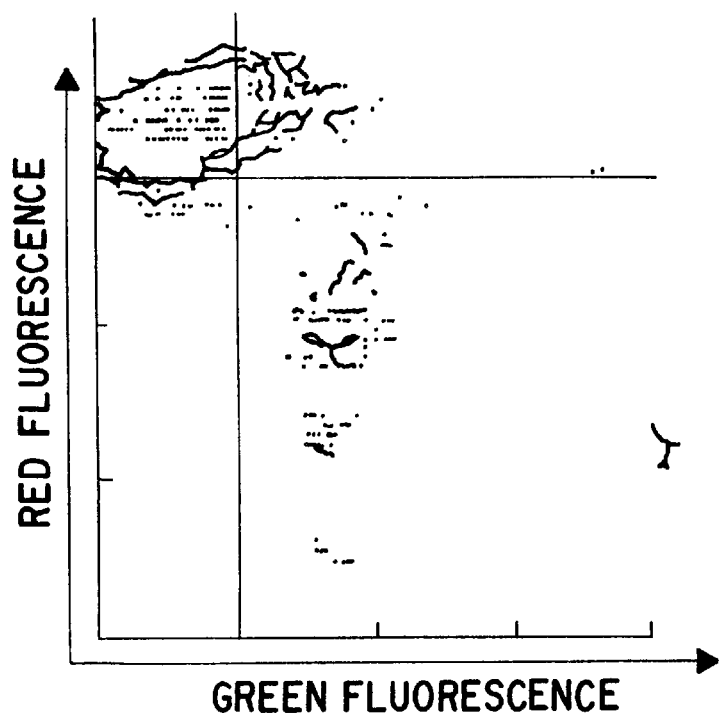
Figure 3D:
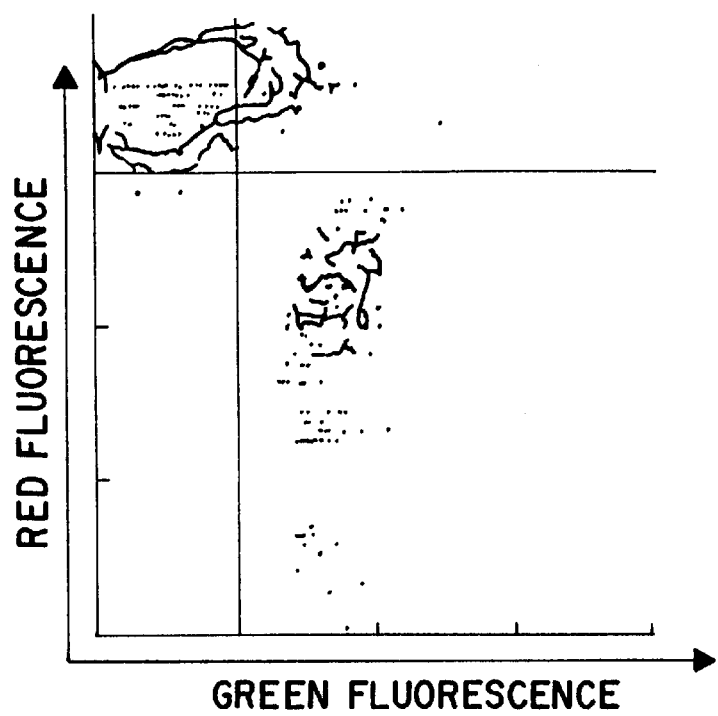
Figure 3E:
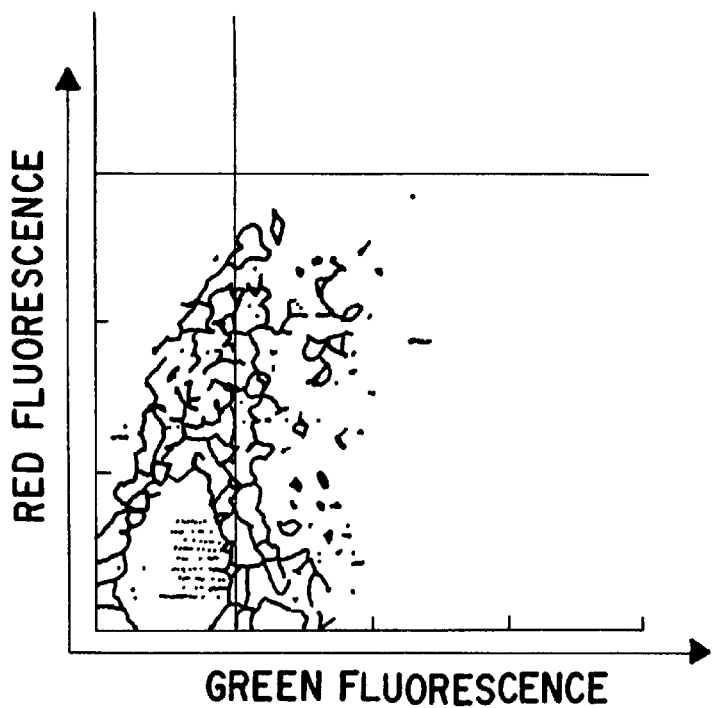
Figure 3F:
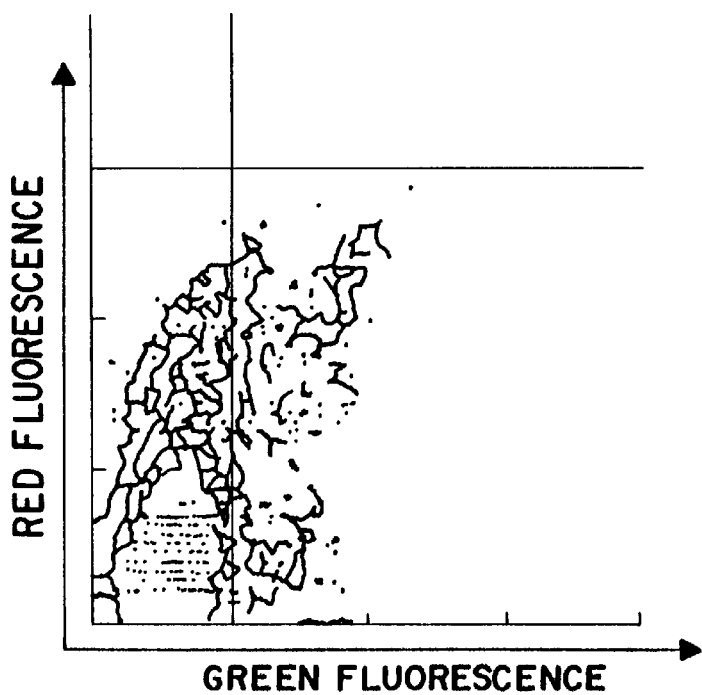
Figure 3G:
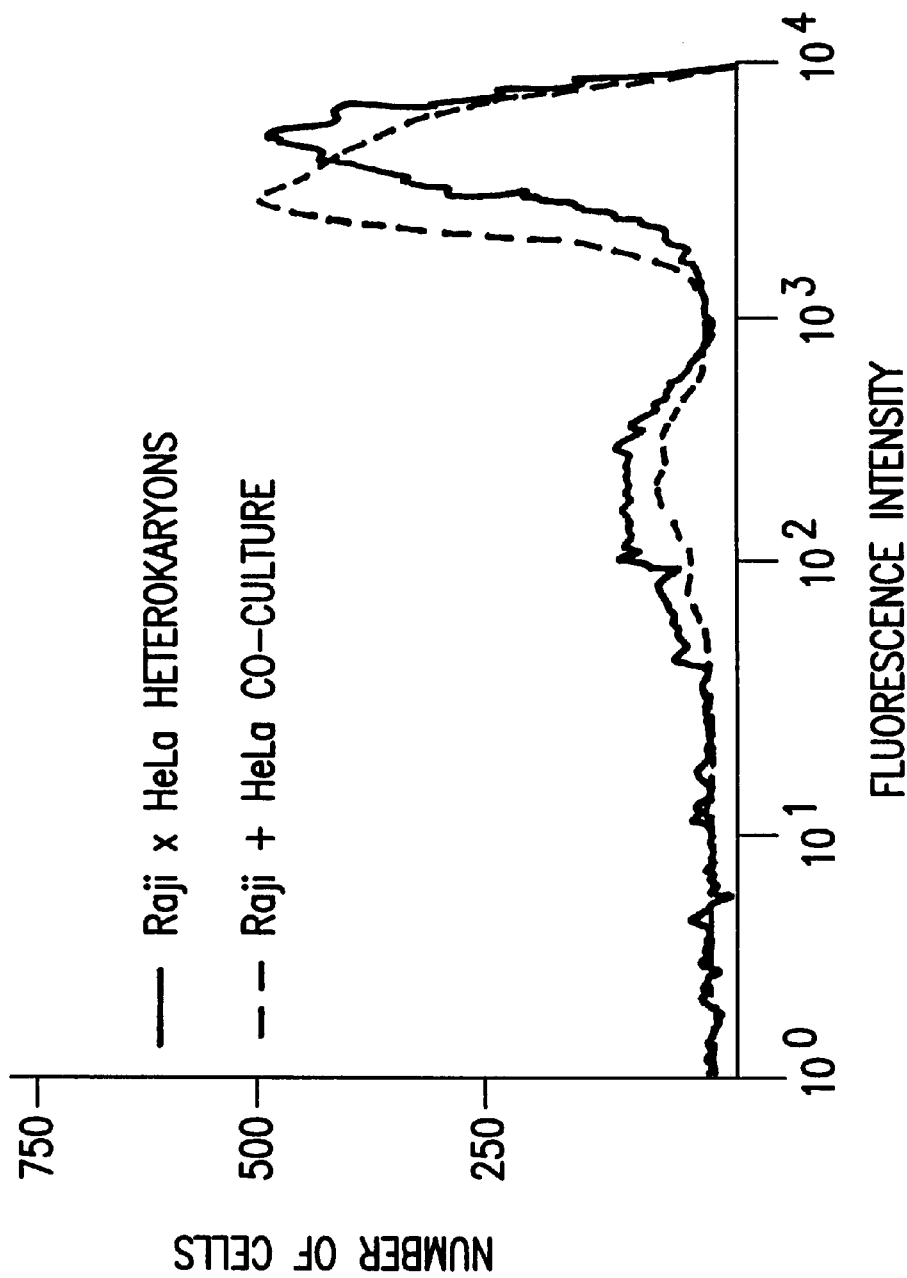

Transient heterokaryons were prepared by fusing Raji cells and Jar cells to determine if the MHC class II suppression in the trophoblast cell line was dominant or recessive relative to MHC class II expression in the B lymphocyte line. HLA-DR antigen expression was determined by flow cytometry of surface-labeled cells shown in FIGS. 3A–G and FIGS. 4A–G. Fusions of Raji cells and uninduced HeLa cells served as negative controls. High levels of HLA-DR antigen were observed on the cells in the Raji+HeLa co-culture, the Raji+Jar co-culture, and the Raji×HeLa heterokaryon sample (Upper right quadrants of FIGS. 3C, 4C, and 3D). In the Raji×Jar heterokaryons, however, the levels of HLA-DR antigen were significantly reduced (Upper right quadrant of FIG. 4D). When the data in the two right-hand quadrants of FIGS. 3C, 3D, 4C, and 4D were replotted as cell numbers versus red fluorescence intensity (HLA-DR antigen), gating on the CFSE-labeled cells, the results showed that few Raji×Jar heterokaryons maintained high HLA-DR antigen levels (FIG. 4G, solid line) compared to the co-culture sample (FIG. 4G, broken line), whereas in the negative control Raji×HeLa heterokaryons (FIG. 3G, solid line) the levels of HLA-DR antigen were similar to hose in the co-cultured cells (FIG. 3G, broken line).

6.3. DISCUSSION

Two types of experiments were performed to test the mechanism of suppression of MHC class II genes in human trophoblasts: expression driven by a transfected MHC class II promoter of a reporter gene in trophoblasts and expression of endogenous B lymphocyte MHC class II genes in transient heterokaryons with trophoblasts. We have previously shown that the trophoblast cell line Jar coordinately down-regulates levels of mRNA for MHC class II genes by an intracellular mechanism (Peyman and Hammond, 1992, *J. Immunol.* 149:2675–80). Data shown here suggest that the trophoblast cell line Jar expresses: 1) trans-acting factor(s) that silence the HLA-DRA gene promoter/enhancer, and 2) dominant trans-acting factor(s) that suppress constitutive production of HLA-DR antigen. Taken together, these lines of evidence are consistent with the idea that trophoblasts express one or more regulatory genes that encode dominant trans-acting factors which silence the constitutive and IFN-γ-inducible expression of MHC genes. This mechanism, observed in a trophoblast cell line, may also have physiological relevance in the normal placenta.

The transfected HLA-DRA gene promoter was inactive in Jar cells, like the endogenous gene, and this result eliminated the possibility that the mechanism of MHC class II suppression occurs exclusively by developmentally programmed chromosomal condensation or other cis-regulatory effects. This result suggests that mRNA turnover is not the major mechanism for the maintenance of undetectable steady-state levels of MHC class II mRNA, since TK was also suppressed in trophoblasts.

Figure 4A:
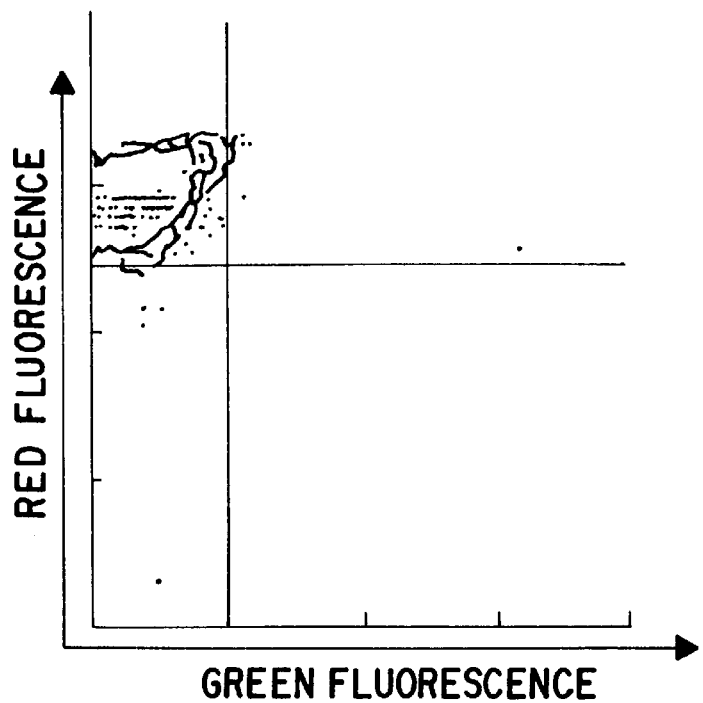
Figure 4B:
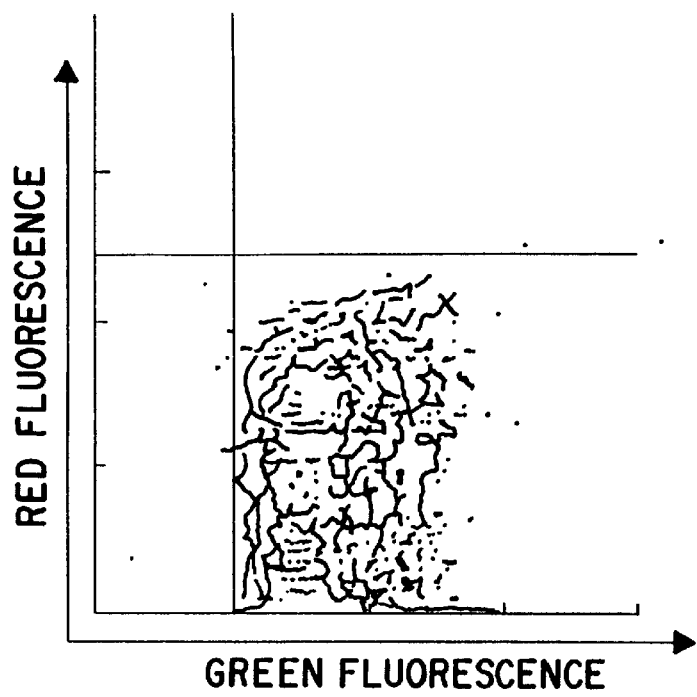
Figure 4C:
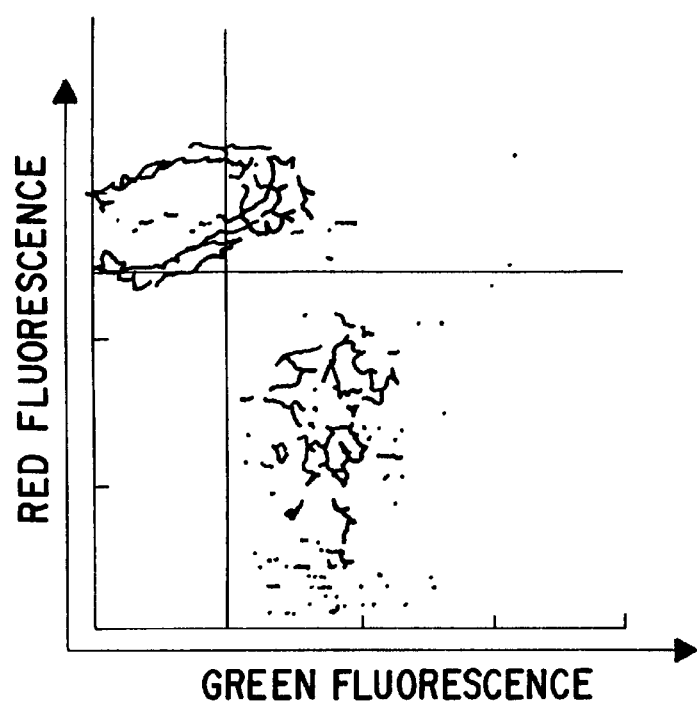
Figure 4D:
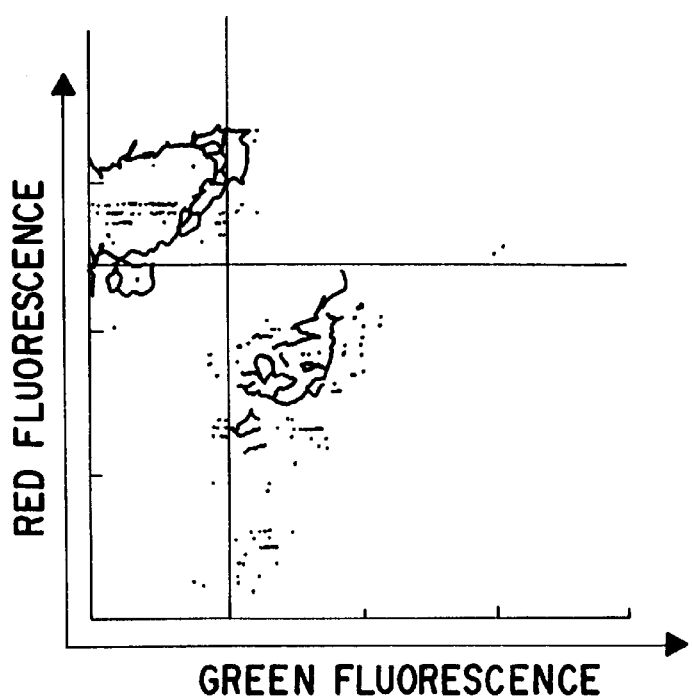
Figure 4E:
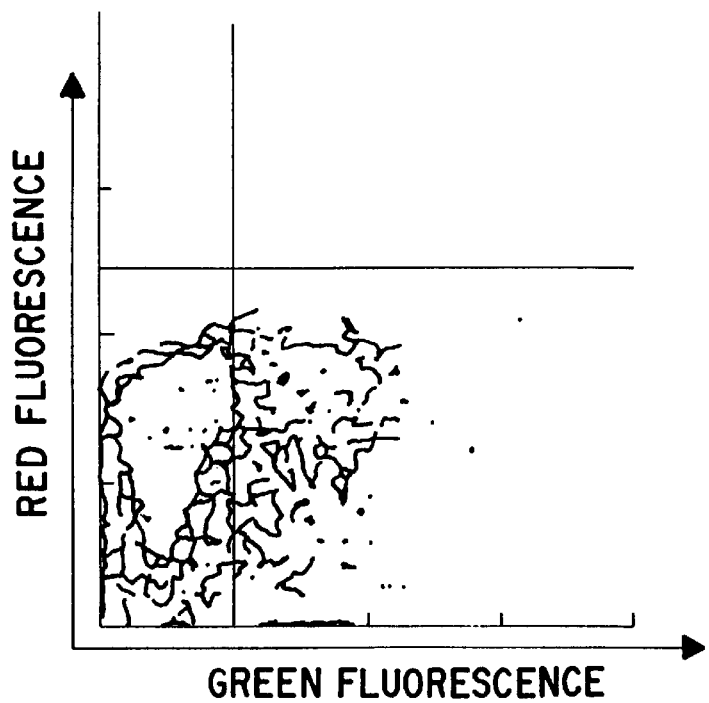
Figure 4F:
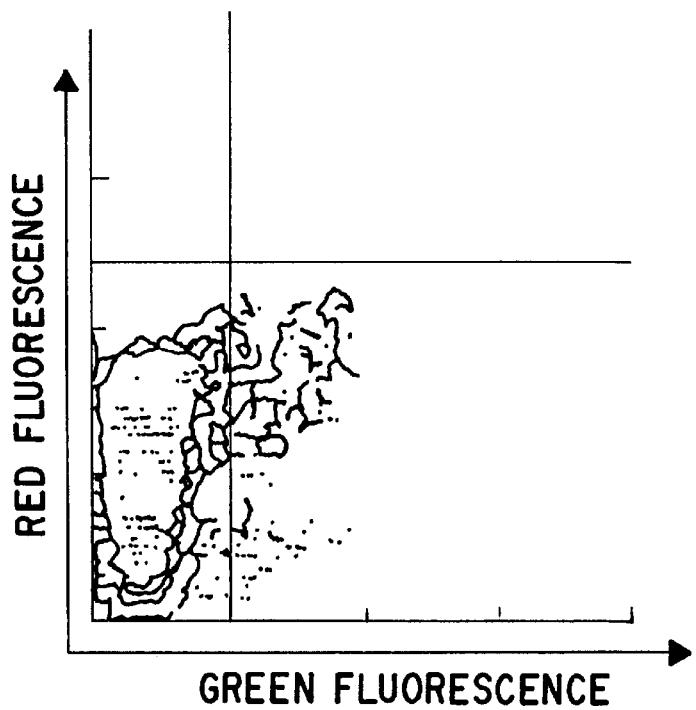
Figure 4G:
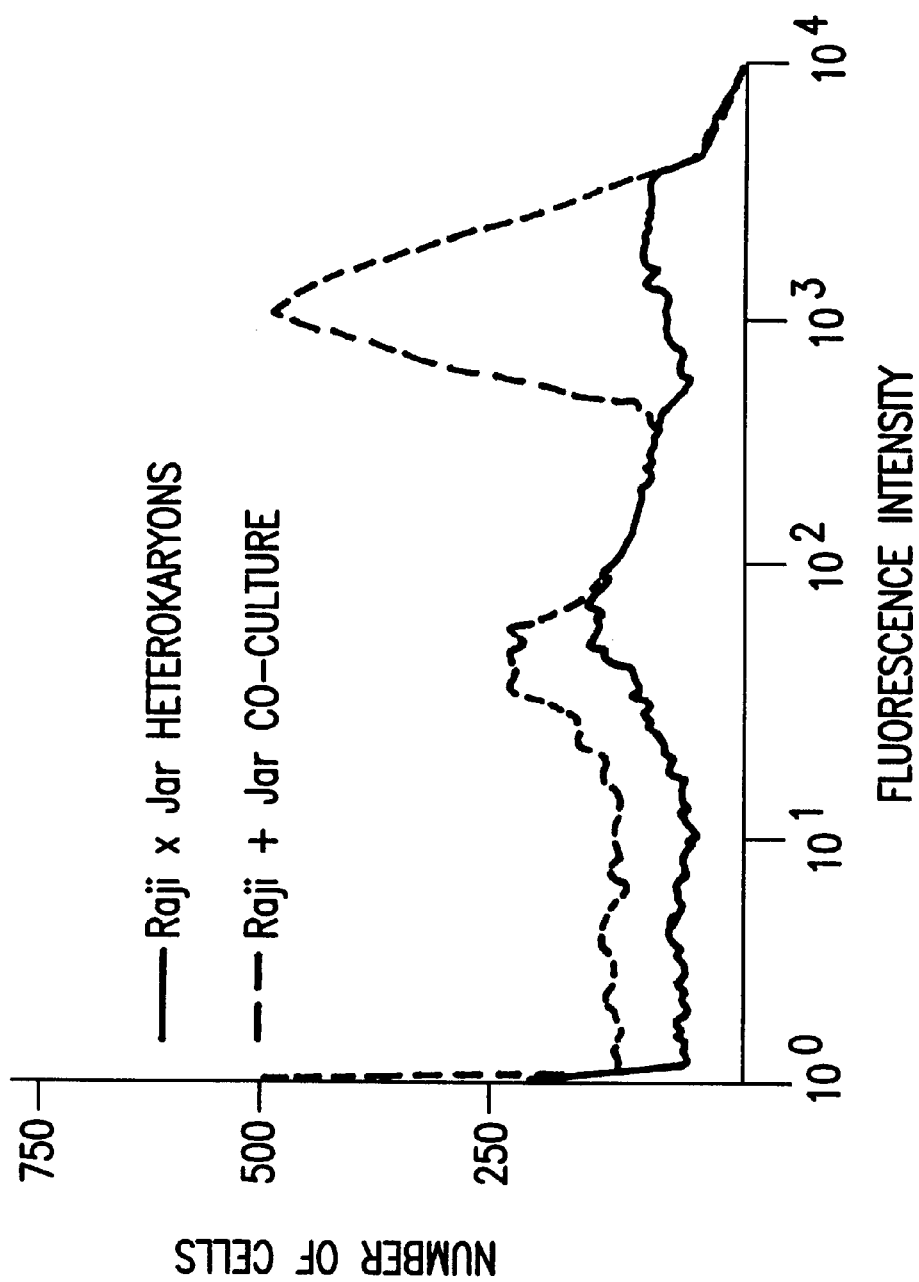

The dominant suppression exhibited in the transient heterokaryons is consistent with a transcriptional block specific for MHC class II because there was no noticeable increase in cell debris found in the Jar×Raji fusions compared to the HeLa×Raji fusions, and the cytoplasm of Jar cells is, therefore, unlikely to be generally cytotoxic. There was a fortuitous transfer of some dye from green-labeled Jar and HeLa cells to the antigen-expressing Raji cells in the absence of fusogen that made some of the Raji cells visible in the upper right quadrant under co-culture conditions (FIGS. 3C and 4C). This label transfer occurred during the 2 day culture period, and provided an internal control that allowed us to correlate differences in HLA-DR antigen levels on Raji cells with the presence of a specific fusion partner used and with presence or absence of the fusogen. Thus, any cellular macromolecules that were produced by Jar cells and taken up by Raji cells under conditions of co-culture did not affect MHC class II antigen expression. HeLa cells were chosen as "permissive" fusion partners for negative controls because no specific suppression is known to occur in these cells. The class II transactivator, CIITA, which is constitutively expressed in B lymphocyte lines (Steimle et al., 1993, Cell 75:135–146) is known to directly stimulate MHC class II transcription in IFN-γ-inducible cell lines (Steimle et al., 1994, Science 265:106–109; Chang et al., 1994, J. Exp. Med. 180:1367–74). The regulation of expression of CIITA in trophoblasts has not been characterized, and the suppression observed in these experiments may involve one or more steps in a putative constitutive Jak-STAT pathway (Darnell, J. E. et al., 1994, Science 264:1415–1420) of intracellular signalling by B lymphocytes that normally results in constitutive MHC class II expression, but is blocked by dominant trans-acting trophoblast factor(s). Alternatively, trophoblasts may express dominant suppressor factor(s) that block the known positive trans-acting factors that bind the conserved promoter motifs and are required for transcriptional activation of MHC class II genes (Glimcher, L. H. and Kara, C. J., 1992, Annu. Rev. Immunol. 10:13–49).

7. REPRESSION OF MAJOR HISTOCOMPATIBILITY COMPLEX CLASS I AND II GENES IN HUMAN TROPHOBLASTS BY TSU RNA

A dominant repressor of major histocompatibility complex antigen expression, termed trophoblast STAT utron ("TSU"), was cloned by negative immunoselection using a trophoblast cDNA expression library in IFN-γ-responsive HLA-DR⁺-HeLa cells. Recombinant TSU silenced MHC class I and II gene expression and blocked STAT1 function. Sequence analysis revealed that TSU was a small, poly-A⁺-RNA that contained 11 gene promoter motifs related to IFN signalling. Microinjection of TSU RNA, or treatment of cells with single-stranded oligonucleotide models of these motifs, also blocked STAT1 function. Physiological relevance was suggested by expression of TSU in placenta.

7.1. MATERIALS AND METHODS

7.1.1. EXPRESSION CLONING OF TSU CDNA BY NEGATIVE IMMUNOSELECTION

PolyA⁺-RNA was prepared with the PolyATTract System (Promega) from the trophoblast-derived choriocarcinoma cell line Jar (ATCC). Jar cell cDNAs were prepared with oligo-dT primers, size-selected, and cloned using standard methods (Sambrook et al., 1989, Molecular Cloning: A Laboratory Manual (Cold Spring Harbor Laboratory Press, Cold Spring Harbor, N.Y.) with directional adapters into the mammalian expression vector pSH4-hph$^m$ which provides an SV40 promoter, splice site upstream of cloning site, and poly-A addition signal as well as hygromycin resistance (Vasavada et al., 1990, Nucl. Acids Res. 18:3668–3668). Growth in DH10B Electromax E. coli (GIBCO) and 3-dimensional amplification procedure in 50 ml tubes were carried out to ensure reasonable representation by slow growing bacteria (Kriegler, 1990, Gene Transfer and Expression: A Laboratory Manual (Stockton Press, NY). Large plasmid preps with two CsCl bandings produced stock solutions for transfection (Sambrook et al., 1989, Molecular Cloning: A Laboratory Manual (Cold Spring Harbor Laboratory Press, Cold Spring Harbor, N.Y.). Size-selected sublibraries were prepared using 0.5 to 4 kb and 4 to 23 kb inserts. The Jar large-insert expression library consisted of $1.7 \times 10^5$ independent clones, and was used in the experiments described here. A clone of the cervical carcinoma cell line HeLa (ATCC) was isolated by limiting dilution culture that gave expression of HLA-DR antigen after stimulation by recombinant human IFN-γ (Boehringer-Mannheim), and this clone was expanded for further use. The cDNA expression library was transfected by the calcium phosphate method (Kriegler, 1990, Gene Transfer and Expression: A Laboratory Manual (Stockton Press, NY); Sambrook, 1989, Molecular Cloning: A Laboratory Manual (Cold Spring Harbor Laboratory Press, Cold Spring Harbor, N.Y.) into HeLa clone 6 cells. A total of approximately $2 \times 10^4$ stable transfectants resistant to 150 μg/ml hygromycin B (Boehringer-Mannheim) were screened from 4 transfections over several months. Three rounds of selection were performed by IFN-γ challenge (200 U/ml for 2 days) and sterile sorting by flow cytometry of live, lightly trypsinized cells stained in suspension at 4° C., gating on the lowest 5–10% of the range of HLA-DR antigen staining. The HLA-DR mAb L243 (IgG$_{2a}$ isotype, ATCC) was used versus non-immune mouspe IgG$_{2a}$ (Sigma, St. Louis, Mo.) as negative control. Untransformed, IFN-γ-treated HeLa cells served as positive control cells. mAb binding was detected with R-phycoerythrin-goat anti-mouse IgG secondary Ab (Molecular Probes) using a FACS IV (Becton-Dickinson). The isolation of antigen-negative cells was completed by cloning by limiting dilution and screening subcultures grown in chamber slides (Nunc) by immunocytochemistry using L243 30 mAb as described (Peyman and Hammond, 1992, J. Immunol. 149:2675–80). Twenty clones resulted, and genomic DNA was prepared from 19 of these. Rescue of integrated plasmid sequences was accomplished by PCR (Innis et al., 1990, PCR Protocols: A Guide to Methods and Applications, Academic Press, San Diego, Calif.). Primers were prepared that amplified sequences between the promoter and the poly-A signal of the expression vector: pSH4-1: 5'-GATGTTGCCTTTACTTCTAGGCCT-3' (SEQ ID NO:23), and pSH4-2: 5'-AACTCATCAATGTATCTTATCATG-3' (SEQ ID NO:24). Amplification was performed over 30 cycles of 1 min at 94° C., 2 min at 55° C., and 3 min at 72° C. in a thermal cycler (Perkin Elmer) using 1 U of Taq DNA polymerase (GIBCO) (Innis et al., 1990, PCR Protocols: A Guide to Methods and Applications, Academic Press, San Diego, Calif.). PCR products were identified using DNA from 5 of the 19 samples on agarose gels stained with ethidium bromide. Bands of approximately 0.6 kb were observed in two of these PCR products, and one, TSU cDNA, was cloned into the pCR3 vector and grown in TOP10F' E. coli following the instructions of the manufacturer (Invitrogen). The CMV promoter in pCR3 drives mammalian expression, and the vector provides neomycin resistance. Plasmids were purified on Qiagen tips (Qiagen Corp.). Restriction endonuclease mapping (Sambrook et al., 1989, Molecular Cloning: A Laboratory Manual (Cold Spring Harbor Laboratory Press, Cold Spring Harbor, N.Y.) of 9 TSU cDNA clones was performed to establish the orientation of the cDNA. To determine if the suppression of HLA-DR antigen expression in the primary transfectants was caused by a trans-acting factor encoded by the cDNA, both forward and reversed constructs were introduced into HeLa clone 6 cells by lipofection (Felgner et al., 1987, *Proc. Natl. Acad. Sci. USA* 84:7413–7417). Stable secondary transfectants were selected over 9 days with 600 μg/ml G418-containing medium, maintained for 7 days at 300 μg/ml G418 (GIBCO), and then cultured for 2 days in chamber slides without or with 200 U/ml IFN-γ. Cells were acetone-fixed and stained by the avidin-biotin-peroxidase method as described (Peyman and Hammond, 1992, *J. Immunol.* 149:2675–80). The primary mAb utilized were L243 for MHC class II, W6/32 for MHC class I, 7-2M for $Na^+,K^+$-ATPase (Smith et al., 1987, *Amer. J. Physiol.* 253(2 Pt 1):G99–109) as positive control, and normal mouse $IgG_{2a}$ or IgG1 (Sigma) as negative controls.

7.1.2. DNA SEQUENCING AND SEQUENCE ANALYSIS

Double-stranded plasmid DNA was sequenced by the fluorescent cycle sequencing method with an Applied Biosystems 373A DNA Sequencer. Primers used for sequencing were pSH4-1 (SEQ ID NO:23), pSH4-2 (SEQ ID NO:24), T7 promoter primer (5'-TAATACGACTCACTATAGGG-3') (SEQ ID NO:25), and internal primers TSU-1 (5'-GTGTGATCTGAAAACCCTGCTTGG-3') (SEQ ID NO:26), TSU-2 (5'-AGACTACTTCCCCATACATGCG-3') (SEQ ID NO:27), and TSU-3 (5'-CCATACAGAGCAACATACCAGTAC-3') (SEQ ID NO:28). Data were analyzed with the Genetics Computer Group programs (Devereux et al., 1984, *Nuc. Acids Res.* 12:387–395), searching of the combined sequence databases at NCBI was performed with the BLAST program (Altschul et al., 1990, *J. Mol. Biol.* 215:403–410), and searching the eukaryotic transcription factor database (Ghosh, 1990, *Nucl. Acids Res.* 18:1749–56) was carried out with the FindPatterns program. The dot plot was generated by the Compare and Dotplot programs with a window of 21 bases and a stringency of 14. The calculations of sequence identity between TSU and the goat EST were based on alignment by the Gap program. These nucleotides were ignored in the calculations: single-base gaps in the goat EST (considered sequencing errors), 4 other gaps in the goat EST required to align the sequences, 6 non-sequence bases (N) in the goat cDNA, the 2 single-base gaps in the TSU cDNA opposite possible insertions or sequencing errors in the goat EST, and the poly-A tails. Total sequence compared was 419 bases.

7.1.3. IMMUNOCYTOCHEMISTRY TO DETECT STAT1 IN HeLa AND JAR CELLS

An ISGF3 mAb (IgG1 isotype, Transduction Laboratories) that recognizes an N-terminal epitope in STAT1 was used at 10 μg/ml to stain cells grown on chamber slides after acetone fixation by the avidin-biotin-peroxidase method as described (Peyman and Hammond, 1992, *J. Immunol.* 149:2675–80). Nonimmune mouse IgG1 (Sigma) was the negative control antibody, and HeLa cells incubated at 37° C. without or with 30 min treatment with recombinant human IFN-γ were the positive control cells for cytoplasmic and nuclear STAT1 antigen, respectively.

7.1.4. MICROINJECTION Of RNA

The TSU-pCR3 expression construct was linearized with Not I (New England Biolabs) in the polylinker downstream of the insert, and recombinant RNA was produced by in vitro transcription with T7 RNA polymerase (New England Biolabs) as described (Peyman and Hammond, 1992, *J. Immunol.* 149:2675–80). Plasmid DNA was then removed by 15 min incubation with 1 U of RNAase-free DNAase I (Promega). TSU RNA was purified by two phenol-chloroform extractions, one chloroform extraction, and ethanol precipitation (Sambrook et al., 1989, *Molecular Cloning: A Laboratory Manual* (Cold Spring Harbor Laboratory Press, Cold Spring Harbor, N.Y.). Yeast tRNA (Boehringer-Mannheim) stock solution (10 μg/ml) was sheared by sonication, phenol-chloroform extracted three times, and residual phenol was removed by chloroform extraction. RNA concentrations were determined by $A_{260}$ measurement. DMEM culture medium was replaced with α-MEM containing 20 mM HEPES-NaOH, pH 7.4, 20% fetal bovine serum and penicillin-streptomycin-antimycin A for microinjection and IFN-γ treatment. Solutions of 1 μg/ml or 0 ng/ml TSU RNA, or 1 μg/ml yeast tRNA, in 120 mM KCl, 10 mM Tris-HCl, pH 7.5 buffer were loaded into sterile femtotips (Eppendorf) and microinjected into the juxtanuclear cytoplasm of HeLa cells grown on coverslips at low density and individually identified by position in relation to a manually etched grid. Microinjection was performed on a Zeiss IM inverted microscope with Nomarski optics, using a Zeiss micromanipulator and an Eppendorf 5242 microinjector as described (Martin and Helenius, 1991, *J. Virol.* 65:232–244). Successful microinjections were indicated by cell swelling by approximately 10% upon delivery of the bolus of about 15–20 picoliters of RNA or buffer and by the absence of blebs forming on the cell membrane. Microinjected cells were recorded on the schematic cell identification map for each cover slip and after subsequent treatments each cell was reidentified. IFN-γ was added to the medium after microinjection, and the cells were incubated for 30 min at 37° C., after which acetone fixation and immunocytochemical determination of STAT1 localization were carried out as described above.

7.1.5. TREATMENT OF HeLa AND JAR CELLS WITH OLIGONUCLEOTIDES

A series of oligonucleotides was designed based on the sequences of the TSU GAS motifs 10 and 7 and ISRE motifs 12 and 6 (FIGS. 5B and Table 1). The GAS motif 10 was found to be flanked by 7 complementary bases and may form a stem-loop structure in TSU RNA. Similarly, GAS complement motif 7 flanking sequences could form a 4-base stem. Three arbitrary base pairs were added to this to make a 7-base stem in the synthetic GAS complement motif 7 oligonucleotide. ISRE motif 12 could form at least two stem-loop structures with adjacent bases in which the conserved AGTTT sequence would be in the stem, and so the naturally occurring flanking sequences were employed in the oligonucleotide. ISRE complement motif 6 was flanked by sequences that could form 2 six-base stems. In the synthetic ISRE complement motif 6 oligonucleotide these were replaced with a simple 6-base stem. A non-complementary transversion mutant was synthesized replacing the TTAC bases in GAS motif 10 with GGAT and replacing two other neighboring TTNC sequences with TTTG and TTCA. A mutant ISRE complement motif oligonucleotide was prepared by replacing the conserved TCAAA with GACGC and the conserved AA with AC. The predicted folding of these synthetic oligonucleotides is shown in FIG. 10. The TSU antisense and sense phosphorothioate oligonucleotides were based on a sequence between motifs 6 and 7. The following phosphorothioate oligodeoxynucleotides were synthesized, with the promoter motifs and point mutations shown in boldface type:

```
GAS,                   5'-ACTTTTCTTCCCCTTTACAGCACAAATAAAGT-3'        (SEQ ID NO:29)

GAS mutant,            5'-ACTTTTGTTCACCTGGATAGCACAAATAAAGT-3'        (SEQ ID NO:30)

GAS complement,        5'-CGATGTTGCTCTGTATGGTAAGAACATCG-3'           (SEQ ID NO:31)

ISRE,                  5'-ACAAATAAAGTTTGAGTTCTAAACTCAT-3'            (SEQ ID NO:32)

ISRE complement,       5'-CGATCGGTGAAATTGAAACTCGATCG-3'              (SEQ ID NO:33)

ISRE complement mutant, 5'-CGATCGGTGACATTGCGCAGCGATCG-3'             (SEQ ID NO:34)
```

Oligonucleotides were synthesized with cyanoethyl phosphoramidite reagents on an Applied Biosystems Model 380B DNA synthesizer, with the sulfurizing reagent used according to the manufacturer's instructions (Glen Research, Sterling, Va.). Cells grown in chamber slides were treated for 1h at 37° C. with 10 μM of each respective oligonucleotide in DMEM-10% fetal bovine serum with antibiotics. IFN-γ was added to a final concentration of 200 U/ml, and the cells were incubated 0.5 h more for STAT1 activation and then acetone-fixed for immunocytochemical localization of STAT1 antigen. Preliminary experiments indicated that 1 μM concentrations of GAS oligonucleotide 10 or ISRE complement oligonucleotide 6, but not 100 nM or 10 nM could block STAT1 function after 100 h, but not 10 h treatments, and the optimum effect at 0.5 to 1 h was observed with 10 μM oligonucleotide, the highest dose tested.

7.1.6. NORTHERN BLOT ANALYSIS

Poly-A$^+$ RNA (2 μg) was isolated from 16 normal human tissues and displayed on formaldehyde-agarose gels, and Northern blots were prepared (Clontech). $^{32}$P-labeled TSU antisense RNA probe was synthesized by in vitro transcription using Not I-linearized TSU-pCR3 reversed construct and T7 RNA polymerase as described (Peyman and Hammond, 1992, *J. Immunol.* 149:2675–80). Hybridization with 10$^6$ cpm/ml probe at 55° C. for 40 h in hybridization buffer (Sambrook et al., 1989, *Molecular Cloning: A Laboratory Manual* (Cold Spring Harbor Laboratory Press, Cold Spring Harbor, N.Y.) containing 50% formamide was followed by a final wash with 0.1× SSC-0.5% SDS at 55° C. for 1 h. Sequential autoradiographic exposures were produced with an intensifying screen. Results represent two independent preparations and analyses.

7.2. RESULTS

Stable transfectants expressing trophoblast cDNAs driven by the SV40 promoter in the pSH4-hph$^m$ vector in HeLa clone 6 cells were selected by including the lowest 5–10% of the flow cytometry profile for HLA-DR antigen after 2 day IFN-γ treatment, as described in Materials and Methods. The expression cloning strategy is shown in FIG. 5A. Three rounds of sterile cell sorting yielded mixtures of HLA-DR-positive and negative clones (results not shown), and so cell clones were isolated by limiting dilution culture. A total of 20 clones derived from 4 transfections with the Jar cDNA library were expanded for further analysis because they expressed low HLA-DR antigen levels on the cell membrane or in intracellular compartments when analyzed by avidin-biotin-peroxidase immunocytochemistry (results not shown). PCR was carried out to rescue cDNAs using flanking vector primers and genomic DNA prepared from 19 of the transfectant clones. Two of these cell clones yielded an approximately 0.6 kb amplimer. The PCR products were cloned into the pCR3 expression vector, and plasmid stocks were prepared for mapping, sequencing, and re-testing of regulatory function of the cDNAs in human cells by transfection.

Plasmids from 3 bacterial clones of the 0.6 kb PCR product were sequenced, as described in Materials and Methods. Eight overlapping sequences, covering the cDNA insert at least 4 times, were obtained. The DNA sequence of TSU is shown in FIG. 5B (SEQ ID NO:1). Sequence analysis indicated that TSU was encoded by a 481 bp cDNA with no significant similarities to known DNA or polypeptide sequences in the database, except that TSU corresponded to 11 previously cloned expressed sequence tags (EST) from several human tissues and cell lines (D17151, D20167, D29026, R22093, R31782, R38041, R71357, T15746, T30784, T32811, and T61459) and similar to an EST from goat (X73800). The EST were retrieved from the Genbank at NCBI with BLAST (Altschul et al., 1990, *J. Mol. Biol.* 215:403–410); nothing had been reported about their functional characteristics. Both the human TSU cDNA and goat EST included a poly-A addition signal upstream of a 3-base and a 30 base poly-A tail, respectively. The TSU sequence did not encompass a long open reading frame, and the human and goat cDNAs contained no conserved open reading frames. Conserved in these sequences were, however, a total of 11 motifs related to IFN signalling: 5 GAS, 4 ISRE, and 2 IL-4-response elements (IL-4RE, TTNCNNNNAA (SEQ ID NO:37)). The GAS and ISRE were observed as both coding strand (GAS, TTNCNNNAA; ISRE, AGTTTCNNTTYYYY, Y=C/T) (SEQ ID NO:38) and complementary strand (GAS complement, TTNNNG-NAA; ISRE complement, RRRRAANNGAAACT, R=A/G) (SEQ ID NO:39) versions of the consensus sequences. The TSU cDNA was 73% identical to the goat EST, 58% in the 3'-220 bp and 80% in the 5'-261 bp. Regions excluding the 11 promoter motifs were 54% identical in the 3'-220 bp and 81% identical in the 5'-261 bp. The 11 motifs were 70% identical in the 3'-220 bp and 94% identical in the 5'-261 bp, excluding the variable bases in the consensus sequence. The human TSU and the goat EST had conserved IFN-γ-related promoter motifs in a poly-A$^+$ RNA. The homology between TSU cDNA and the goat EST was shown graphically by dot plot analysis (FIG. 6). The diagonal line indicated sequence identity. The gene promoter motifs were located within the conserved regions, except for the ISRE motif 3, and each conserved region contained at least one promoter motif, except for the region around bp 200. The GAS, ISRE, and IL-4RE sequences of TSU are shown in Table 1.

TABLE 1

EXPRESSED GENE PROMOTER MOTIFS IN TSU AND GOAT EST

| Sequence Motif | TSU Sequence | SEQ ID NO. | Goat EST Sequence | SEQ ID NO. |
|---|---|---|---|---|
| 1. GAS complement | GTAAAGTAA | 2 | ATAAAGTAA | 58 |
| 2. IL-4RE | TTCCCTTTAA | 3 | TTCCCATTGA | 59 |
| 3. ISRE | AGTTTCACTTGAAA | 4 | ATTTCGTTTTGAGA | 60 |
| 4. ISRF | AGTTCAGTTCTTA | 5 | AGTTGCATTCTTA | 61 |
| 5. GAS complement | TATGGGGAA | 6 | TATGGGGAA | 6 |
| 6. ISRE complement | GTGAAATTGAAACT | 7 | GTGAAATTGAAACT | 7 |
| 7. GAS complement | GTATGGTAA | 8 | GTATGGTAA | 8 |
| 8. GAS | TTACGTCAT | 9 | TTGCATCAT | 62 |
| 9. IL-4RE | TTACTAATCA | 10 | CTACTAACA | 63 |
| 10. GAS | TTACAGCAC | 11 | TTACAGCAC | 11 |
| 11. Poly-A signal | AATAAA | 12 | AATAAA | 12 |
| 12. ISRE | AGTTTGAGTTCTAA | 13 | GGTTTGCGTTCTAA | 64 |

A sequence that has also been found in TSU CDNA is a MHC Class I variant TATA box: TCTAAA (nucleotides 467–472 of FIG. 5B).

Figure 13B:
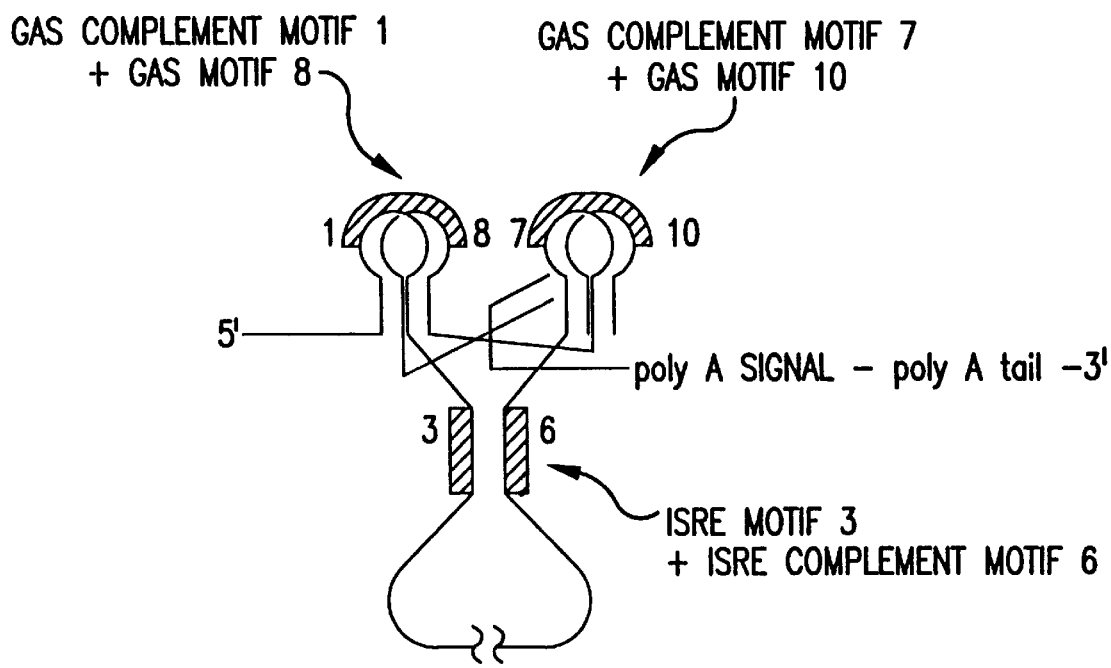

A predicted folding pattern of six regions containing three pairs of complementary motifs of TSU RNA is shown in FIGS. 13A–B.

Introduction of pCR3 subclone DNA into HeLa clone 6 cells was accomplished by lipofection, and secondary stable transfectant batches were tested by antibody staining for repeated suppression of the MHC class II antigen by the putative trans-acting cDNA after IFN-γ treatment (See Materials and Methods). The HeLa-TSU-pCR3 transfectants shown in FIG. 7A did not respond to IFN-γ. The HLA-DR antigen was not detected (open arrows), and, surprisingly, both basal and stimulated levels of HLA-A, B, C antigens were reduced to background (open arrows). Positive control $Na^+$,$K^+$-ATPase antigen expression was unaffected by the TSU gene product or by IFN-γ under all conditions in FIG. 7, and the negative control mouse $IgG_2$, produced faint background staining with punctate nucleolar signals under all conditions. The HeLa-TSU-pCR3-reversed orientation transfectant cells (producing TSU antisense RNA) (FIG. 7B) responded to IFN-γ by inducing expression of HLA-DR antigen and increasing the constitutive expression of HLA-A, B, C to a high level. FIG. 7C shows the immunocytochemical staining of the positive control cells, untransfected HeLa clone 6. IFN-γ treatment induced the biosynthesis of HLA-DR (solid arrows) and increased the level of HLA-A, B, C antigens from a low level (solid arrows). In these samples the presence of high levels of antigens in the endoplasmic reticulum compartment of the biosynthetic pathway was shown by nuclear membrane staining, and cell membrane stain covered entire cell profiles. Southern blot analysis of Eco RI-cut genomic DNA from TSU and reversed TSU stably transfected cells with an TSU probe indicated that copy numbers of integrated plasmids were similar, and Northern blot analysis of recombinant TSU sense and antisense RNA from these stable transfectant batches showed similar production of recombinant mRNA (data not shown). The cytomegalovirus promoter drives high-level, constitutive expression of cDNA inserts in pCR3.

The coordinate suppression of both MHC class I and II antigens by this cDNA suggested the possible inhibition of STAT1. The phosphorylation, dimerization, and transport to the nucleus of STAT1 can be followed by immunocytochemical localization of the STAT1 antigen in IFN-γ-treated cells (Shuai et al., 1993, *Science* 261:1744–46; Loh et al., 1994, *Mol. Cell. Biol.* 14:2170–2179). To determine whether the function of STAT1 was impaired in TSU-transfectants, batches of cells expressing either sense or antisense TSU RNA were treated with IFN-γ for 2 days and STAT1 was localized with a specific mAb (See Materials and Methods). The TSU-pCR3 transfected HeLa cells gave moderate cytoplasmic staining for STAT1 over background both in the absence and presence of IFN-γ stimulation (FIG. 8A, open arrows), whereas the reversed-TSU-pCR3 transfectants gave a cytoplasmic STAT1 pattern without IFN-γ treatment but a clear nuclear pattern following IFN-γ stimulation (FIG. 8B, solid arrows). The TSU RNA appeared to interfere with one or more of the steps of STAT1 activation.

To define a mechanistic role for the TSU scRNA independent of the transfected DNA, purified, recombinant TSU RNA was microinjected directly into HeLa cells which were challenged with a brief IFN-γ treatment and then stained for STAT1 localization. Preliminary experiments demonstrated that solutions containing less than 1 μg/μl demonstrated little STAT1 inhibition, but injection of 1 μg/μl TSU RNA caused inhibition of IFN-γ stimulated STAT1 nuclear localization (FIG. 9A, open arrows). Negative control injections of KCl-Tris buffer alone (FIG. 9B, solid arrows) or of 1 μg/μl tRNA (not shown) allowed the cells to respond to IFN-γ with functional STAT1.

Treatment of IFN-γ-responsive cells with GAS or ISRE motif-containing phosphorothioate deoxyribonucleotide models of TSU was performed to test the hypothesis that single-stranded promoter structures could function to block STAT1 activation. The motifs and oligonucleotides derived from them are numbered as in Table 1. The results showed that STAT1 was inactivated in greater than 50% of cells treated with the GAS oligonucleotide 10, GAS complement oligonucleotide 7, and ISRE complement oligonucleotide 6 (FIG. 10, open arrows), and that STAT1 maintained activity in cells treated with the GAS point mutant oligonucleotide 10M or the ISRE complement point mutant oligonucleotide 6M (FIG. 10, solid arrows). The HeLa cells not treated with oligonucleotides showed the range of STAT1 function that is observed by immunocytochemistry, from moderate cytoplasmic staining without IFN-γ (open arrow) to strongly localized nuclear signals with IFN-γ (solid arrow). ISRE oligonucleotide 12 did not inhibit STAT1 function (FIG. 10, open arrow indicating cytoplasmic antigen plus solid arrow marking strong nuclear accumulation of antigen). Percentage of moderate to strong nuclear localization of STAT1 antigen was estimated by visual counting of smaller colonies (<100 cells) in the center one-half of each microscope slide chamber. Staining and intracellular antigen localization of confluent sheets of cells and cells at the edges of the chamber were often aberrant.

Northern blot analysis of 16 human tissues showed that expression of the 0.5 kb small cytoplasmic TSU RNA was restricted to placenta (FIG. 11). Minor TSU-related mRNAs of 2.4, 4.4, and 6.0 kb were also observed in placenta. The related 2.4 kb mRNA was also expressed in heart and skeletal muscle, and was the predominant species expressed in pancreas. The 4.4 kb related mRNA was expressed in all tissues tested. Southern blot analysis showed that TSU is encoded by a single-copy gene in the human genome.

7.3. DISCUSSION

7.3.1. EVOLUTIONARY CONSERVATION OF TSU EXPRESSED PROMOTER MOTIFS

Sequence analysis by database searching produced no significant matches, except for 12 ESTs. Visual inspection disclosed the presence of a poly-A addition signal and a number of short motifs similar to GAS, ISRE, and IL-4RE promoter elements. Subsequent scanning of the promoter database for identity to TSU sequences did not yield any additional important information. The TSU GAS motifs 8 and 10, the IL-4RE motif 9, and the ISRE motif 6 were detected by this computer analysis, but the GAS motifs 1, 5, and 7, the IL-4RE motif 2, and the ISRE motifs 3 and 4 were missed. The last bases in GAS motifs 1, 5, 7, 8, and 10 and the IL-4RE motif 9, AC, TA, AC, AT, AC, and CA, respectively, are different from the last bases of the consensus TTNCNNNAA or TTNCNNNNAA (SEQ ID NO:40) (Seidel et al., 1995, Proc. Natl. Acad. Sci. 92:3041–45). Some of these variants were absent from the promoter database. The conservation of the promoter motifs, but not any polypeptide coding sequence, in the human TSU and the TSU-related goat EST provided a strong evolutionary argument for the idea that TSU RNA inhibits STAT1 function and thus MHC class I and MHC class II gene expression without the participation of an TSU-encoded polypeptide.

7.3.2. MHC CLASS I AND MHC CLASS II ANTIGEN SUPPRESSION AND STAT1 INHIBITION BY TRANSFECTED RECOMBINANT TSU

Constitutive MHC class I and IFN-γ-inducible MHC class I and II antigen expression in stably transfected HeLa cells were reduced to background levels by the sense TSU RNA gene product, but not by the antisense RNA gene product. In addition, STAT1 function was blocked by the transfected TSU sense RNA gene product, not by the antisense RNA gene product. These results are consistent with the idea that the effect of the TSU cDNA in transfected cell lines was not caused by the presence of a double-stranded TSU construct, but, rather, was caused by the TSU RNA itself. In the alternative case of a promoter element CDNA decoy consisting of multiple integrated copies, the activated STAT1 would be sequestered in the nucleus, not the cytoplasm. This was not observed. Testing the TSU cDNA in secondary transfectants demonstrated repeated trans-acting function and eliminated the possibility of insertional inactivation by an irrelevant cDNA of an endogenous gene critical for MHC gene expression, or of other mutations in the host cell genome.

7.3.3. STAT1 INHIBITION BY MICROINJECTED RECOMBINANT TSU RNA

STAT1 function was blocked in HeLa cells microinjected with purified recombinant TSU RNA, but not with buffer or control tRNA. These observations demonstrated the direct inhibition of the nuclear transport of activated STAT1 by TSU RNA.

7.3.4. STAT1 INHIBITION BY SINGLE-STRANDED TSU PROMOTER MOTIF OLIGONUCLEOTIDES

STAT1 function in HeLa cells was blocked by treatment with oligonucleotides corresponding to single-stranded stem-loop GAS, GAS complement, and ISRE complement motifs, whereas mutants of GAS and ISRE complement motifs allowed normal STAT1 function. The inhibition of STAT1 correlated with the presence of specific sequences. These results supported the ideas that STAT1 suppression did not depend on double-stranded gene promoter targets nor depend on the formation of an TSU-encoded polypeptide, but that the single-stranded promoter sequences found in at least three motifs in TSU could independently block STAT1 function. Oligodeoxynucleotides used for uptake by cells were phosphorothioate-modified because of their resistance to nuclease degradation relative to phosphodiester oligodeoxynucleotides (Beltinger et al., 1995, J. Exp. Med. 176:1115–23). The 3 oligonucleotide motifs that blocked STAT1 function consisted of DNA homologs, and there may be significant differences between single-stranded DNA and RNA binding to STAT1 dimer. Binding analyses using cell extracts or purified recombinant components should help confirm the proposed molecular mechanism of TSU function. The reduction in percentage of oligonucleotide-treated HeLa cell colonies showing moderate to strong IFN-γ-stimulated nuclear localization of STAT1 antigen after incubation with mutant oligonucleotides indicates sequence-independent effects of the GAS and ISRE complement mutant sequences, whereas the greater reduction in percentage of nuclear STAT1 with three of the four promoter motif oligonucleotides indicates additional sequence-specific effects of GAS, GAS complement, and ISRE complement sequences. Variation among cell colonies was clearly apparent under each of these conditions of treatment, independent of location on the microscope slide. Perhaps cell cycle effects are important for the modulation of levels or activities of endogenous factors, such as STAT1, that are titrated by these promoter motif oligonucleotides.

7.3.5. TSU RNA EXPRESSION IN PLACENTA

Normal human term placenta expresses mainly a 0.5 kb TSU RNA, seen by Northern blot analysis of poly-A$^+$ RNA, whereas other human tissues express predominantly a related 4.4 kb mRNA of unknown function. The production of the TSU RNA in placenta, therefore, appears to involve alternative splicing. Cloning and sequencing of the genomic TSU gene and the related mRNAs may resolve this question.

The name trophoblast STAT utron, or TSU, denotes the trophoblast gene product that inhibits the function of STAT protein and takes the form of an untranslated RNA, or utron.

7.3.6 PREDICTED FOLDING OF TROPHOBLAST STAT UTRON

The sequences of three pairs of the promoter motifs in the trophoblast STAT utron and of three pairs of the evolutionarily conserved goat homolog can be aligned as follows:

```
                    Human                    Goat
GAS complement #1  5'-GTAAAGTAA-3'          5'-ATAAAGTAA-3'
                    :| |·||||                || | |·||
GAS #8             3'-TACTGCATT-5'          3'-TACTACGTT-5'

ISRE #3            5'-AGTTTCACTTGAAA-3'     5'-ATTTCGTTTTGAGA-3'
                    ||||||| ||··|·            ||||: ||| |
ISRE complement #6 3'-TCAAAGTTAAAGTG-5'     3'-TCAAAGTTAAAGTG-5'

GAS complement #7  5'-GTATGGTAA-3'          5'-GTATGGTAA-3'
                    || :·||||                || :·||||
GAS #10            3'-CACGACATT-5'          3'-CACGACATT-5'
```

Lines between nucleotides indicate traditional Watson-Crick base-pairing, while a single dot or pair of dots indicates non-traditional base pairing.

The characteristics of RNA folding and the requirement for univalent and divalent ions in some folded RNA structures have been reviewed (Draper, 1996, *Trends Biochem. Sci.* 21:145–149). The single-stranded loops and bulges of the folded RNA structures are shown to form RNA loop-loop or loop-bulge complexes in FIGS. 12A–D, 13A–B, 14A–B, and 15A–B. There is precedent for the biological activity of naturally occurring RNA molecules containing these structures. A bimolecular RNA loop-loop complex has been observed to function as a protein-binding structure in the regulation of replication of the bacterial ColE1 plasmid (Marino et al., 1995, *Science* 268:1448–1454) and an intramolecular loop-loop complex has been observed to function in inhibition of HIV-1 viral RNA translation (Chang and Tinoco, 1994, *Proc. Natl. Acad. Sci. USA* 91:8705–8709).

Intramolecular hydrogen bonding observed by X-ray crystallography, NMR analysis, or enzyme or chemical mapping of folded RNA structures includes mostly A-U and C-G base-pairs, some G-U base-pairs, and rarely A-G base-pairs (Pley et al., 1994, *Nature* 372:68–74; Doudna and Cech, 1995, *RNA* 1:36–45; Pan, 1995, *Biochemistry* 34:902–909; and Scott et al., 1995, *Cell* 81:991–1002). Therefore, the predicted base-pairing of the three pairs of promoter motifs in the trophoblast STAT utron constitute a reasonable structural basis for the idea that loop-loop or other tertiary configurations may play an important part in the STAT binding.

7.3.7. CONCLUSION

Five lines of evidence presented in this example demonstrate that TSU is a single-stranded poly-A$^+$ RNA gene promoter decoy that functions to inhibit STAT1 nuclear localization and repress MHC gene expression: 1) The human TSU cDNA and goat TSU-related EST had no common open reading frames, but showed conservation of IFN-signal transduction target motifs. 2) Sense and antisense TSU cDNA expression constructs demonstrated qualitatively different suppression of MHC antigen expression and of STAT1 function in transfected cells. 3) Microinjection of recombinant TSU RNA into HeLa cells blocked STAT1 function in several minutes. 4) Three of the four TSU promoter motif single-stranded oligonucleotides tested blocked STAT1 function over 1 h. 5) The placenta naturally produced a relatively abundant, small, poly-A$^+$, TSU RNA.

The interesting and unexpected discovery in trophoblasts of a small poly-A$^+$ RNA that blocks STAT1 function and represses MHC genes has answered some long-standing questions in reproductive immunology.

8. SYNTHETIC HUMAN IL-2 (INTERLEUKIN-2) GENE REPRESSOR UTRON

The IL-2 repressor utron was designed using information about several functional sequences within the human IL-2 gene promoter region and the transcription factors that bind to the promoter region (Skerka et al., 1995, *J. Biol Chem.* 270:22500–22506). IL-2 gene expression is induced in human T lymphocytes upon stimulation by intracellular signals derived from the T cell antigen receptor or other signals. This 11. AP-1
12. NF-AT-AC-AP-1
Stem-loop structures:
13. ZIP complement
14. NF-AT complement
15. AP-1 complement
16. NF-AT-AC-AP-1 complement
Hairpin structures
17. ZIP complement
18. NF-AT complement
19. AP-1 complement
20. NF-AT-AC-AP-1 complement
Bulge structures
21. ZIP complement
22. NF-AT complement
23. AP-1 complement
24. NF-AT-AC-AP-1 complement These structures have the following specifications, where the letters are those representing the particular aspects of the structure as shown in FIGS. 12A–D. For stem-loop structures 1–4 and 13–16:

a=5 base random sequence 5'-ATACG-3'
b=5 bp double-stranded random sequence stem 5'-GATCG-3'
d=a
j=none For hairpin structures 5–8 and 17–20:
e=a
f=4 bp random sequence 5'-ACAG-3'
g=f
h=6 base loop 5'-CTGAAT-3'
i=a
j=none For bulge structures 9–12:
j=2 bases 5'-AC-3'
l=a
m=b
n=b
p=h
r=a For bulge structures 21–24:
j=2 bases 5'-TA-3'
l=a
m=b
n=b
p=h
r=a For all structures 1–24:
polyadenylation signal=5'-AATAAA-3' followed by a spacer of 5'-ATTCTAGCACT-3' followed by (A)$_n$ (polyA tail; n=at least 2) to form the sequence 5'-AATAAAATTCTAGCACT(A)$_n$ (SEQ ID NO:41)

Based upon suitable preliminary experiments using the individual component sequences to determine relative functional capabilities, a composite utron can be designed containing one or more of each functional unit. Utilizing the IL-2 repressor utron components 1, 6, 12, 13, and 24 above, a composite IL-2 repressor utron was designed. The structure of this IL-2 repressor utron is depicted in FIG. 14A and the specifications of the individual components, using the letter symbols for the particular structural aspects specified in FIGS. 12A–D, in addition to those specified above, are described as follows:

For stem-loop structure 1:
c=14 base (loop) including 8 base ZIP sequence 5'-CATCCCCACCCTGG-3' (SEQ ID NO:42)

For stem-loop structure 13:
c=14 base (loop) including 8 base ZIP sequence complement 5'-CATGGGTGGGGTGG-3' (SEQ ID NO:43)

For hairpin 6:
Functional motif=NF-AT=5'-GGAAAA-3'

For bulge structure 12:
k=23 base bulge including NF-AT and AP-1 motifs=5'-AGGAGGAAAAACTGTTTCATACG-3' (SEQ ID NO:44)
q=20 base bulge non-complementary to k=5'-TTCACACTGCCTAGATACT-3' (SEQ ID NO:45)

For bulge structure 24:
k=23 base bulge including NF-AT complement and AP-1 complement=5'-CGTATGAAACAGTTTTTCCTCCT-3' (SEQ ID NO:46)
q=20 base bulge 5'-GAGTATCTAGGCAGTCTGAA-3' (SEQ ID NO:47)

Following the above specifications:
stem-loop component structure 1 consists of:
5'-ATACGGATCGCATCCCCACCCTGGCGATCATACG-3' (SEQ ID NO:75)
stem-loop component structure 13 consists of:
5'-ATACGGATCGCATGGGTGGGGTGGCGATCATACG-3' (SEQ ID NO:76)
hairpin component structure 6 consists of:
5'-ATACGACAGGGAAAAACAGCTGAATCTGTTTTTCCCTGTATACG-3' (SEQ ID NO:65)
bulge component structure 12 consists of:
5'-ATACGGATCGAGGAGGAAAAACTGTTTCATACGGATCGCTGAATCGATCTTCACACTGCCTAGATACTCGATCATACG-3' (SEQ ID NO:66)
bulge component structure 24 consists of:
5'-ATACGGATCGCGTATGAAACAGTTTTTCCTCCTGATCGCTGAATCGATCGAGTATCTAGGCAGTCTGAACGATCATACG-3' (SEQ ID NO:67)

Thus, in a specific embodiment, the invention provides a utron comprising or, alternatively, consisting essentially of stem loop component 1, bulge component 12, stem loop component 1, hairpin component 6, stem loop component 13, bulge component 24, and stem loop component 13, preferably in the 5' to 3' order listed, and as shown in FIG. 14A.

Figure 14B:
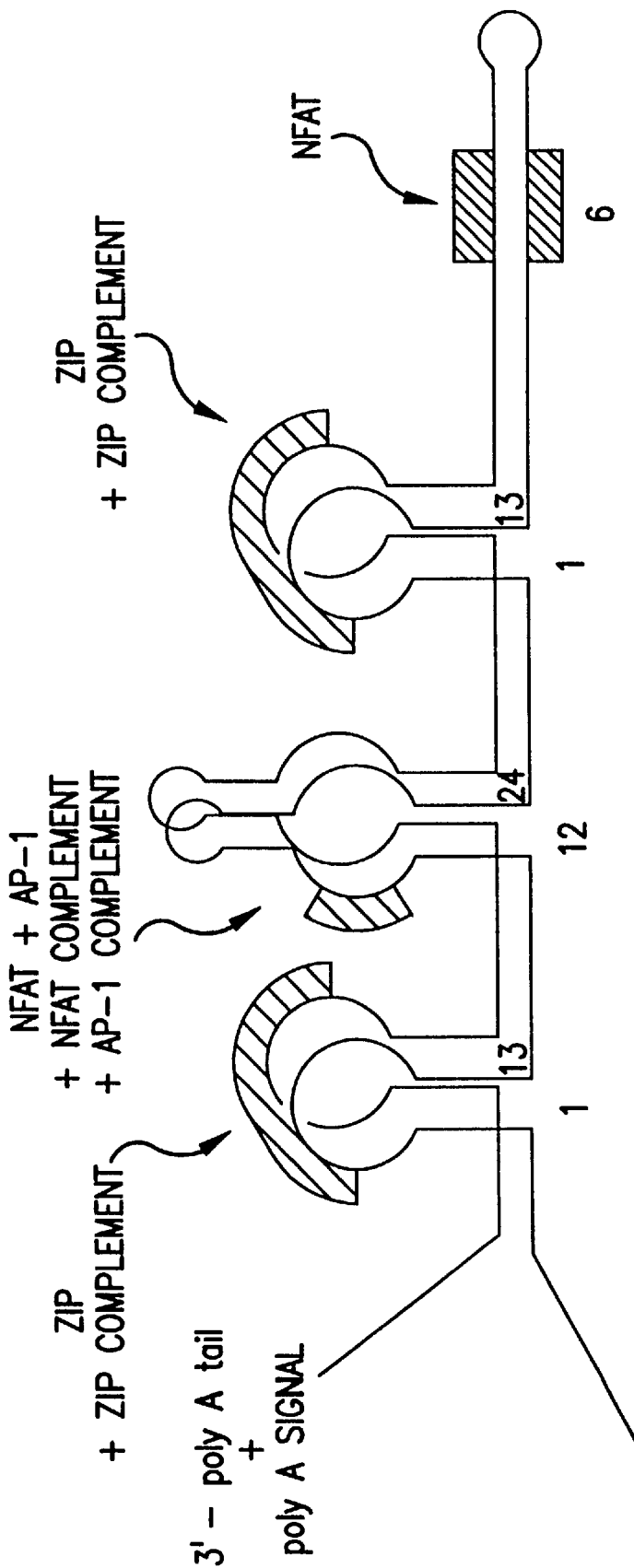

This synthetic IL-2 repressor utron can be folded further to form a more compact structure. The folding is accomplished by replacing the segments a, d, e, i, l, and r as described above with unique sequences so that the set of four double-stranded central stems of the structure would be annealed: $a_1$ to $d_4$, $(d_1+l_1)$ to $(r_2+a_4)$, $(r_1+a_2)$ to $(d_3+l_2)$ and $(d_2+e_1)$ to $(i_1+a_3)$. These palindromic sequences, which can be of any sequence, form four 6 base stems. The predicted folding of this IL-2 repressor utron is depicted in FIG. 14B.

9. SYNTHETIC HIV-1 LTR REPRESSOR UTRON

Two functionally important gene promoter motifs found in the HIV-1 LTR are utilized in the design of the following synthetic repressor utron: NF-KB and SP1 (Gaynor, R., 1992, *AIDS* 6:347–363). There are two particular versions of the 13 bp NF-κB site in the HIV-1 LTR, called NF-κB1

(5'-AGGGACTTTCCGG-3') (SEQ ID NO:48) and NF-κB2 (5'-TGGGGACTTTCCA-3') (SEQ ID NO:49). Because single-stranded DNA or RNA containing these NF-κB sites contain 3 self-complementary bases and would each form a stem-loop structure, variant NF-κB sequences are also utilized containing a perfect half-site as well as a non-palindromic half-site to avoid the formation of the small stem-loops in synthetic utrons. The variant sequences are produced by changing the underlined C residues to A residues. There are three versions of SP1 site, called SP1(3) (5'-GGAGGCGTGGCC-3', 12 bp), (SEQ ID NO:50) SP1(2) (5'-TGGGCGGGAC-3', 10 bp), (SEQ ID NO: 51) and SP1(1) (5'-TGGGGAGTGGC-3', 11 bp) (SEQ ID NO:52).

Listed below are the potential structural components and functional RNA motifs which these components could contain for construction of an HIV-1 LTR repressor utron.

Stem-loop structures:

1. NF-κB1
2. NF-κB1 non-palindromic variant
3. NF-κB2
4. NF-κB2 non-palindromic variant
5. NF-κB1 complement
6. NF-κB1 non-palindromic variant complement
7. NF-κB2 complement
8. NF-κB2 non-palindromic variant complement Hairpin structures:

9. NF-κB1
10. NF-κB2
11. NF-κB1 complement
12. NF-κB2 complement

Bulge structures:

13. NF-κB1
14. NF-κB1 non-palindromic variant
15. NF-κB2
16. NF-κB2 non-palindromic variant
17. NF-κB1 complement
18. NF-κB1 non-palindromic variant complement
19. NF-κB2 complement
20. NF-κB2 non-palindromic variant complement Stem-loop structures:

21. SP1 (3)
22. SP1 (2)
23. SP1 (1)
24. SP1 (3) complement
25. SP1 (2) complement
26. SP1 (1) complement Hairpin structures:

27. SP1 (3)
28. SP1 (2)
29. SP1 (1)

Bulge structures:

30. SP1 (3)
31. SP1 (2)
32. SP1 (1)
33. SP1 (3) complement
34. SP1 (2) complement
35. SP1 (1) complement Additionally, listed below are the specifications for the structural aspects of the HIV-1 LTR repressor utron components where the letters refer to the aspect of the structural component as listed in FIGS. 12A–D.

For stem-loop structures 1–8 and 21–26:

a=4 base random sequence 5'-CCTA-3' b=6 bp double-stranded random sequence stem 5'-AGCATC-3' and its complement d=4 base random sequence 5'-GAAC-3' j=none

For hairpin structures 9–12 and 27–29:

e=6 base random sequence 5'-ATAGCT-3' f=4 bp random sequence 5'-TCTG-3' and its complement g=4 bp random sequence 5'-CTAG-3' and its complement h=6 base loop 5'-CTGAAT-3' i=6 base random sequence 5'-TAATCA-3' j=none

For bulge structures 13–20 and 30–35:

j=none l=e n=4 bp random sequence 5'-AAGC-3' and its complement p=h r=l

For all structures 1–35:

polyadenylation signal=5'-AATAAA 3' contiguous with spacer 5'-ATTCTAGCACT-3' contiguous with $(A)_n$ (polyA tail) to form AATAAAATTCTAGCACT$(A)_n$ (SEQ ID NO:41)

A composite HIV-I LTR repressor utron was designed containing nine of these components, 2, 3, 6, 7, 9, 22, 25, 32 and 35, and its proposed folding pattern is depicted in FIG. 15A. Below are listed the specifications for the HIV-1 LTR repressor utron components as depicted in FIG. 15A, where the letters refer to the designation of the aspects of the structural components as listed in FIGS. 12A–D, in addition to those components specified above.

For hairpin structure 9:

NF-κB1 motif=13 base sequence 5'-AGGGACTTTCCGG-3' (SEQ ID NO:48)

For stem-loop structure 3:

c=5'-TTGGGGACTTTCCA-3' (SEQ ID NO:36)

For bulge structure 32:

k=5'-ACTGGGGAGTGGCGA-3' (SEQ ID NO:54)

q=5'-ATCTGGACGATCAG-3' (SEQ ID NO:55)

For stem-loop structure 22:

c=10 base loop SP1(2) 5'-TGGGCGGGAC-3' (SEQ ID NO:51)

For stem-loop structure 2:

c=5'-TAGGGACTTTACGG-3' (SEQ ID NO:69)

For stem-loop structure 6:

c=14 base (loop) including 13 base NF-KB non-palindromic variant sequence complement 5'-CCGTAAAGTCCCTA-3' (SEQ ID NO:53)

For stem-loop structure 25:

c=5'-GTCCCGCCCA-3' (SEQ ID NO:70)

For bulge structure 35:

k=5'-TCGCCAGTCCCCGT-3' (SEQ ID NO:72)

q=5'-ATCTGGACGATCAG-3' (SEQ ID NO:91)

For stem-loop structure 7:

c=5'-TGGAAAGTCCCCAA-3' (SEQ ID NO:35)

Following the above specifications:

hairpin component structure 9 consists of:

5'-ATAGCTTCTGAGGGACTTTCCGGCTAGCTGAATCTAGCCGGAAAGTCCCTCAG ATAATCA-3' (SEQ ID NO:68)

stem-loop component structure 3 consists of:

5'-CCTAAGCATCTTGGGGACTTTCCAGATGCTGAAC-3' (SEQ ID NO:93)

bulge component structure 32 consists of:
5'-ATAGCTTCTGACTGGGGAGTGGCGAAAGCCT AATGCTTATCTGGACGAT CAGCAGATAATCA-3' (SEQ ID NO:94)
stem loop component structure 22 consists of:
5'-CCTAAGCATCTGGGCGGGACGATGCTGAAC-3' (SEQ ID NO:71)
stem-loop component structure 2 consists of:
5'-CCTAAGCATCTAGGGACTTTACGGGATGCTGA AC-3' (SEQ ID NO:95)
stem-loop component structure 6 consists of:
5'-CCTAAGCATCCCGTAAAGTCCCTAGATGCTGA AC-3' (SEQ ID NO: 73);
stem-loop component structure 25 consists of:
5'-CCTAAGCATCGTCCCGCCCAGATGCTGAAC-3' (SEQ ID NO:96)
bulge component structure 35 consists of:
5'-ATAGCTTCTGTCGCCAGTCCCCGTAAGCCTGA ATGCTTATCTGGACGATCAGC AGATAATCA-3' (SEQ ID NO:97)
stem-loop component structure 7 consists of:
5'-CCTAAGCATCTGGAAAGTCCCCAAGATGCTG AAC-3' (SEQ ID NO:35); and Thus, in a specific embodiment, the invention provides a tron comprising or, alternatively, consisting essentially of airpin component 9, stem loop component 3, bulge component 32, stem loop component 22, stem loop component 2, stem loop component 6, stem loop component 25, bulge component 35, and stem loop component 7, preferably in the $5\mu$ to $3\mu$ order listed, and as shown in FIG. 15A.

The HIV-1 LTR repressor utron can be predicted to fold into a more compact structure as shown in FIG. 15B. The folding is accomplished by replacing the segments a, d, e, i, l, and r, as designated in FIGS. 12A–D, with other sequences so that the set of four double-stranded central stems of the structure would be annealed: $a_1$ to $d_6$, $(d_1+l_1)$ to $(r_2+a_6)$, $(r_1+a_2)$ to $(d_5+l_2)$, $(d_2+a_3)$ to $(d_4+a_5)$, and $d_3+a_4$. These palindromic sequences, which can be of any sequence, would be designed to form five 10 base stems.

10. SUPPRESSION OF MHC CLASS I, MHC CLASS II,

ICAM-1, Fc RECEPTOR, B7-1 and B7-2 ANTIGENS ON MOUSE B LYMPHOCYTES TRANSFECTED WITH AN TSU CDNA EXPRESSION CONSTRUCT

10.1. MATERIALS AND METHODS

10.1.1. LIPOFECTION OF CH27 MOUSE B LYMPHOCYTE CELLS WITH TSU-pREP4 CONSTRUCT

The 0.6 kb TSU PCR product, obtained by PCR amplification of the pCR3 vector using primers pSH4-1 and pSH4-2 (see Section 7.1.1), was subcloned into the T-extended PvuII site of the mammalian expression vector pREP4 (Invitrogen) by TA cloning, and $10^7$ CH27 cells were transfected with the liposome mixture of 10 μg TSU-pREP4 plasmid DNA and 100 μl lipofectin, according to the instructions of the manufacturer (GIBCO). Lipofection using pREP4 plasmid DNA with no cDNA insert was also carried out as a negative control. Selection of cells resistant to 500 μg/μl hygromycin B over 14 to 17 days provided samples for analysis.

10.1.2. IMMUNOCYTOCHEMICAL DETERMINATION OF EXPRESSION OF B CELL ANTIGENS

Binding of biotinylated antibodies was detected by use of avidin-biotinylated-peroxidase immunocytochemistry as described above in Section 7.1.3. Binding of antibodies to the abundant mouse B cell Fc receptors caused very high background staining, and this was eliminated by incubating the rehydrated, acetone-fixed cells first with 2.4G2 mAb (monoclonal antibody to the Fc receptor) (10 μg/μl) and then with non-immune horse serum (10 μg/μl) (Vector Laboratories) and non-immune mouse IgG2a (10 μg/μl) (Sigma), followed by the primary antibodies at the concentrations listed below. All primary antibodies were obtained from Pharmingen, Inc., except CTKk antibody which was obtained from Caltag. The determination of Fc receptor antigen itself was performed using non-biotinylated primary antibody, biotinylated horse-anti-mouse antibody, and avidin-biotinylated peroxidase complex. As shown in FIG. 17, nickel-enhanced 3,3'-diaminobenzidine staining for peroxidase indicated the presence of 100% antigen-positive cells (i.e., 0% negative cells) in the untransfected controls (solid bars), and in the pREP4 vector-transfected controls (not shown). Estimates of negative-staining cells were obtained by visual inspection of >200 cells per sample. The results shown for I-A$^k$, H-2K$^k$ and ICAM-1 antigens, and the isotype controls represent the mean of three preparations from two independent transfections. The results shown for FcγR, B7-2 and B220 antigens represent the mean of two independent preparations, and the results for B7-1 represents a single determination. Other experimental details are set forth in Table 2.

TABLE 2

| Antigen | CD number | Antibody | Species | Conc. (μg/μl) |
|---|---|---|---|---|
| I-A$^k$ | — | biotinylated 11-5.2 IgG2b | mouse | 1 |
| H-2K$^k$ | — | biotinylated CTK$^k$ IgG2a (Caltag) | mouse | 3 |
| ICAM-1 | CD54 | biotinylated 3E2 IgG | hamster | 10 |
| FcγRII/FcγRIII | CD16/CD23 | 2.4G2 IgG2b | rat | 0.001 |
| B7-1 | CD80 | biotinylated IG10 IgG2a | rat | 10 |
| B7-2 | CD86 | biotinylated GL1 IgG2a | rat | 10 |
| B220 | CD45R | biotinylated RA3-6B2 IgG2a | rat | 10 |
| Isotype control | — | biotinylated non-immune 49.2 IgG2b | mouse | 10 |
| Isotype control | — | biotinylated non-immune UC8-4B3 IgG | hamster | 10 |
| Isotype control | — | biotinylated non-immune R35-95 IgG2a | rat | 10 |

10.2. RESULTS AND DISCUSSION

In short-term stable transfection experiments, transfection with the TSU expression construct produced 40% to 80% of the cells that did not stain for intracellular or membrane antigens detected by mAb for the mouse MHC class II I-A$^k$, the MHC class I H-2K$^k$, the cell adhesion molecule ICAM-1, the two immunoglobulin Fc receptors FcγRII and FcγRIII, and the two co-stimulatory molecules B7-1 and B7-2 (FIG. 17, cross-hatched bars), whereas the B220 positive control antigen was unaffected. Negative controls were consistently negative. Some cells in the cultures of TSU-transfected cells remained antigen-positive, and it appears that the combination of mouse B cells and human episomal vector may not be optimal for stable transfection. The pREP4 vector expresses the EBNA-1 gene, and the EBNA-1 protein trans-activates the oriP replication origin; the system results in satisfactory episomal replication and RSV-3'-LTR driven expression of constructs in human B cells, but in mouse B cells there is variable integration into the chromosomal DNA and continual loss of clones due to dilution of the episomal vector upon mitosis (according to information provided by the manufacturer). The selected CH27 cells were observed to undergo continual cell death over several months under carefully maintained culture conditions with both TSU-pREP4 and pREP4 transfected DNA, and observation of revertants with the phenotype of untransfected cells was therefore not unexpected. The human trophoblast TSU cDNA, however, was observed to suppress 6 constitutively expressed mouse B cell molecules, each of which is involved in antigen presentation and B cell-T cell interaction. The suppression of B lymphocyte expression of MHC and other antigens was predicted from the transient heterokaryon studies of a human trophoblast and a human B lymphocyte cell line, as described above.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties.

What is claimed is:

1. An isolated single-stranded nucleic acid molecule comprising at least one nucleotide sequence comprising at least one promoter regulatory motif, said at least one nucleotide sequence being contiguous with a heterologous nucleotide sequence of at least 20 nucleotides.

2. The molecule of claim 1 that is an RNA.

3. An isolated nucleic acid comprising a promoter operably linked to a nucleotide sequence that can be transcribed to produce the single-stranded RNA molecule of claim 2, in which said RNA molecule is not more than 1,000 bases in length.

4. The molecule of claim 1 that is an DNA.

5. The molecule of claim 1 in which the promoter regulatory motif is selected from the group consisting of a GAS motif, GAS complement motif, ISRE motif, and ISRE complement motif.

6. The molecule of claim 1 in which the promoter regulatory motif is a promoter regulatory motif of an oncogene.

7. The molecule of claim 1 in which the promoter regulatory motif is a promoter regulatory motif of a cell cycle control gene.

8. The molecule of claim 1 which is an RNA in which the promoter regulatory motif is at least one pair of complementary promoter regulatory motif sequences selected from the group consisting of (a) a GAS motif and GAS complement motif, and (b) an ISRE motif and ISRE complement motif; and in which hydrogen bonding can occur when the motifs of the pair are aligned by folding the RNA in an antiparallel orientation using one or more intramolecular A-U, C-G, G-U, and/or A-G base-pairs, and in which the intermotif hydrogen bonding between a GAS motif and GAS complement motif can occur at at least positions 1–4 and 8–9 of the GAS motif; and in which the inter-motif hydrogen bonding between an ISRE motif and an ISRE complement motif can occur at at least positions 1–6 and 9–10 of the ISRE motif.

9. An isolated single-stranded nucleic acid molecule comprising at least one nucleotide sequence comprising at least one promoter regulatory motif, said at least one nucleotide sequence being contiguous with a heterologous nucleotide sequence of at least 20 nucleotides, in which said promoter regulatory motif is a promoter element of a human, animal or plant pathogen.

10. An isolated nucleic acid having the sequence depicted in FIG. 5B (SEQ ID NO:1).

11. An isolated nucleic acid comprising the sequence depicted in FIG. 5B (SEQ ID NO:1) or FIG. 16 (SEQ ID NO:86).

12. A pharmaceutical composition comprising the nucleic acid of claim 11 in a pharmaceutically acceptable carrier.

13. An isolated single-stranded RNA molecule comprising at least two component structures selected from the group consisting of:

a stem-loop component structure consisting of:
(a) a first sequence in the range of 10–20 bases, consisting of (i) one or more promoter regulatory motifs, each motif optionally separated from each other motif by a number of bases, (ii) optional flanking sequences 5' to said one or more promoter regulatory motifs, and (iii) optional flanking sequences 3' to said one or more promoter regulatory motifs;
(b) a second sequence of 5–10 bases flanking said first sequence on the 5' side; and
(c) a third sequence flanking said first sequence on the 3' side, said second and third sequences being of equal length and complementary to each other in inverse order;

said stem-loop component structure optionally further consisting of:
(d) a fourth sequence flanking said second sequence on the 5' side, in the range of 1–10 bases; and/or
(e) a fifth sequence flanking said third sequence on the 3' side, in the range of 1–10 bases;

a hairpin component structure consisting of:
(a) a first sequence in the range of 4–6 bases;
(b) a second sequence consisting of (i) one or more promoter regulatory motifs, each motif optionally separated from each other motif by a number of bases; (ii) a flanking sequence of 5–10 bases 3' to said one or more promoter regulatory motifs; and (iii) a flanking sequence of 5–10 bases 5' to said one or more promoter regulatory motifs; in which either the flanking sequence 3' to the one or more promoter regulatory motifs or the flanking sequence 5' to the one or more promoter regulatory motifs is contiguous with said first sequence; and
(c) a third sequence of equal length as said second sequence and complementary in inverse order to said second sequence;

said hairpin component structure optionally further consisting of:
(d) a fourth sequence in the range of 1–10 bases, flanking said second sequence; and/or
(e) a fifth sequence in the range of 1–10 bases, flanking said third sequence; and a bulge component structure consisting of:

(a) a first sequence in the range of 4–6 bases;
(b) a second sequence of 5–10 bases 5' to said first sequence;
(c) a third sequence 3' to said first sequence and of equal length as said second sequence and complementary in inverse order to said second sequence;
(d) a fourth sequence of 6–20 bases 5' to said second sequence and consisting of one or more promoter regulatory motifs, each motif optionally separated from each other motif by a number of bases;
(e) a fifth sequence of 6–20 bases 3' to said third sequence;
(f) a sixth sequence of 5–10 bases 5' to said fourth sequence; and
(g) a seventh sequence 3' to said fifth sequence and of equal length as said sixth sequence and complementary in inverse order to said sixth sequence;
said bulge component structure optionally further consisting of:
(h) an eighth sequence in the range of 1–10 bases, 5' to said sixth sequence; and
(i) a ninth sequence in the range of 1–10 bases, 3' to said seventh sequence
in which at least one of the component structures is heterologous with respect to at least one of the other component structures.

14. The molecule of claim 13 in which one or more promoter regulatory motifs are greater than 50% complementary when aligned using one or more intramolecular A-U, C-G, G-U and/or A-G base-pairs.

15. An isolated single stranded DNA molecule comprising one or more component structures selected from the group consisting of:
a stem-loop component structure consisting of:
(a) a first sequence in the range of 10–20 bases, consisting of (i) one or more promoter regulatory motifs, each motif optionally separated from each other motif by a number of bases, (ii) optional flanking sequences 5' to said one or more promoter regulatory motifs, and (iii) optional flanking sequences 3' to said one or more promoter regulatory motifs;
(b) a second sequence of 5–10 bases flanking said first sequence on the 5' side; and
(c) a third sequence flanking said first sequence on the 3' side, said second and third sequences being of equal length and complementary to each other in inverse order;
said stem-loop component structure optionally further consisting of:
(d) a fourth sequence flanking said second sequence on the 5' side, in the range of 1–10 bases; and/or
(e) a fifth sequence flanking said third sequence on the 3' side, in the range of 1–10 bases;
a hairpin component structure consisting of:
(a) a first sequence in the range of 4–6 bases;
(b) a second sequence consisting of (i) one or more promoter regulatory motifs, each motif optionally separated from each other motif by a number of bases; (ii) a flanking sequence of 5–10 bases 3' to said one or more promoter regulatory motifs; and (iii) a flanking sequence of 5–10 bases 5' to said one or more promoter regulatory motifs; in which either the flanking sequence 3' to the one or more promoter regulatory motifs or the flanking sequence 5' to the one or more promoter regulatory motifs is contiguous with said first sequence; and
(c) a third sequence of equal length as said second sequence and complementary in inverse order to said second sequence;
said hairpin component structure optionally further consisting of:
(d) a fourth sequence in the range of 1–10 bases, flanking said second sequence; and/or
(e) a fifth sequence in the range of 1–10 bases, flanking said third sequence; and
a bulge component structure consisting of:
(a) a first sequence in the range of 4–6 bases;
(b) a second sequence of 5–10 bases 5' to said first sequence;
(c) a third sequence 3' to said first sequence and of equal length as said second sequence and complementary in inverse order to said second sequence;
(d) a fourth sequence of 6–20 bases 5' to said second sequence and consisting of one or more promoter regulatory motifs, each motif optionally separated from each other motif by a number of bases;
(e) a fifth sequence of 6–20 bases 3' to said third sequence;
(f) a sixth sequence of 5–10 bases 5' to said fourth sequence; and
(g) a seventh sequence 3' to said fifth sequence and of equal length as said sixth sequence and complementary in inverse order to said sixth sequence;
said bulge component structure optionally further consisting of:
(h) an eighth sequence in the range of 1–10 bases, 5' to said sixth sequence; and/or
(i) a ninth sequence in the range of 1–10 bases, 3' to said seventh sequence,
in which at least one of the component structures is heterologous with respect to at least one of the other component structures.

16. The molecule of claim 15 which comprises one or more pairs of promoter regulatory motifs, the motifs within each pair being greater than 50% complementary when aligned using one or more intramolecular A-T and/or C-G base-pairs.

17. An isolated single-stranded nucleic acid molecule comprising at least one nucleotide sequence comprising at least one promoter regulatory motif, said at least one nucleotide sequence being contiguous with a heterologous nucleotide sequence of at least 20 nucleotides, in which said promoter regulatory motif is selected from the group consisting of ZIP, NF-AT, AP-1, and a complement of the foregoing.

18. An isolated single-stranded nucleic acid molecule comprising at least one nucleotide sequence comprising at least one promoter regulatory motif, said at least one nucleotide sequence being contiguous with a heterologous nucleotide sequence of at least 20 nucleotides, in which said promoter regulatory motif is selected from the group consisting of NF-κB of an HIV LTR, SP1 of an HIV LTR, an NF-κB variant having the sequence 5'-AGGGACTTTACGG-3' (SEQ ID NO:98), an NF-κB variant having the sequence 5'-TGGGGACTTTCAA-3' (SEQ ID NO:99), and a complement of the foregoing.

19. A pharmaceutical composition comprising the nucleic acid of claim 17 or 18 in a pharmaceutically acceptable carrier.

20. The molecule of claim 18 which is an RNA which comprises one or more pairs of promoter regulatory motifs, the motifs within each pair being greater than 50% complementary when aligned using one or more intramolecular A-U, C-G, G-U, and/or A-G base-pairs.

21. The molecule of claim 18 which is a DNA which comprises one or more pairs of promoter regulatory motifs, the motifs within each pair being greater than 50% complementary when aligned using one or more intramolecular A-T and/or C-G base-pairs.

22. An RNA molecule comprising:
a first stem-loop component structure consisting of:
ATACGGATCGCATCCCCACCCTGGCGATCATACG (SEQ ID NO:75);
a first bulge component structure consisting of:
5'-ATACGGATCGAGGAGGAAAAACTGTTTCATAC GGATCGCTGAATCGATCTTCA CACTGCCTAGATACTCGATCATACG-3' (SEQ ID NO:66);
a second stem-loop component structure consisting of:
ATACGGATCGCATCCCCACCCTGGCGATCATACG (SEQ ID NO:75);
a hairpin component structure consisting of:
5'-ATACGACAGGGAAAAACAGCTGAATCTGTTTT TCCCTGTATACG-3' (SEQ ID NO:65);
a third stem-loop component structure consisting of:
ATACGGATCGCATGGGTGGGGTGGCGATCATACG (SEQ ID NO:76);
a second bulge component structure consisting of:
5'-ATACGGATCGCGTATGAAACAGTTTTTCCTCCT GATCGCTGAATCGATCGAGT ATCTAGGCAGTCTGAACGATCATACG-3' (SEQ ID NO:67);
a fourth stem-loop component structure consisting of:
ATACGGATCGCATGGGTGGGGTGGCGATCATACG (SEQ ID NO:76); and
a 3' polyadenylation signal consisting of:
5'-AATAAA-3', contiguous with a 10–20 base spacer contiguous with a poly A tail;
or a DNA analog thereof.

23. An RNA molecule comprising:
a first hairpin component structure consisting of:
5'-ATAGCTTCTGAGGGACTTTCCGGCTAGCTGAA TCTAGCCGGAAAGTCCCTCAG ATAATCA-3' (SEQ ID NO:68);
a first stem-loop component structure consisting of:
5'-CCTAAGCATCTTGGGGACTTTCCAGATGCTGA AC-3'(SEQ ID NO:93)
a first bulge component structure consisting of:
5'-ATAGCTTCTGACTGGGGAGTGGCGAAAGCCT GAATGCTTATCTGGACGAT CAGCAGATAATCA-3' (SEQ ID NO:94)
a second stem-loop component structure consisting of:
5'-CCTAAGCATCTGGGCGGGACGATGCTGAAC-3' (SEQ ID NO:71);
a third stem-loop component structure consisting of:
5'-CCTAAGCATCTAGGGACTTTACGGGATGCTGA AC-3' (SEQ ID NO:95)
a fourth stem-loop component structure consisting of:
5'-CCTAAGCATCCCGTAAAGTCCCTAGATGCTGA AC-3' (SEQ ID NO:73);
a fifth stem-loop component structure consisting of:
5'-CCTAAGCATCGTCCCGCCCAGATGCTGAAC-3' (SEQ ID NO:96)
a second bulge component structure consisting of:
5'-ATAGCTTCTGTCGCCAGTCCCCGTAAGCCTGA ATGCTTATCTGGACGATCAG CAGATAATCA-3' (SEQ ID NO:97)

a sixth stem-loop component structure consisting of:
5'-CCTAAGCATCTGGAAAGTCCCCAAGATGCTGA AC-3' (SEQ ID NO: 35); and
a 3' polyadenylation signal consisting of:
5'-AATAAA-3', contiguous with a 10–20 base spacer contiguous with a poly A tail;
or a DNA analog thereof.

24. The molecule of claim 22 or 23 which comprises one or more pairs of promoter regulatory motifs, the motifs within each pair being greater than 50% complementary when aligned using one or more intramolecular A-U, C-G, G-U, and/or A-G base-pairs.

25. An isolated nucleic acid having a sequence complementary to the sequence depicted in FIG. 5B (SEQ ID NO:1).

26. An isolated single-stranded DNA comprising a nucleotide sequence selected from the group consisting of
5'-CGATCGGTGAAATTGAAACTCGATCG-3' (SEQ ID NO:33),
5'-CGATGTTGCTCTGTATGGTAAGAACATCG-3' (SEQ ID NO:31), and
5'-ACTTTFCTTCCCCTTTACAGCACAAATAAAGT-3' (SEQ ID NO:29) that is a fragment of an TSU nucleic acid having the nucleotide sequence depicted in FIG. 5B (SEQ ID NO:1).

27. An isolated nucleic acid comprising a promoter operably linked to a nucleotide sequence that can be transcribed to produce an RNA molecule comprising at least one nucleotide sequence comprising at least one promoter regulatory motif, said at least one nucleotide sequence being contiguous with a heterologous nucleotide sequence of at least 20 nucleotides, in which said RNA molecule is not more than 1,000 bases in length, in which said promoter regulator motif is not a regulatory motif of said operably linked promoter.

28. A pharmaceutical composition comprising an isolated single-stranded nucleic acid molecule comprising at least one nucleotide sequence comprising at least one promoter regulatory motif, said at least one nucleotide sequence being contiguous with a heterologous nucleotide sequence of at least 20 nucleotides, in a pharmaceutically acceptable carrier.

29. A method of preparing a chimeric cell for producing a transgenic non-human animal comprising introducing into an ovum or embryonic stem cell of a non-human animal an isolated nucleic acid comprising a promoter operably linked to a nucleotide sequence that can be transcribed to produce an RNA molecule comprising at least one nucleotide sequence comprising at least one promoter regulatory motif, said at least one nucleotide sequence being contiguous with a heterologous nucleotide sequence of at least 20 nucleotides, in which said RNA molecule is not more than 1,000 bases in length.

30. A method of producing an RNA molecule comprising at least one nucleotide sequence comprising at least one promoter regulatory motif, said at least one nucleotide sequence being contiguous with a heterologous nucleotide sequence of at least 20 nucleotides, said method comprising (a) culturing a recombinant cell containing a nucleic acid comprising a promoter operably linked to a nucleotide sequence that can be transcribed to produce the RNA molecule, such that the RNA molecule is produced by the cell, in which the promoter regulatory motif is not a regulatory motif of said operably linked promoter; and (b) recovering the produced RNA molecule.

31. An isolated single-stranded nucleic acid molecule comprising at least one nucleotide sequence comprising at least one promoter regulatory motif, said at least one nucleotide sequence being contiguous with a heterologous nucleotide sequence of at least 20 nucleotides, in which the promoter regulatory motif is a promoter regulatory motif of a gene of a human or animal pathogen.

32. A recombinant cell containing a nucleic acid comprising a promoter operably linked to a nucleotide sequence that can be transcribed to produce a single-stranded RNA molecule comprising at least one nucleotide sequence comprising at least one promoter regulatory motif, said at least one nucleotide sequence being contiguous with a heterologous nucleotide sequence of at least 20 nucleotides, said RNA molecule not being more than 1,000 bases in length, and in which said promoter regulatory motif is not a regulatory motif of said operably linked promoter.

33. The recombinant cell of claim 32 which also contains a recombinant nucleic acid encoding and capable of expressing a product that is therapeutically effective for the treatment of a disease or disorder.

34. A pharmaceutical composition comprising the recombinant cell of claim 32 in a pharmaceutically acceptable carrier.

35. A recombinant tissue or organ containing a nucleic acid comprising a promoter operably linked to a nucleotide sequence that can be transcribed to produce a single-stranded RNA molecule comprising at least one nucleotide sequence comprising at least one promoter regulatory motif, said at least one nucleotide sequence being contiguous with a heterologous nucleotide sequence of at least 20 nucleotides, said RNA molecule not being more than 1,000 bases in length, and in which said promoter regulatory motif is not a regulatory motif of said operably linked promoter.

36. A pharmaceutical composition comprising a nucleic acid comprising a promoter operably linked to a nucleotide sequence that can be transcribed to produce a single-stranded RNA molecule comprising at least one nucleotide sequence comprising at least one promoter regulatory motif, said at least one nucleotide sequence being contiguous with a heterologous nucleotide sequence of at least 20 nucleotides, said RNA molecule not being more than 1,000 bases in length, in a pharmaceutically acceptable carrier.

37. An isolated single-stranded RNA molecule comprising at least two component structures selected from the group consisting of:

a stem-loop component structure consisting of:
(a) a first sequence in the range of 10–50 bases, consisting of (i) one or more promoter regulatory motifs, each motif optionally separated from each other motif by a number of bases, (ii) an optional flanking sequence 5' to said one or more promoter regulatory motifs, and (iii) an optional flanking sequence 3' to said one or more promoter regulatory motifs;
(b) a second sequence of 4–20 bases flanking said first sequence on the 5' side; and
(c) a third sequence flanking said first sequence on the 3' side, said second and third sequences being of equal length and complementary to each other in inverse order;

said stem-loop component optionally further consisting of:
(d) a fourth sequence flanking said second sequence on the 5' side, in the range of 1–100 bases; and/or
(e) a fifth sequence flanking said third sequence on the 3' side, in the range of 1–100 bases;

a hairpin component structure consisting of:
(a) a first sequence in the range of 1–8 bases;
(b) a second sequence consisting of (i) one or more promoter regulatory motifs, each motif optionally separated from each other motif by a number of bases; (ii) an optional flanking sequence of 1–20 bases 3' to said one or more promoter regulatory motifs; and (iii) an optional flanking sequence of 1–20 bases 5' to said one or more promoter regulatory motifs; in which either the flanking sequence 3' to the one or more promoter regulatory motifs or the flanking sequence 5' to the one or more promoter regulatory motifs is contiguous with said first sequence; and
(c) a third sequence of equal length as said second sequence and complementary in inverse order to said second sequence;

said hairpin component structure optionally further consisting of:
(d) a fourth sequence in the range of 1–100 bases, flanking said second sequence; and/or
(e) a fifth sequence in the range of 1–100 bases, flanking said third sequence; and a bulge component structure consisting of:
(a) a first sequence in the range of 1–8 bases;
(b) a second sequence of 4–20 bases 5' to said first sequence;
(c) a third sequence 3' to said first sequence and of equal length as said second sequence and complementary in inverse order to said second sequence;
(d) a fourth sequence of 4–50 bases 5' to said second sequence and consisting of one or more promoter regulatory motifs, each motif optionally separated from each other motif by a number of bases;
(e) optionally a fifth sequence of 1–50 bases 3' to said third sequence;
(f) a sixth sequence of 4–20 bases 5' to said fourth sequence;
(g) a seventh sequence 3' to said fifth sequence and of equal length as said sixth sequence and complementary in inverse order to said sixth sequence;
(h) optionally, an eighth sequence in the range of 1–100 bases, 5' to said sixth sequence; and
(i) optionally, a ninth sequence in the range of 1–100 bases, 3' to said seventh sequence;

in which at least one of the component structures is heterologous with respect to at least one of the other component structures.

38. An isolated single stranded DNA molecule comprising one or more component structures selected from the group consisting of:

a stem-loop component structure consisting of:
(a) a first sequence in the range of 10–50 bases, consisting of (i) one or more promoter regulatory motifs, each motif optionally separated from each other motif by a number of bases, (ii) optional flanking sequences 5' to said one or more promoter regulatory motifs, and (iii) optional flanking sequences 3' to said one or more promoter regulatory motifs;
(b) a second sequence of 4–20 bases flanking said first sequence on the 5' side; and
(c) a third sequence flanking said first sequence on the 3' side, said second and third sequences being of equal length and complementary to each other in inverse order;

said stem-loop component structure optionally further consisting of:
(d) a fourth sequence flanking said second sequence on the 5' side, in the range of 1–100 bases; and/or (e) a fifth sequence flanking said third sequence on the 3' side, in the range of 1–100 bases;

a hairpin component structure consisting of:
(a) a first sequence in the range of 1–8 bases;
(b) a second sequence consisting of (i) one or more promoter regulatory motifs, each motif optionally separated from each other motif by a number of bases; (ii) an optional flanking sequence of 1–20 bases 3' to said one or more promoter regulatory motifs; and (iii) an optional flanking sequence of 1–20 bases 5' to said one or more promoter regulatory motifs; in which either the flanking sequence 3' to the one or more promoter regulatory motifs or the flanking sequence 5' to the one or more promoter regulatory motifs is contiguous with said first sequence; and
(c) a third sequence of equal length as said second sequence and complementary in inverse order to said second sequence;

said hairpin component structure optionally further consisting of:
(d) a fourth sequence in the range of 1–100 bases, flanking said second sequence; and/or
(e) a fifth sequence in the range of 1–100 bases, flanking said third sequence; and a bulge component structure consisting of:
(a) a first sequence in the range of 1–8 bases;
(b) a second sequence of 4–20 bases 5' to said first sequence;
(c) a third sequence 3' to said first sequence and of equal length as said second sequence and complementary in inverse order to said second sequence;
(d) a fourth sequence of 4–50 bases 5' to said second sequence and consisting of one or more promoter regulatory motifs, each motif optionally separated from each other motif by a number of bases;
(e) optionally a fifth sequence of 1–50 bases 3' to said third sequence;
(f) a sixth sequence of 4–20 bases 5' to said fourth sequence;
(g) a seventh sequence 3' to said fifth sequence and of equal length as said sixth sequence and complementary in inverse order to said sixth sequence;
(h) optionally an eighth sequence in the range of 1–100 bases, 5' to said sixth sequence; and
(i) optionally a ninth sequence in the range of 1–100 bases, 3' to said seventh sequence, in which at least one of the component structures is heterologous with respect to at least one of the other component structures.

39. An isolated RNA having the sequence depicted in FIG. 16 (SEQ ID NO:86).

40. The isolated single-stranded RNA of claim 37 in which at least one of said component structures contains a promoter regulatory motif having a sequence selected from the group consisting of: GUGAAAUUGAAACU (SEQ ID NO:84), GUAUGGUAA (SEQ ID NO:80), and UUACAGCAC (SEQ ID NO:85).

41. The molecule of claim 37 which further comprises a 3' polyA tail.

42. The molecule of claim 37 which further comprises a 5' cap.

43. The molecule of claim 37, 41 or 42 which comprises one or more pairs of promoter regulatory motifs, the motifs within each pair being greater than 50% complementary when aligned using one or more intramolecular A-U, C-G, G-U, and/or A-G base-pairs.

44. A pharmaceutical composition comprising the isolated single-stranded RNA of claim 37 wherein at least one of said component structures contains a promoter regulatory motif selected from the group consisting of:
GUAAAGUAA (SEQ ID NO:77),
UUCCCUUUAA (SEQ ID NO:78),
AGUUUCACUUGAAA (SEQ ID NO:79),
GUAUGGUAA (SEQ ID NO:80),
UUACGUCAU (SEQ ID NO:81),
UUACUAAUCA (SEQ ID NO:82),
AGUUUGAGUUCUAA (SEQ ID NO:83),
AGUUUCNNUUCNC/U (SEQ ID NO: 100), and
UUNCNNNAA (SEQ ID NO: 101); wherein N is any nucleotide;
and a pharmaceutically acceptable carrier.

45. The isolated single-stranded RNA of claim 37 wherein at least one of said component structures contains a promoter regulatory motif selected from the group consisting of:
GUAAAGUAA (SEQ ID NO:77),
UUCCCUUUAA (SEQ ID NO:78),
AGUUUCACUUGAAA (SEQ ID NO:79),
GUAUGGUAA (SEQ ID NO:80),
UUACGUCAU (SEQ ID NO:81),
UUACUAAUCA (SEQ ID NO:82),
AGUUUGAGUUCUAA (SEQ ID NO:83),
AGUUUCNNUUCNC/U (SEQ ID NO: 100), and
UUNCNNNAA (SEQ ID NO: 101); wherein N is any nucleotide.

46. An isolated DNA analog of the RNA of claim 45.

47. The nucleic acid of claim 46 which is a DNA containing at least one phosphorothioate in place of a phosphate on the DNA.

48. An isolated single-stranded RNA comprising at least three promoter regulatory motifs selected from the group consisting of: GUGAAAUUGAAACU (SEQ ID NO:84), GUAUGGUAA (SEQ ID NO:80), and UUACAGCAC (SEQ ID NO:85), each motif separated from another promoter regulatory motif by 2–300 contiguous bases, or a DNA analog thereof.

49. An isolated nucleic acid comprising a promoter operably linked to a nucleotide sequence that can be transcribed to produce the single-stranded RNA molecule of claim 39, 45 or 48.

50. A method of producing an RNA molecule comprising (a) culturing a recombinant cell containing a nucleic acid comprising a promoter operably linked to a nucleotide sequence that can be transcribed to produce the RNA molecule of claim 39, 45, or 48 such that the RNA molecule is produced by the cell; and (b) recovering the produced RNA molecule.

51. The isolated single-stranded RNA of claim 48 in which at least one of the promoter regulatory motifs is heterologous with respect to at least one of the other promoter regulatory motifs.

52. An isolated DNA analog of the RNA of claim 48.

53. The nucleic acid of claim 52 which is a DNA containing at least one phophorothioate in place of a phosphate on the DNA.

54. The molecule of claim 45 in which one or more promoter regulatory motifs are greater than 50% complementary hen aligned using one or more intramolecular A-U, C-G, G-U, and/or A-G base-pairs.

55. A recombinant cell containing the nucleic acid of claim 49 in which said promoter regulatory motif is not a regulatory motif of said operably linked promoter.

56. A recombinant tissue or organ containing the nucleic acid of claim 49, in which said promoter regulatory motif is not a regulatory motif of said operably linked promoter.

57. A non-human transgenic animal containing the nucleic acid of claim 49, in which said promoter regulatory motif is not a regulatory motif of said operably linked promoter.

58. The non-human transgenic animal of claim 57, in which the animal is also transgenic for human HLA-G, human $\beta_2$ microglobulin, and at least one gene selected from the group consisting of the human CD46 gene, human CD55 gene, and human CD59 gene.

59. An isolated nucleic acid comprising a promoter operably linked to a nucleotide sequence that can be transcribed to produce the single-stranded RNA molecule of claim 37.

60. An isolated nucleic acid comprising a promoter operably linked to a first nucleotide sequence that can be transcribed to produce the single-stranded RNA molecule of claim 37, in which at least one of the component structures of said RNA molecule comprises a second nucleotide sequence of at least 20 nucleotides that (a) is contiguous with a third nucleotide sequence comprising the one or more promoter regulatory motifs and (b) is heterologous with respect to the third nucleotide sequence comprising the one or more promoter regulatory motifs.

61. The nucleic acid of claim 59 in which said promoter regulatory motif is not a regulatory motif of said operably linked promoter.

62. A recombinant cell containing the nucleic acid of claim 59 or 60, in which said promoter regulatory motif is not a regulatory motif of said operably linked promoter.

63. A recombinant tissue or organ containing the nucleic acid of claim 59 or 60, in which said promoter regulatory motif is not a regulatory motif of said operably linked promoter.

64. A non-human transgenic animal containing the nucleic acid of claim 59 or 60, in which said promoter regulatory motif is not a regulatory motif of said operably linked promoter.

65. The recombinant cell of claim 62 which also contains a recombinant nucleic acid encoding and capable of expressing a product that is therapeutically effective for the treatment of a disease or disorder.

66. A pharmaceutical composition comprising the recombinant cell of claim 62 in a pharmaceutically acceptable carrier.

67. The molecule of claim 37 or 38 that consists of 5–25 component structures.

68. The molecule of claim 37 or 38 that does not contain an open reading frame.

69. The molecule of claim 38 that contains at least one phosphorothioate in place of a phosphate group on the DNA molecule.

70. The molecule of claim 38 or 69 which further comprises one or more pairs of promoter regulatory motifs, the motifs within each pair being greater than 50% complementary when aligned using one or more intramolecular A-T and or C-G base-pairs.

71. The isolated single-stranded DNA molecule of claim 38 in which at least one of said component structures contains a promoter regulatory motif having the following sequence:
GTGAAATTGAAACT (SEQ ID NO: 7).

72. The isolated single-stranded DNA molecule of claim 38 in which at least one of said component structures contains a promoter regulatory motif having the following sequence: GTATGGTAA (SEQ ID NO: 8).

73. The isolated single-stranded DNA molecule of claim 38 in which at least one of said component structures contains a promoter regulatory motif having the following sequence: TTACAGCAC (SEQ ID NO: 11).

74. An isolated RNA analog of the single-stranded DNA of claim 71, 72 or 73.

75. The isolated single-stranded DNA molecule of claim 38 in which at least one of said component structures contains the following sequence: 5'-CGATCGGTGAAATTGAAACTCGATCG-3' (SEQ ID NO:33).

76. The isolated single-stranded DNA molecule of claim 38 in which at least one of said component structures contains the following sequence: 5'-CGATGTTGCTCTGTATGGTAAGAACATCG-3' (SEQ ID NO:31).

77. The isolated single-stranded DNA molecule of claim 38 in which at least one of said component structures contains the following sequence: 5'-ACTTTTCTTCCCCTITACAGCACAAATAAAGT-3' (SEQ ID NO:29).

\* \* \* \* \*

SEQUENCE LISTING (1) GENERAL INFORMATION:

(iii) NUMBER OF SEQUENCES: 101

(2) INFORMATION FOR SEQ ID NO:1:

(i) SEQUENCE CHARACTERISTICS:
       (A) LENGTH: 481 base pairs
       (B) TYPE: nucleic acid
       (C) STRANDEDNESS: single
       (D) TOPOLOGY: unknown (ii) MOLECULE TYPE: cDNA (xi) SEQUENCE DESCRIPTION: SEQ ID NO:1:

```
AAGCGGCGAG GTGCCTTTAC TACATGTGTG ATCTGAAAAC CCTGCTTGGT TCTGAGCTGC      60

GTCTATTGAA TTGGTAAAGT AATACCAATG GCTTTTTATC ATTTCCTTCT TCCCTTTAAG     120

TTTCACTTGA AATTTTAAAA ATCATGGTTA TTTTTATCGT TGGGATCTTT CTGTCTTCTG     180

GGTTCCATTT TTTAAATGTT TAAAAATATG TTGACATGGT AGTTCAGTTC TTAACCAATG     240

ACTTGGGGAT GATGCAAACA ATTACTGTCG TTGGGATTTA GAGTGTATTA GTCACGCATG     300

TATGGGGAAG TAGTCTCGGG TATGCTGTTG TGAAATTGAA ACTGTAAAAG TAGATGGTTG     360

AAAGTACTGG TATGTTGCTC TGTATGGTAA GAACTAATTC TGTTACGTCA TGTACATAAT     420

TACTAATCAC TTTTCTTCCC CTTTACAGCA CAAATAAAGT TTGAGTTCTA AACTCATTAA     480

A                                                                     481
```

(2) INFORMATION FOR SEQ ID NO:2:

(i) SEQUENCE CHARACTERISTICS:
       (A) LENGTH: 9 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:2:

GTAAAGTAA                                                                9

(2) INFORMATION FOR SEQ ID NO:3:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

TTCCCTTTAA                                                               10

(2) INFORMATION FOR SEQ ID NO:4:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

AGTTTCACTT GAAA                                                          14

(2) INFORMATION FOR SEQ ID NO:5:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

AGTTCAGTTC TTA                                                           13

(2) INFORMATION FOR SEQ ID NO:6:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

TATGGGGAA                                                                9

(2) INFORMATION FOR SEQ ID NO:7:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

GTGAAATTGA AACT                                                          14

(2) INFORMATION FOR SEQ ID NO:8:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

```
GTATGGTAA                                                                9
```

(2) INFORMATION FOR SEQ ID NO:9:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

```
TTACGTCAT                                                                9
```

(2) INFORMATION FOR SEQ ID NO:10:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

```
TTACTAATCA                                                              10
```

(2) INFORMATION FOR SEQ ID NO:11:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

```
TTACAGCAC                                                                9
```

(2) INFORMATION FOR SEQ ID NO:12:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

```
AATAAA                                                                   6
```

(2) INFORMATION FOR SEQ ID NO:13:

(i) SEQUENCE CHARACTERISTICS:
        (A) LENGTH: 14 base pairs (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

AGTTTGAGTT CTAA                                                          14

(2) INFORMATION FOR SEQ ID NO:14:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

CCGTAAAGTC CCTA                                                          14

(2) INFORMATION FOR SEQ ID NO:15:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

AGGGACTTTC CGG                                                           13

(2) INFORMATION FOR SEQ ID NO:16:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

TGGGGACTTT CCA                                                           13

(2) INFORMATION FOR SEQ ID NO:17:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

TTGAAAGTCC CCATGA                                                        16

(2) INFORMATION FOR SEQ ID NO:18:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

GCCACTCCCC A                                                                11

(2) INFORMATION FOR SEQ ID NO:19:

(i) SEQUENCE CHARACTERISTICS:
              (A) LENGTH: 11 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:19:

TGGGGAGTGG C                                                                11

(2) INFORMATION FOR SEQ ID NO:20:

(i) SEQUENCE CHARACTERISTICS:
              (A) LENGTH: 13 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:20:

AGTTTCNNTT CNY                                                              13

(2) INFORMATION FOR SEQ ID NO:21:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:21:

TTATTGCCGT CATAGCGCGG                                                       20

(2) INFORMATION FOR SEQ ID NO:22:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:22:

GGCGACCTGT ATAACGTGTT                                                       20

(2) INFORMATION FOR SEQ ID NO:23:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:23:

```
GATGTTGCCT TTACTTCTAG GCCT                                                    24
```

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

```
AACTCATCAA TGTATCTTAT CATG                                                    24
```

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

```
TAATACGACT CACTATAGGG                                                         20
```

(2) INFORMATION FOR SEQ ID NO:26:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

```
GTGTGATCTG AAAACCCTGC TTGG                                                    24
```

(2) INFORMATION FOR SEQ ID NO:27:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

```
AGACTACTTC CCCATACATG CG                                                      22
```

(2) INFORMATION FOR SEQ ID NO:28:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

```
CCATACAGAG CAACATACCA GTAC                                                    24
```

(2) INFORMATION FOR SEQ ID NO:29:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

ACTTTTCTTC CCCTTTACAG CACAAATAAA GT                32

(2) INFORMATION FOR SEQ ID NO:30:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

ACTTTTGTTC ACCTGGATAG CACAAATAAA GT                32

(2) INFORMATION FOR SEQ ID NO:31:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

CGATGTTGCT CTGTATGGTA AGAACATCG                    29

(2) INFORMATION FOR SEQ ID NO:32:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

ACAAATAAAG TTTGAGTTCT AAACTCAT                     28

(2) INFORMATION FOR SEQ ID NO:33:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

CGATCGGTGA AATTGAAACT CGATCG                       26

(2) INFORMATION FOR SEQ ID NO:34:

(i) SEQUENCE CHARACTERISTICS:
        (A) LENGTH: 26 base pairs
        (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO:34:

CGATCGGTGA CATTGCGCAG CGATCG                                              26

(2) INFORMATION FOR SEQ ID NO:35:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

CCTAAGCATC TGGAAAGTCC CCAAGATGCT GAAC                                     34

(2) INFORMATION FOR SEQ ID NO:36:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

TTGGGGACTT TCCA                                                           14

(2) INFORMATION FOR SEQ ID NO:37:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

TTNCNNNNAA                                                                10

(2) INFORMATION FOR SEQ ID NO:38:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

AGTTTCNNTT YYYY                                                           14

(2) INFORMATION FOR SEQ ID NO:39:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA
```

```
        (xi) SEQUENCE DESCRIPTION: SEQ ID NO:39:

RRRRAANNGA AACT                                                             14

(2) INFORMATION FOR SEQ ID NO:40:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:40:

TTNCNNNNAA                                                                  10

(2) INFORMATION FOR SEQ ID NO:41:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: polyA_site
          (B) LOCATION: 18

(xi) SEQUENCE DESCRIPTION: SEQ ID NO:41:

AATAAAATTC TAGCACTA                                                         18

(2) INFORMATION FOR SEQ ID NO:42:

(i) SEQUENCE CHARACTERISTICS:
          (A) LENGTH: 14 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:42:

CATCCCCACC CTGG                                                             14

(2) INFORMATION FOR SEQ ID NO:43:

(i) SEQUENCE CHARACTERISTICS:
          (A) LENGTH: 14 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:43:

CATGGGTGGG GTGG                                                             14

(2) INFORMATION FOR SEQ ID NO:44:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA
```

(xi) SEQUENCE DESCRIPTION: SEQ ID NO:44:

AGGAGGAAAA ACTGTTTCAT ACG 23

(2) INFORMATION FOR SEQ ID NO:45:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:45:

TTCACACTGC CTAGATACT 19

(2) INFORMATION FOR SEQ ID NO:46:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:46:

CGTATGAAAC AGTTTTTCCT CCT 23

(2) INFORMATION FOR SEQ ID NO:47:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:47:

GAGTATCTAG GCAGTCTGAA 20

(2) INFORMATION FOR SEQ ID NO:48:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:48:

AGGGACTTTC CGG 13

(2) INFORMATION FOR SEQ ID NO:49:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:49:

TGGGGACTTT CCA 13

(2) INFORMATION FOR SEQ ID NO:50:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:50:

GGAGGCGTGG CC                                                12

(2) INFORMATION FOR SEQ ID NO:51:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:51:

TGGGCGGGAC                                                    10

(2) INFORMATION FOR SEQ ID NO:52:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:52:

TGGGGAGTGG C                                                11

(2) INFORMATION FOR SEQ ID NO:53:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:53:

CCGTAAAGTC CCTA                                          14

(2) INFORMATION FOR SEQ ID NO:54:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:54:

ACTGGGGAGT GGCGA                                       15

(2) INFORMATION FOR SEQ ID NO:55:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:55:

ATCTGGACGA TCAG                                                      14

(2) INFORMATION FOR SEQ ID NO:56:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:56:

GCCACTCCCC A                                                         11

(2) INFORMATION FOR SEQ ID NO:57:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:57:

GAGGCCACGC CTCCCT                                                    16

(2) INFORMATION FOR SEQ ID NO:58:

(i) SEQUENCE CHARACTERISTICS:
            (A) LENGTH: 9 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:58:

ATAAAGTAA                                                             9

(2) INFORMATION FOR SEQ ID NO:59:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:59:

TTCCCATTGA                                                           10

(2) INFORMATION FOR SEQ ID NO:60:

(i) SEQUENCE CHARACTERISTICS:
            (A) LENGTH: 14 base pairs
            (B) TYPE: nucleic acid
            (C) STRANDEDNESS: single (D) TOPOLOGY: linear (ii) MOLECULE TYPE: DNA (xi) SEQUENCE DESCRIPTION: SEQ ID NO:60:

ATTTCGTTTT GAGA                                                                14

(2) INFORMATION FOR SEQ ID NO:61:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:61:

AGTTGCATTC TTA                                                                 13

(2) INFORMATION FOR SEQ ID NO:62:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:62:

TTGCATCAT                                                                      9

(2) INFORMATION FOR SEQ ID NO:63:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:63:

CTACTAACA                                                                      9

(2) INFORMATION FOR SEQ ID NO:64:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:64:

GGTTTGCGTT CTAA                                                                14

(2) INFORMATION FOR SEQ ID NO:65:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:65:

ATACGACAGG GAAAAACAGC TGAATCTGTT TTTCCCTGTA TACG                44

(2) INFORMATION FOR SEQ ID NO:66:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:66:

ATACGGATCG AGGAGGAAAA ACTGTTTCAT ACGGATCGCT GAATCGATCT TCACACTGCC    60

TAGATACTCG ATCATACG                                                 78

(2) INFORMATION FOR SEQ ID NO:67:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:67:

ATACGGATCG CGTATGAAAC AGTTTTTCCT CCTGATCGCT GAATCGATCG AGTATCTAGG    60

CAGTCTGAAC GATCATACG                                                79

(2) INFORMATION FOR SEQ ID NO:68:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:68:

ATAGCTTCTG AGGGACTTTC CGGCTAGCTG AATCTAGCCG GAAAGTCCCT CAGATAATCA    60

(2) INFORMATION FOR SEQ ID NO:69:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:69:

TAGGGACTTT ACGG                                                     14

(2) INFORMATION FOR SEQ ID NO:70:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:70:

GTCCCGCCCA                                                                                    10

(2) INFORMATION FOR SEQ ID NO:71:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:71:

CCTAAGCATC TGGGCGGGAC GATGCTGAAC                                                               30

(2) INFORMATION FOR SEQ ID NO:72:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:72:

TCGCCAGTCC CCGT                                                                               14

(2) INFORMATION FOR SEQ ID NO:73:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:73:

CCTAAGCATC CCGTAAAGTC CCTAGATGCT GAAC                                                          34

(2) INFORMATION FOR SEQ ID NO:74:

(i) SEQUENCE CHARACTERISTICS:
            (A) LENGTH: 64 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:74:

ATAGCTTCTG TTGAAAGTCC CCATGAAGCC TGAATGCTTC ATGGGACTT TCAACAGATA          60

ATCA                                                                                          64

(2) INFORMATION FOR SEQ ID NO:75:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:75:

ATACGGATCG CATCCCCACC CTGGCGATCA TACG                                34

(2) INFORMATION FOR SEQ ID NO:76:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:76:

ATACGGATCG CATGGGTGGG GTGGCGATCA TACG                                34

(2) INFORMATION FOR SEQ ID NO:77:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:77:

GUAAAGUAA                                                            9

(2) INFORMATION FOR SEQ ID NO:78:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:78:

UUCCCUUUAA                                                           10

(2) INFORMATION FOR SEQ ID NO:79:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:79:

AGUUUCACUU GAAA                                                      14

(2) INFORMATION FOR SEQ ID NO:80:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:80:

GUAUGGUAA                                                            9

(2) INFORMATION FOR SEQ ID NO:81:

```
      (i) SEQUENCE CHARACTERISTICS:
          (A) LENGTH: 9 base pairs
          (B) TYPE: nucleic acid
          (C) STRANDEDNESS: single
          (D) TOPOLOGY: linear (ii) MOLECULE TYPE: RNA (xi) SEQUENCE DESCRIPTION: SEQ ID NO:81:

UUACGUCAU                                                             9

(2) INFORMATION FOR SEQ ID NO:82:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: RNA (xi) SEQUENCE DESCRIPTION: SEQ ID NO:82:

UUACUAAUCA                                                           10

(2) INFORMATION FOR SEQ ID NO:83:

(i) SEQUENCE CHARACTERISTICS:
          (A) LENGTH: 14 base pairs
          (B) TYPE: nucleic acid
          (C) STRANDEDNESS: single
          (D) TOPOLOGY: linear (ii) MOLECULE TYPE: RNA (xi) SEQUENCE DESCRIPTION: SEQ ID NO:83:

AGUUUGAGUU CUAA                                                      14

(2) INFORMATION FOR SEQ ID NO:84:

(i) SEQUENCE CHARACTERISTICS:
          (A) LENGTH: 14 base pairs
          (B) TYPE: nucleic acid
          (C) STRANDEDNESS: single
          (D) TOPOLOGY: linear (ii) MOLECULE TYPE: RNA (xi) SEQUENCE DESCRIPTION: SEQ ID NO:84:

GUGAAAUUGA AACU                                                      14

(2) INFORMATION FOR SEQ ID NO:85:

(i) SEQUENCE CHARACTERISTICS:
          (A) LENGTH: 9 base pairs
          (B) TYPE: nucleic acid
          (C) STRANDEDNESS: single
          (D) TOPOLOGY: linear (ii) MOLECULE TYPE: RNA (xi) SEQUENCE DESCRIPTION: SEQ ID NO:85:

UUACAGCAC                                                             9

(2) INFORMATION FOR SEQ ID NO:86:

(i) SEQUENCE CHARACTERISTICS:
          (A) LENGTH: 481 base pairs
          (B) TYPE: nucleic acid
```

(C) STRANDEDNESS: unknown
            (D) TOPOLOGY: unknown (ii) MOLECULE TYPE: RNA (xi) SEQUENCE DESCRIPTION: SEQ ID NO:86:

AAGCGGCGAG GUGCCUUUAC UACAUGUGUG AUCUGAAAAC CCUGCUUGGU UCUGAGCUGC        60

GUCUAUUGAA UUGGUAAAGU AAUACCAAUG GCUUUUAUC AUUCCUUCU UCCCUUUAAG         120

UUUCACUUGA AAUUUAAAA AUCAUGGUUA UUUUUAUCGU UGGGAUCUUU CUGUCUUCUG        180

GGUUCCAUUU UUUAAAUGUU UAAAAAUAUG UUGACAUGGU AGUUCAGUUC UUAACCAAUG       240

ACUUGGGGAU GAUGCAAACA AUUACUGUCG UUGGGAUUUA GAGUGUAUUA GUCACGCAUG       300

UAUGGGGAAG UAGUCUCGGG UAUGCUGUUG UGAAAUUGAA ACUGUAAAAG UAGAUGGUUG       360

AAAGUACUGG UAUGUUGCUC UGUAUGGUAA GAACUAAUUC UGUUACGUCA UGUACAUAAU       420

UACUAAUCAC UUUUCUUCCC CUUUACAGCA CAAAUAAAGU UUGAGUUCUA AACUCAUUAA       480

A                                                                     481

(2) INFORMATION FOR SEQ ID NO:87:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:87:

GTGTGATCTG AAAACCCTGC TTGG                                              24

(2) INFORMATION FOR SEQ ID NO:88:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:88:

CCATACAGAG CAACATACCA GT                                                22

(2) INFORMATION FOR SEQ ID NO:89:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:89:

TAGGGACTTT CCGG                                                         14

(2) INFORMATION FOR SEQ ID NO:90:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:90:

GTCCCGCCCA                                                              10

(2) INFORMATION FOR SEQ ID NO:91:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:91:

ATCTGGACGA TCAG                                                         14

(2) INFORMATION FOR SEQ ID NO:92:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:92:

TGGAAAGTCC CCAA                                                         14

(2) INFORMATION FOR SEQ ID NO:93:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:93:

CCTAAGCATC TTGGGGACTT TCCAGATGCT GAAC                                   34

(2) INFORMATION FOR SEQ ID NO:94:

(i) SEQUENCE CHARACTERISTICS:
            (A) LENGTH: 63 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:94:

ATAGCTTCTG ACTGGGGAGT GGCGAAAGCC TGAATGCTTA TCTGGACGAT CAGCAGATAA        60

TCA                                                                     63

(2) INFORMATION FOR SEQ ID NO:95:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:95:

CCTAAGCATC TAGGGACTTT ACGGGATGCT GAAC                                  34

(2) INFORMATION FOR SEQ ID NO:96:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:96:

CCTAAGCATC GTCCCGCCCA GATGCTGAAC                                        30

(2) INFORMATION FOR SEQ ID NO:97:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:97:

ATAGCTTCTG TCGCCAGTCC CCGTAAGCCT GAATGCTTAT CTGGACGATC AGCAGATAAT       60

CA                                                                     62

(2) INFORMATION FOR SEQ ID NO:98:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:98:

AGGGACTTTA CGG                                                         13

(2) INFORMATION FOR SEQ ID NO:99:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:99:

TGGGGACTTT CAA                                                         13

(2) INFORMATION FOR SEQ ID NO:100:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:100:

```
                                     -continued

AGUUUCNNUU CNY                                                         13

(2) INFORMATION FOR SEQ ID NO:101:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:101:

UUNCNNNAA                                                               9
```